(12) United States Patent
Fassihi et al.

(10) Patent No.: US 10,441,490 B2
(45) Date of Patent: Oct. 15, 2019

(54) SYSTEMS, METHODS, AND DEVICES FOR ARTIFICIAL PLACENTAS AND AMNIOTIC BED INCUBATORS

(71) Applicant: Amnion Life, LLC, Newport Beach, CA (US)

(72) Inventors: Amir Fassihi, Newport Beach, CA (US); Milos Ljubisa Radovanovic, Pozega (RS)

(73) Assignee: Amnion Life, LLC, Newport Beach, CA (US)

( * ) Notice: Subject to any disclaimer, the term of this patent is extended or adjusted under 35 U.S.C. 154(b) by 0 days.

(21) Appl. No.: 16/242,732

(22) Filed: Jan. 8, 2019

(65) Prior Publication Data

US 2019/0209408 A1    Jul. 11, 2019

Related U.S. Application Data

(60) Provisional application No. 62/615,354, filed on Jan. 9, 2018, provisional application No. 62/727,199, filed on Sep. 5, 2018.

(51) Int. Cl.
*A61G 11/00* (2006.01)
*A61K 35/50* (2015.01)
(Continued)

(52) U.S. Cl.
CPC ........... *A61G 11/00* (2013.01); *A61K 35/50* (2013.01); *A61K 35/51* (2013.01); *A61M 1/02* (2013.01);
(Continued)

(58) Field of Classification Search
CPC ......... A61G 11/00; A61K 35/50; A61K 35/51
(Continued)

(56) References Cited

U.S. PATENT DOCUMENTS 2,237,177 A   4/1941   Fischer
2,723,660 A   11/1955  Greenberg
(Continued)

FOREIGN PATENT DOCUMENTS

AT        164040       9/1949
CA        2614632 A1   1/2007
(Continued)

OTHER PUBLICATIONS

Partridge, Emily A. "An Extra-Uterine System to Physiologically Support the Extreme Premature Lamb", dated Apr. 25, 2017, Nature Communications, https://www.nature.com/articles/ncomms15112.
International Search Report in Application No. PCT/US2016/060388 dated Feb. 27, 2017, in 7 pages.
Kung, H.C., Hoyert, D.L., Xu, J. & Murphy, S. (2008). Deaths: Final Data for 2005. National Vital Statistics Report 56:10. Retrieved Sep. 10, 2008.
(Continued)

*Primary Examiner* — John P Lacyk
(74) *Attorney, Agent, or Firm* — Knobbe Martens Olson Bear LLP

(57) ABSTRACT

Described herein are systems, devices, and methods for an extracorporeal, artificial, placenta. In some embodiments, an artificial placenta and amniotic bed system may comprise a control unit, a gas delivery unit, a gas exchange unit or membrane oxygenator, a fluids delivery unit, an amniotic fluid bed, and a human machine interface. In some embodiments, the artificial placenta and amniotic bed systems, devices, and methods described herein may improve survival rates and minimize long-term disabilities in preterm, gestational-age, newborns. In some embodiments, the extracorporeal systems, devices, and methods comprise an artificial network through which oxygen and nutrient-rich blood may flow into a fetus (residing in an amniotic fluid bed), while carbon dioxide and wastes may be removed, thus re-establishing a form of intrauterine placental circulation.

20 Claims, 34 Drawing Sheets

(51) Int. Cl.
| | |
|---|---|
| *A61M 1/02* | (2006.01) |
| *A61K 35/51* | (2015.01) |
| *A61M 1/16* | (2006.01) |
| *A61M 1/36* | (2006.01) |
| *A01N 1/02* | (2006.01) |
| *A61M 5/44* | (2006.01) |
| *A61K 35/12* | (2015.01) |

(52) U.S. Cl.
CPC ........ *A61M 1/1698* (2013.01); *A61M 1/3667* (2014.02); *A01N 1/021* (2013.01); *A61K 2035/124* (2013.01); *A61M 1/1629* (2014.02); *A61M 5/44* (2013.01); *A61M 2202/0462* (2013.01); *A61M 2210/1458* (2013.01); *A61M 2210/1466* (2013.01); *C12N 2502/025* (2013.01)

(58) Field of Classification Search
USPC .......................................................... 600/22
See application file for complete search history.

(56) References Cited

U.S. PATENT DOCUMENTS

| | | |
|---|---|---|
| 3,025,831 A | 3/1962 | Berardi |
| 3,889,670 A | 6/1975 | Loveland et al. |
| 4,048,684 A | 9/1977 | Korner et al. |
| 4,079,728 A | 3/1978 | Gatts |
| 4,296,743 A | 10/1981 | Lasley |
| 5,084,011 A | 1/1992 | Grady |
| RE34,077 E | 9/1992 | Segall et al. |
| 5,207,639 A | 5/1993 | Cooper |
| 5,218,958 A | 6/1993 | Cooper |
| 5,308,310 A | 5/1994 | Roff et al. |
| 5,336,616 A | 8/1994 | Livesey et al. |
| 5,459,887 A | 10/1995 | Roman |
| 5,582,574 A | 12/1996 | Cramer |
| 6,001,552 A | 12/1999 | Cooper |
| 7,186,158 B1 | 3/2007 | Barber |
| 8,292,798 B2 | 10/2012 | Californiaa |
| 8,580,184 B2 | 11/2013 | Montoya |
| 9,492,603 B2 | 11/2016 | Fusch et al. |
| 9,662,257 B1 * | 5/2017 | Fassihi .................. A61G 11/00 |
| 10,166,161 B2 | 1/2019 | Fassihi et al. |
| 2004/0193096 A1 | 9/2004 | Cooper |
| 2007/0010005 A1 | 1/2007 | Sitzmann |
| 2008/0038372 A1 | 2/2008 | Kabayama |
| 2008/0097143 A1 | 4/2008 | Califorrniaa |
| 2008/0163425 A1 | 7/2008 | White |
| 2012/0116150 A1 | 5/2012 | Falk et al. |
| 2013/0316980 A1 | 11/2013 | Tchirikov |
| 2014/0221735 A1 | 8/2014 | Califorrniaa |
| 2014/0255253 A1 * | 9/2014 | Fusch .................. A61M 1/1698 422/48 |
| 2016/0022524 A1 | 1/2016 | Flake et al. |
| 2017/0128322 A1 | 5/2017 | Fassihi et al. |
| 2018/0044623 A1 | 2/2018 | Huh et al. |

FOREIGN PATENT DOCUMENTS

| | | |
|---|---|---|
| CN | 203663028 U | 6/2014 |
| CN | 203988807 U | 12/2014 |
| JP | 2013233194 A | 11/2013 |
| RU | 2140248 C1 | 10/1997 |
| RU | 79420 U1 | 1/2009 |
| RU | 118863 U1 | 8/2012 |
| WO | WO 2013/124086 | 8/2013 |
| WO | WO 2014/145494 | 9/2014 |
| WO | WO 2016/181189 | 11/2016 |
| WO | WO 2017/079477 | 5/2017 |
| WO | WO 2018/171905 | 9/2018 |

OTHER PUBLICATIONS

Silverman WA: Retrolental fibroplasias: a modern parable, New York, 1980, Grune & Stratton—Abstract.
World Health Organization: International statistical classification of diseases and related health problems, Tenth Revision, vol. 2, ed 2, Geneva, 2004 (Parts 1-5).
Liu L, Oza S, Hogan D, Perin J, Rudan I, Lawn JE, et al. Global, regional, and national causes of child mortality in 2000-13, with projections to inform post—2015 priorities: an updated systematic analysis. Lancet 2015;385:430-40.
Shah PS, Ye XY, Synnes A, Rouvinez-Bouali N, Yee W, Lee SK. Prediction of survival without morbidity for infants born at under 33 weeks gestational age: a user-friendly graphical tool. Arch Dis Child. 2012;97(2):F110-F115.
Cole TJ, Hey E, Richmond S. The PREM score: a graphical tool for predicting survival in very preterm births. Arch Dis Child. 2010;95(1):F14-F19.
Boyle EM, Poulsen G, Field DJ, et al. Effects of gestational age at birth on health outcomes at 3 and 5 years of age: population based cohort study. Br Med J. 2012;344:e896.
Escobar GJ, Clark RH, Greene JD. Short-term outcomes of infants born at 35 and 36 weeks gestation: we need to ask more questions. Sem Perinatol. 2006;30(1):28-33.
Ray KN, Lorch SA. Hospitalization of early preterm, late preterm, and term infants during the first year of life by gestational age. Hosp Pediatr. 2013;3(3):194-203.
Bérard A, Le Tiec M, De Vera MA. Study of the costs and morbidities of late-preterm birth. Arch Dis Child. 2012;97(5): F329-F334.
Kramer MS, Demissie K, Yang H, Platt RW, Sauve R, Liston R. The contribution of mild and moderate preterm birth to infant mortality. J Am Med Assoc. 2000;284(7):843-849.
Gilbert WM, Nesbitt TS, Danielsen B. The cost of prematurity: quantification by gestational age and birth weight. Obstet Gynecol. 2003;102(3):488-492.
Saigal S, Doyle LW. An overview of mortality and sequelae of preterm birth from infancy to adulthood. Lancet. 2008;371 (9608):261-269.
Gilbert WM. The cost of preterm birth: the low cost versus high value of tocolysis. BJOG: Int J Obstet Gynaecol 2006;113(Suppl. 3):4-9.
Russell RB, Green NS, Steiner CA, Meikle S, Howse JL, Poschman K, et al. Cost of hospitalization for preterm and low birth weight infants in the United States. Pediatrics 2007;120:e1-9.
Fanaroff AA, Stoll BJ, Wright LL, et al. Trends in neonatal morbidity and mortality for very low birthweight infants. Am J Obstet Gynecol. 2007;196(2):147.e1-147.e8.
Northway WH, Rosan RC, Porter DY. Pulmonary disease following respirator therapy of hyaline-membrane disease. N Engl J Med. 1967;276(7):357-368.
Klinger G, Sokolover N, Boyko V, Sirota L, Lerner-Geva L, Reichman B. Perinatal risk factors for bronchopulmonary dysplasia in a national cohort of very-low-birthweight infants. Am J Obstet Gynecol. 2013;208(2):115.e1-115.e9.
Gortner L, Misselwitz B, Milligan D, et al. Rates of bronchopulmonary dysplasia in very preterm neonates in europe: results from the MOSAIC cohort. Neonatology. 2011;99(2): 112-117.
Craig W. Intracranial haemorrhage in the newborn: a study of diagnosis and differential diagnosis based upon pathological and clinical findings in 126 cases. Arch Dis Child. 1938;13(74):89.
Ballabh P. Intraventricular hemorrhage in premature infants: of disease. Pediatr Res. 2010;67(1):1-8.
Papile L-A, Burstein J, Burstein R, Koffler H. Incidence and evolution of subependymal and intraventricular hemorrhage: a study of infants with birth weights less than 1500 gm. J Pediatr. 1978;92(4):529-534.
O'Shea TM, Allred EN, Kuban KCK, et al. Intraventricular hemorrhage and developmental outcomes at 24 months of age in extremely preterm infants. J Child Neurol. 2012;27(1):22-29.

(56) References Cited

OTHER PUBLICATIONS

Ancel PY, Livinec F, Larroque B, et al. Cerebral palsy among very preterm children in relation to gestational age and neonatal ultrasound abnormalities: the EPIPAGE cohort study. Pediatrics. 2006;117(3):828-835.
Neu J, Walker WA. Necrotizing enterocolitis. N Engl J Med. 2011;364(3):255-264.
Hellström A, Smith LEH, Dammann O. Retinopathy of prematurity. Lancet. 2013;382(9902):1445-1457.
Terry TL. Extreme prematurity and fibroblastic overgrowth of persistent vascular sheath behind each crystalline lens. I.preliminary report. Am J Ophthalmol. 1942;25(203):4.
Castillo A, Deulofeut R, Critz A, Sola A. Prevention of retinopathy of prematurity in preterm infants through changes in clinical practice and SpO2 technology. Acta Paediatr. 2011;100(2):188-192.
Rushing S, Ment LR. Preterm birth: a cost benefit analysis. Semin Perinatol. 2004;28(6):444-450.
Aly H, Hammad TA, Essers J, Wung JT. Is mechanical ventilation associated with intraventricular hemorrhage in preterm infants? Brain Develop. 2012;34(3):201-205.
Sarkar S, Schumacher RE, Baumgart S, Donn SM. Are new-borns receiving premedication before elective intubation? J Perinatol. 2006;26(5):286-289.
Bland RD, Clarke TL, Harden LB. Rapid infusion of sodium bicarbonate and albumin into high-risk premature infants soon after birth: a controlled, prospective trial. Am J Obstet Gynecol. 1976;124(3):263-267.
Carlo WA, Stark AR, Wright LL, et al. Minimal ventilation to prevent bronchopulmonary dysplasia in extremely-low-birth-weight infants. J Pediatr. 2002;141(3):370-375.
Wright KW, Sami D, Thompson L, Ramanathan R, Joseph R, Farzavandi S. A physiologic reduced oxygen protocol decreases the incidence of threshold retinopathy of prematurity. Trans Am Ophthalmol Soc. 2006;104:78.
Support Study Group of the Eunice Kennedy Shriver NICHD Neonatal Research Network. Target ranges of oxygen saturation in extremely preterm infants. N Engl J Med. 2010;362 (21):1959-1969.
Dempsey EM, Al Hazzani F, Barrington KJ. Permissive hypotension in the extremely low birthweight infant with signs of good perfusion. Arch Dis Child Fetal Neonatal Ed. 2009;94(4): F241-F244.
Evans JR, Lou Short B, Van Meurs K, Cheryl Sachs H. Cardiovascular support in preterm infants. Clin Ther. 2006;28 (9):1366-1384.
Goldkrand JW, Moore DH, Lentz SU, Clements SP, Turner AD, Bryant JL. Volumetric flow in the umbilical artery: nor-mative data. J Matern Fetal Med. 2000;9(4):224-228.
Skulstad SM, Kiserud T, Rasmussen S. Degree of fetal um-bilical venous constriction at the abdominal wall in a low-risk population at 20-40 weeks of gestation. Prenat Diagn. 2002;22(11):1022-1027.
Westin B, Nyberg R, Enhörning GA. Technique for perfusion of the previable human fetus. Acta Pædiatr. 1958;47(4): 339-349.
Callaghan JC, Maynes EA, Hug HR. Studies on lambs of the development of an artificial placenta. Review of nine long-term survivors of extracorporeal circulation maintained in a fluid medium. Can J Surg. 1965;8:208-213.
Zapol WM, Kolobow T, Pierce JG, Bowman RL. Artificial placenta: two days of total extrauterine support of the isolated premature lamb fetus. Science. 1969;166(3905): 617-618.
Chamberlain G. An artificial placenta: the development of an extracorporeal system for maintenance of immature infants with respiratory problems. Am J Obstet Gynecol. 1968;100(5):615-626.
Dorson W Jr, Meyer B, Baker E, et al. Response of dis-tressed infants to partial bypass lung assist. Trans Am Soc Artif Intern Organs. 1970;16:345-351.
Liggins GC, Howie RN. A controlled trial of antepartum glucocorticoid treatment for prevention of the respiratory distress syndrome in premature infants. Pediatrics. 1972; 50(4):515-525.

Ballard PL, Granberg P, Ballard RA. Glucocorticoid levels in maternal and cord serum after prenatal betamethasone therapy to prevent respiratory distress syndrome. J Clin Invest. 1975;56(6):1548-1554.
Bohn DJ, Miyasaka K, Marchak BE, Thompson WK, Froese AB, Bryan AC. Ventilation by high-frequency oscillation. J App Physiol. 1980;48(4):710-716.
Skinner SC, Hirschl RB, Bartlett RH. Extracorporeal life support. Semin Pediatr Surg. 2006;15(4):242-250.
Cilley RE, Zwischenberger JB, Andrews AF, Bowerman RA, Roloff DW, Bartlett RH. Intracranial hemorrhage during extracorporeal membrane oxygenation in neonates. Pediatrics. 1986;78(4):699-704.
Church et al. Pushing the Boundaries of ECLS: Outcomes in <34 Week EGA Neonates. Journal of Pediatric Surgery; 2017 (52):1810-1815.
Griffith BP, Borovetz HS, Hardesty RL, Hung TK, Bahnson HT. Arteriovenous ECMO for neonatal respiratory support. A study in perigestational lambs. J Thorac Cardiovasc Surg. 1979;77(4):595-601.
Kuwabara Y, Okai T, Imanishi Y, et al. Development of extrauterine fetal incubation system using extracorporeal membrane oxygenator. Artif Organs. 1987;11(3):224-227.
Kuwabara Y, Okai T, Kozuma S, et al. Artificial placenta: long-term extrauterine incubation of isolated goat fetuses. Artif Organs. 1989;13(6):527-531.
Unno N, Kuwabara Y, Okai T, et al. Development of an artificial placenta: survival of isolated goat fetuses for three weeks with umbilical arteriovenous extracorporeal membrane oxygenation. Artif Organs. 1993;17(12):996-1003.
Unno N, Kuwabara Y, Shinozuka N, et al. Development of artificial placenta: oxygen metabolism of isolated goat fetuses with umbilical arteriovenous extracorporeal membrane oxygenation. Fetal Diagn Ther. 1990;5(3-4):189-195.
Yasufuku M, Hisano K, Sakata M, Okada M. Arteriovenous extracorporeal membrane oxygenation of fetal goat incubated in artificial amniotic fluid (artificial placenta): influence on lung growth and maturation. J Pediatr Surg. 1998;33 (3):442-448.
Joseph T. Church, Megan A. Coughlin, Elena M. Perkins, Hayley R. Hoffman, John D. Barks, Raja Rabah, J. Kelley Bentley, Marc B. Hershenson, Robert H. Bartlett, George B. Mychaliska. The artificial placenta: Continued lung development during extracorporeal support in a preterm lamb model. Journal of Pediatric Surgery, vol. 53 , Issue 10, 2018.1896-1903.
Richardson DK, Corcoran JD, Escobar GJ, Lee SK. SNAP-II and SNAPPE-II: Simplified newborn illness severity and mortality risk scores. The Journal of pediatrics. 2001; 138(1):92-100.
Parry G, Tucker J, Tarnow-Mordi W. Group UKNSSC. CRIB II: an update of the clinical risk index for babies score. Lancet. 2003; 361(9371):1789-91.
Tyson JE, Parikh NA, Langer J, et al. Intensive care for extreme prematurity—moving beyond gestational age. The New England journal of medicine. 2008; 358(16):1672-81.
Awad JA, Cloutier R, Fournier L, et al. Pumpless respiratory assistance using a membrane oxygenator as an artificial placenta: a preliminary study in newborn and preterm lambs. Journal of investigative surgery. 1995; 8(1):21-30.
Reoma JL, Rojas A, Kim AC, et al. Development of an artificial placenta I: pumpless arterio-venous extracorporeal life support in a neonatal sheep model. Journal of pediatric surgery. 2009; 44(1):53-9.43.
Arens J, Schoberer M, Lohr A, et al. NeonatOx: a pumpless extracorporeal lung support for premature neonates. Artificial organs. 2011; 35(11):997-1001. [PubMed: 21995519].
Miura Y, Matsuda T, Funakubo A, et al. Novel modification of an artificial placenta: pumpless arteriovenous extracorporeal life support in a premature lamb model. Pediatric research. 2012; 72(5):490-4. This study describes the use of a prototype oxygenator to provide pumpless AV AP support in a model of fetal sheep. Fetal sheep survival was significantly improved over prior published studies (18.2h ± 3.2h vs. 3.5h ± 0.4h).

(56) References Cited

OTHER PUBLICATIONS

Seo T, Ito T, Iio K, et al. Experimental study on the hemodynamic effects of veno-arterial extracorporeal membrane oxygenation with an automatically driven blood pump on puppies. Artificial organs. 1991; 15(5):402-7.

Gray BW, El-Sabbagh A, Rojas-Pena A, et al. Development of an artificial placenta IV: 24 hour venovenous extracorporeal life support in premature lambs. ASAIO journal. 2012; 58(2):148-54.

Gray BW, El-Sabbagh A, Zakem SJ, et al. Development of an artificial placenta V: 70 h veno-venous extracorporeal life support after ventilatory failure in premature lambs. Journal of pediatric surgery. 2013; 48(1):145-53.

Mychaliska, George. A Paradigm Shift in the Treatment of Prematurity: The Artificial Placenta; https://www.youtube.com/watch?v=861cnU3WLM0; Published on Jun. 22, 2018.

International Search Report and Written Opinion in Application No. PCT/US2019/012747 dated Apr. 29, 2019 in 9 pages.

* cited by examiner

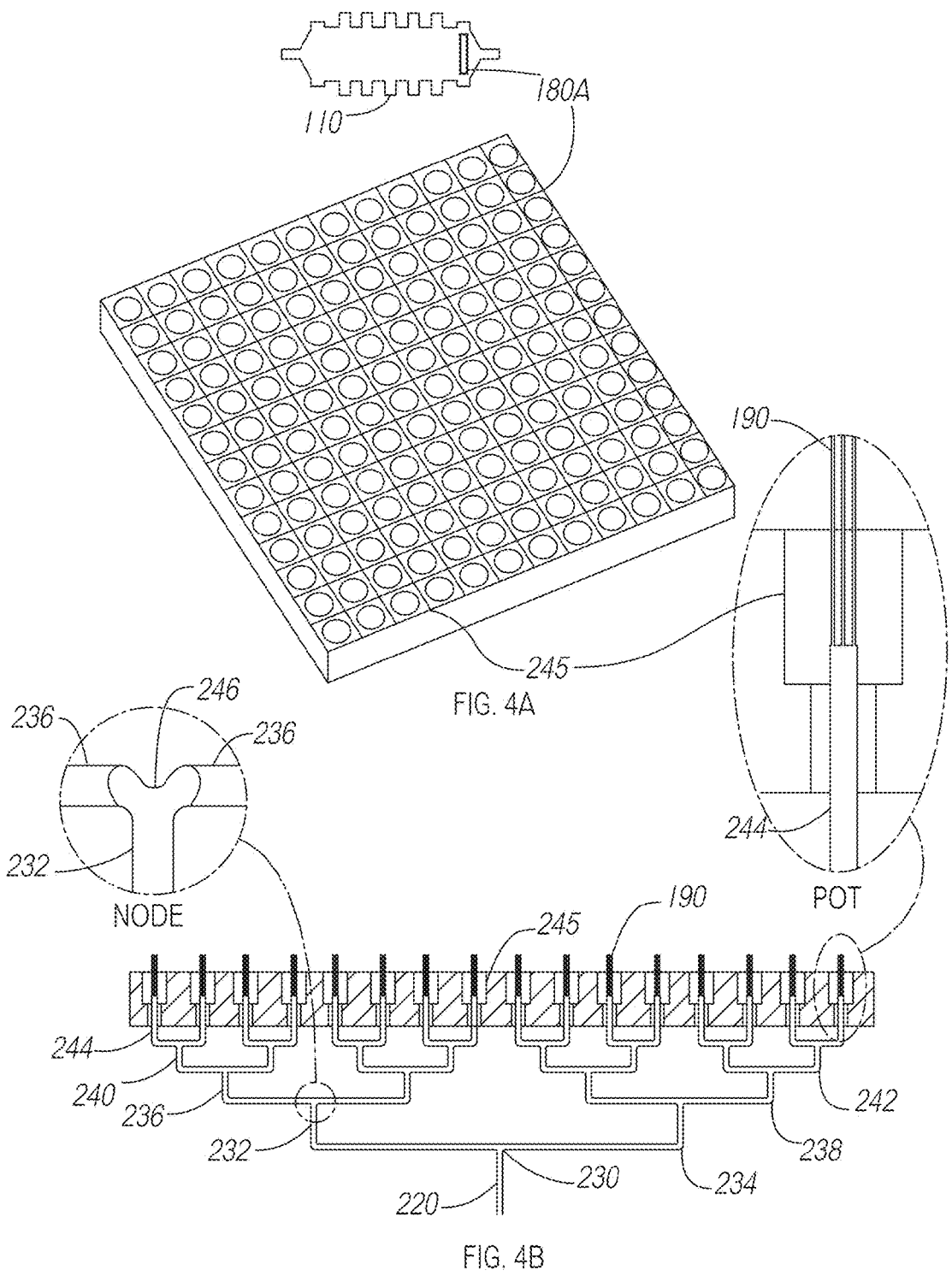

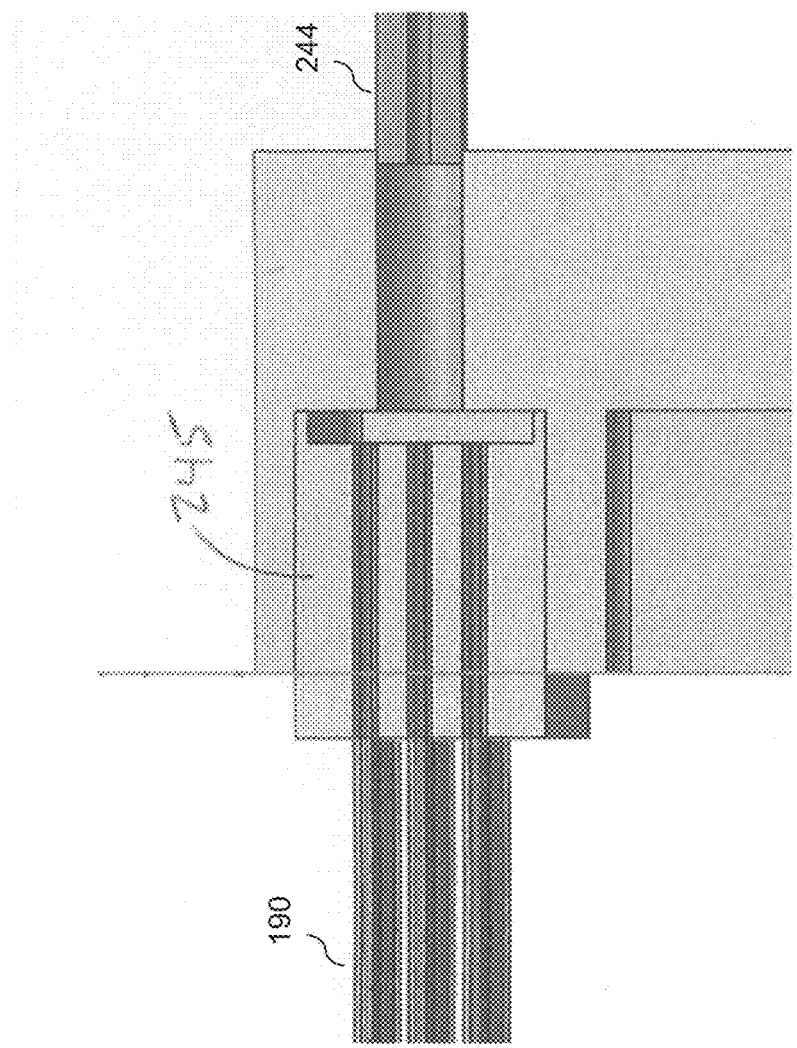

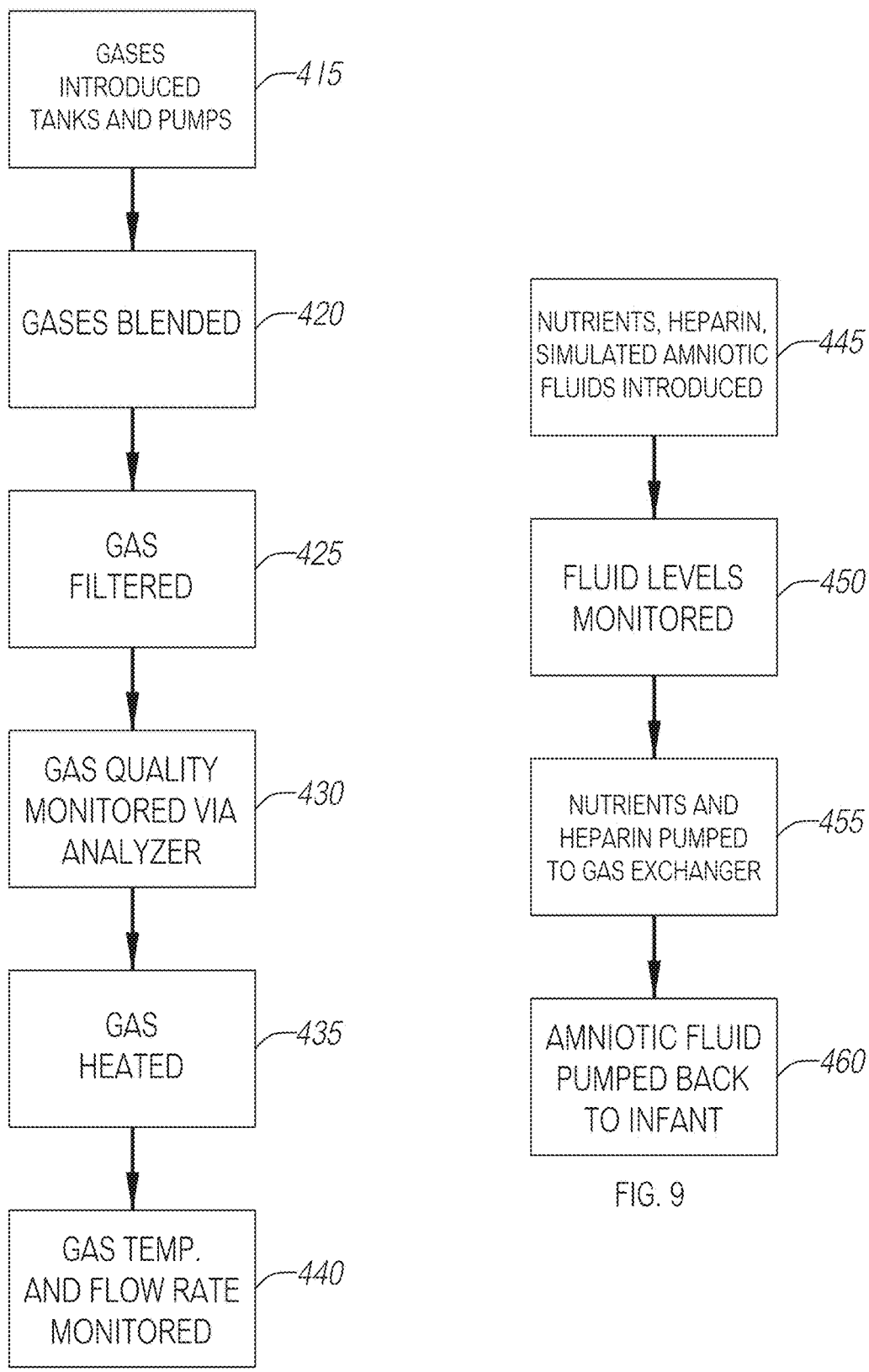

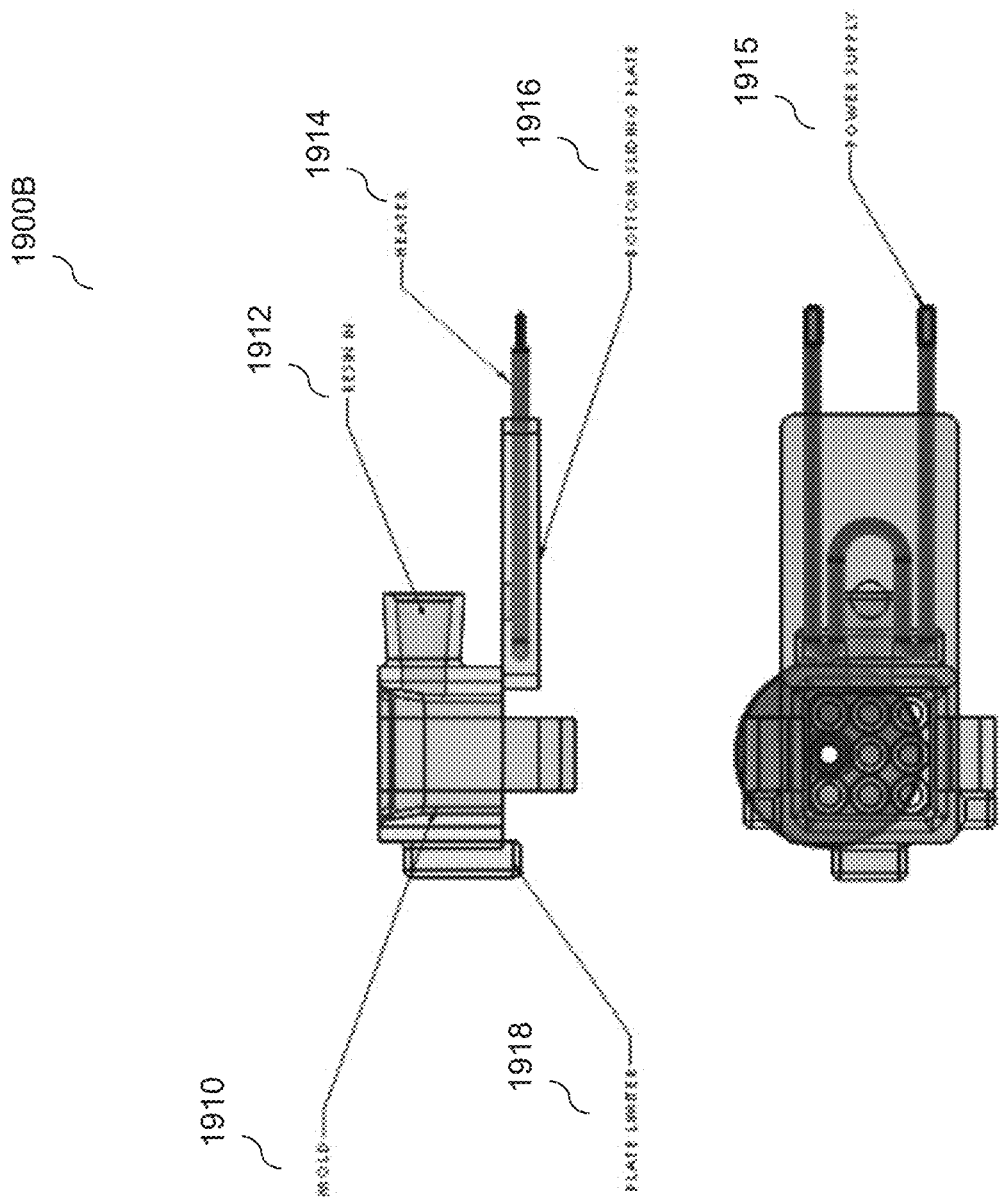

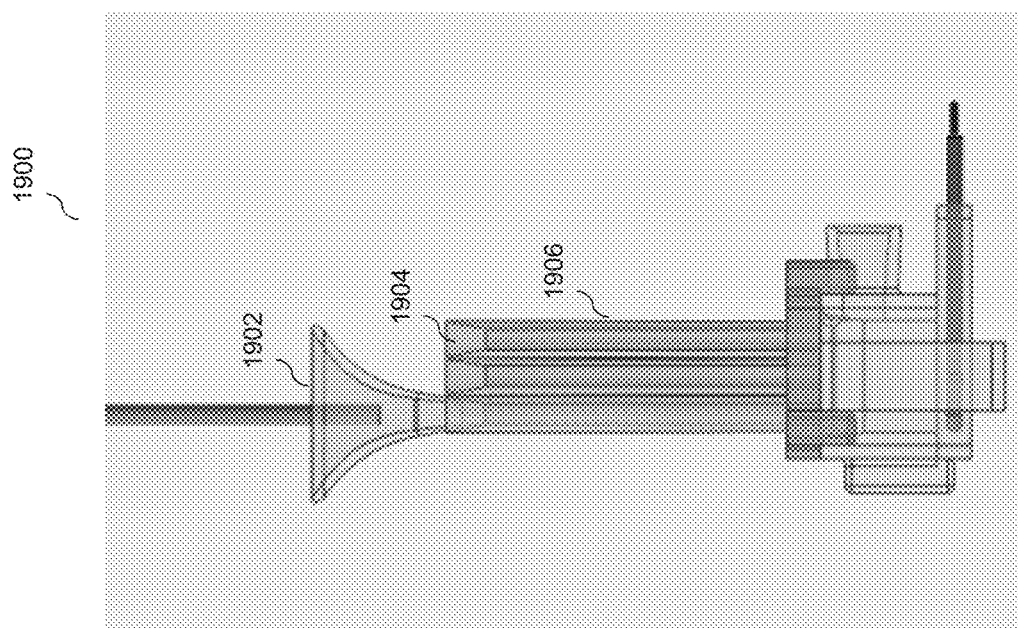

SYSTEMS, METHODS, AND DEVICES FOR ARTIFICIAL PLACENTAS AND AMNIOTIC BED INCUBATORS

CROSS-REFERENCE TO RELATED APPLICATION(S)

The present application claims the benefit under 35 U.S.C. § 119(c) of U.S. Provisional Patent Application No. 62/615,354, filed Jan. 9, 2018, and Provisional Patent Application No. 62/727,199, filed Sep. 5, 2018, each of which is incorporated herein by reference in its entirety under 37 C.F.R. § 1.57. Any and all applications for which a foreign or domestic priority claim is identified in the Application Data Sheet as filed with the present application are hereby incorporated by reference under 37 C.F.R. § 1.57.

BACKGROUND

Field

The present invention relates to the field of neonatal care. More specifically, the invention provides a method for the maintenance of homeostasis in infants outside of the womb.

Description

The perinatal period is critical in human development. During this period, the infant makes the critical transition from its dependence on maternal and placental support (oxidative, nutritional, and endocrinologic) and establishes an independent life. The difficulty of this transition is determined by mortality risks that are higher than those born at later gestational any occurring until old age and by risks for damage to organ systems, most notably the brain. In addition, the developing organ systems do not always demonstrate the immediate negative effects of developmental insults during preterm infant care in a neonatal intensive care unit (NICU). At times, years may pass before the effects on higher cortical functions, of insults and injuries occurring during the perinatal period can be detected reliably.

Premature birth is the early and often sudden delivery of a baby before 37 weeks of a normal 37-40 week term and is the second highest cause of infant deaths across the world. Premature birth and the sudden transition to postnatal life is disruptive to premature infants who are in a period of rapid growth and maturation. Mortality in the first year of a premature baby's life increases dramatically with decreasing gestational age. As such, preterm birth is a leading contributor to infant death and the leading cause of long-term neurological disabilities in children.

The principal complications of premature birth involve five organs: the lung, heart, gut, eye, and brain. Many of these complications are life threatening in the short term and lead to long-term morbidity. The high frequency of brain damage in survivors of premature birth, remains the largest unsolved problem in neonatal medicine. The extraordinary decline in mortality rates has not been paralleled by similar declines in rates of neurodevelopmental disabilities in survivors. The costs of care of these complications, especially lifelong care of those with neurodevelopmental disability, may reach millions of U.S. dollars.

These complications are caused partially by organ immaturity and partially by the attempts to treat these infants with the same strategies used to treat term infants. Many complications sustained by extremely low gestational age newborns are caused by or exacerbated by current methods of neonatal care used to treat their life-threatening problems. For instance, mechanical ventilation, procedures under inadequate sedation, and rapid administration of intravenous fluids have been implicated in the development of IVH. Other critical therapies have been associated with morbidity as well. Positive pressure ventilation has been associated with bronchopulmonary dysplasia, prompting minimal ventilation strategies to avoid it. High oxygen concentration has been linked with ROP, spurring efforts to reduce fraction of inspired oxygen in neonatal care. The use of vasoconstrictors for the treatment of neonatal hypotension has drawn similar scrutiny.

There is therefore a need for providing better care for neonatal infants, for example for providing alternative solutions that allow the administration of oxygenated blood and/or nutrients to neonatal infants.

SUMMARY

For purposes of summarizing the embodiments and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

Some embodiments herein relate to an extracorporeal artificial placenta and amniotic bed system for the administration of oxygenated blood through an umbilical cord of an infant, the extracorporeal artificial placenta and amniotic bed system comprising: a simulated amniotic fluid bed comprising a thermo-regulated fluid environment configured to accommodate a body of the infant therein while maintaining a head of the infant above the thermo-regulated fluid environment; a fluid injection system configured to fill lungs of the infant with simulated amniotic fluid while the head of the infant is maintained above the thermo-regulated fluid environment; and an extra-uterine membrane oxygenation system configured to oxygenate blood of the infant, the extra-uterine membrane oxygenation system comprising: one or more arterial lines connected to the umbilical cord of the infant and configured to receive low-oxygen blood from the infant; a gas exchange unit comprising: an inflow capillary tree comprising a first branching structure, wherein the inflow capillary tree is configured to deliver the low-oxygen blood to a hollow fiber unit comprising one or more semipermeable hollow fibers capable of oxygenating the low-oxygen blood passing through the hollow fiber unit; and an outflow capillary tree comprising a second branching structure, wherein the second branching structure mirrors the first branching structure, and wherein the outflow capillary tree is configured to deliver oxygenated blood from the hollow fiber unit; and one or more venous lines connected to the umbilical cord of the infant and configured to receive the oxygenated blood from the outflow capillary tree and deliver the oxygenated blood to the infant. wherein the one or more hollow fibers are positioned in a geometric array, wherein each of the one or more hollow fibers is located substantially equidistantly from each adjacent hollow fiber of the hollow fiber unit, and wherein each of the one or more hollow fibers is oriented substantially parallel each other hollow fiber.

In some embodiments, an extracorporeal artificial placenta and amniotic bed system for the administration of oxygenated blood through an umbilical cord of an infant comprises: a simulated amniotic fluid bed comprising a thermo-regulated fluid environment configured to accommodate a body of the infant therein while maintaining a head of the infant above the thermo-regulated fluid environment; a fluid injection system configured to fill lungs of the infant with simulated amniotic fluid while the head of the infant is maintained above the thermo-regulated fluid environment; and an extra-uterine membrane oxygenation system configured to oxygenate blood of the infant, the extra-uterine membrane oxygenation system comprising: one or more arterial lines connected to the umbilical cord of the infant and configured to receive low-oxygen blood from the infant; a gas exchange unit comprising: an inflow capillary tree comprising a first branching structure, wherein the inflow capillary tree is configured to deliver the low-oxygen blood to a hollow fiber unit comprising one or more semipermeable hollow fibers capable of oxygenating the low-oxygen blood passing through the hollow fiber unit; and an outflow capillary tree comprising a second branching structure, wherein the second branching structure mirrors the first branching structure, and wherein the outflow capillary tree is configured to deliver oxygenated blood from the hollow fiber unit; and one or more venous lines connected to the umbilical cord of the infant and configured to receive the oxygenated blood from the outflow capillary tree and deliver the oxygenated blood to the infant.

In some embodiments of the extracorporeal artificial placenta and amniotic bed system, the extra-uterine membrane oxygenation system further comprises a catheter for connecting the one or more arterial lines and the one or more venous lines to the umbilical cord of the infant. In some embodiments, the extra-uterine membrane oxygenation system further comprises an anchor for maintaining the catheter above the thermo-regulated fluid environment.

In some embodiments of the extracorporeal artificial placenta and amniotic bed system, the inflow capillary tree and the outflow capillary tree do not comprise any sharp edges. In some embodiments of the extracorporeal artificial placenta and amniotic bed system, the first branching structure of the inflow capillary tree and the second branching structure of the outflow capillary tree comprise one or more branching angles or branch diameters that naturally occur in a human body, such that the inflow capillary tree and outflow capillary tree mimic a branching of a natural capillary tree.

In some embodiments of the extracorporeal artificial placenta and amniotic bed system, the simulated amniotic fluid bed further comprises: an incubating tank comprising simulated amniotic fluid; one or more heating elements; one or more temperature sensors; and one or more thermostats comprising a temperature regulation mechanism. In some embodiments, the simulated amniotic fluid comprises one or more of the following: electrolytes, minerals, proteins, peptides, lipids, lactate, pyruvate, enzymes, hormones, or amniotic stem cells.

In some embodiments, the extracorporeal artificial placenta and amniotic bed system further comprises a gas delivery unit configured to supply a gas mixture to the gas exchange unit at a predetermined pressure and/or temperature, the gas delivery unit comprising: a gas supply; one or more inlet gas connectors configured to deliver one or more gases from the gas supply to an interior of the gas delivery unit; one or more gas control valves configured to control the flow of the one or more gases; a blender configured to blend the one or more gases into the gas mixture at a predetermined mixing ratio; a gas filter comprising a porous filter membrane configured to prevent impurities from entering the gas mixture; and one or more outlet gas connectors configured to deliver the gas mixture from the interior of the gas delivery unit to the gas exchange unit. In some embodiments, the gas mixture comprises oxygen and ambient air. In some embodiments, the gas supply comprises a central gas delivery system of a hospital.

In some embodiments, the extracorporeal artificial placenta and amniotic bed system further comprises a graphical user interface configured to allow a user to monitor and control the simulated amniotic fluid bed extra-uterine membrane oxygenation system.

In some embodiments, the extracorporeal artificial placenta and amniotic bed system further comprises a fluids delivery unit configured to deliver one or more fluids to the blood of the infant, the fluids delivery unit comprising: one or more fluid tanks, each fluid tank storing a fluid of the one or more fluids; one or more fluid pumps configured to meter the fluids at a predetermined flow rate into the one or more arterial lines and/or the one or more venous lines. In some embodiments, at least one of the one or more fluid tanks comprises a disposable fluid cartridge. In some embodiments, the fluids delivery unit further comprises one or more backflow preventers for stopping a backwards flow of the one or more fluids through the fluids delivery unit. In some embodiments, the one or more fluids comprise simulated amniotic fluid, nutrients, or Heparin.

In some embodiments of the extracorporeal artificial placenta and amniotic bed system, the one or more venous lines comprise a bubble trap configured to remove bubbles from the one or more venous lines. In some embodiments, of the extracorporeal artificial placenta and amniotic bed system, the one or more venous lines comprise a Luer port configured to allow direct pharmaceuticals administration to the oxygenated blood.

In some embodiments, the extracorporeal artificial placenta and amniotic bed system further comprises a control unit configured to monitor and control the simulated amniotic fluid bed and/or the extra-uterine membrane oxygenation system, the control unit comprising: a plurality of system sensors configured to transmit system state data; a plurality of system control valves; one or more computer readable storage devices configured to store a plurality of computer executable instructions; and one or more hardware computer processors in communication with the one or more computer readable storage devices and configured to execute the plurality of computer executable instructions in order to cause the control unit to: continuously monitor the artificial placenta and amniotic bed system by receiving and analyzing the system state data from the plurality of system sensors; control one or more physical or chemical properties of blood, gas, and/or fluid within the extracorporeal artificial placenta and amniotic bed system by sending a generated command to the one or more of the plurality of system control valves.

In some embodiments of the extracorporeal artificial placenta and amniotic bed system, the gas exchange unit further comprises a jacket, wherein the jacket encases the hollow fiber unit and seals an interior of the gas exchange unit.

In some embodiments of the extracorporeal artificial placenta and amniotic bed system, the fluid injection system comprises one or more tubes, and the one or more tubes are attached to one or both nostrils and/or a mouth of the infant.

Some embodiments described herein relate to a clinical method for maintaining fetal blood circulation, providing a normal partial pressure of oxygen in lungs of an infant patient, and avoiding potentially harmful mechanical ventilation to the lungs comprises: placing a body of the infant patient in a simulated amniotic fluid bed comprising a thermo-regulated fluid environment configured to accommodate the infant therein while maintaining a head of the infant patient above the thermo-regulated fluid environment; connecting, to the infant patient in an extra-uterine membrane oxygenation system configured to oxygenate the blood of the infant patient, the extra-uterine membrane oxygenation system comprising: one or more arterial lines connected to the umbilical cord of the infant and configured to receive low-oxygen blood from the infant; a gas exchange unit comprising: an inflow capillary tree comprising a first branching structure, wherein the inflow capillary tree is configured to deliver the low-oxygen blood to a hollow fiber unit comprising one or more semipermeable hollow fibers capable of oxygenating the low-oxygen blood passing through the hollow fiber unit; and an outflow capillary tree comprising a second branching structure, wherein the second branching structure mirrors the first branching structure, and wherein the outflow capillary tree is configured to deliver oxygenated blood from the hollow fiber unit; and one or more venous lines connected to the umbilical cord of the infant and configured to receive the oxygenated blood from the outflow capillary tree and deliver the oxygenated blood to the infant.

BRIEF DESCRIPTION OF THE DRAWINGS

These features, aspects, and advantages of the present systems, methods, and devices will become better understood with regard to the following description, appended claims, and accompanying drawings which illustrate exemplary features. However, it is to be understood that each of the features can be used in the embodiments in general, not merely in the context of the particular drawings, and the invention includes any combination of these features.

A better understanding of the systems, devices, and methods described herein will be appreciated upon reference to the following description in conjunction with the accompanying drawings, wherein:

FIG. 4A is a schematic perspective view of an example pot grid for connecting sub-branches of a capillary tree with hollow fibers according to various embodiments herein;

FIG. 4B is a sectional view of a sub-branch of the capillary tree, pots, and hollow fibers according to various embodiments herein;

FIG. 4C illustrates a close-up sectional view of an example pot of the array of pots according to various embodiments herein;

FIG. 8 is a flowchart of example gas delivery process according to various embodiments herein;

FIG. 9 is a flowchart of an example fluid delivery process according to various embodiments herein;

FIG. 19B illustrates an example molding mechanism according to various embodiments herein;

FIG. 19C illustrates a top view of a combined assembly and molding mechanism according to various embodiments herein;

FIG. 19D illustrates a side view of a combined assembly and molding mechanism according to various embodiments herein;

DETAILED DESCRIPTION

Figure 1:
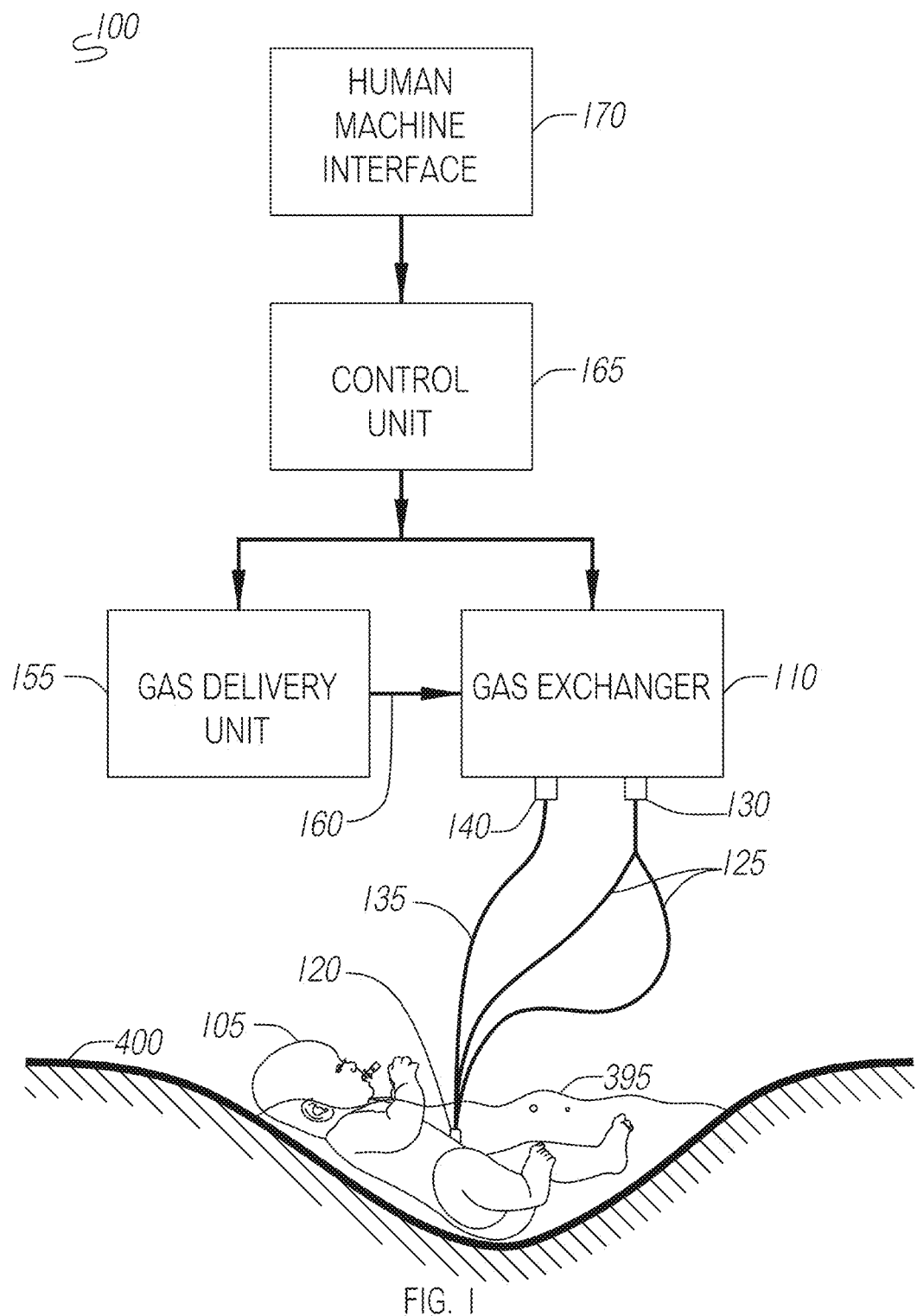
FIG. 1 is schematic diagram of an example embodiment of the artificial placenta and amniotic bed system according to various embodiments herein.

The devices, systems, and methods described herein relate in some aspects to an artificial placenta. In particular, some embodiments relate to an artificial placenta that may receive blood from a preterm infant's umbilical cord and/or return treated blood to a preterm infant's umbilical cord. Although certain embodiments of the artificial placenta is illustrated and described in the context of being useful for preterm infants, the same and/or other embodiments can be useful in other instances. Accordingly, the devices, systems, and methods are not intended to be limited to the examples and embodiments described herein.

Generally, preterm infants have the greatest risks of disability or death in the period immediately after birth. As such, systems, methods, and devices are needed to facilitate critical organ development outside of the mother's womb until infants' bodies and lungs are ready to breathe air regularly. Although some existing treatments address prematurity, many treatments, such as mechanical ventilation, may contribute to complications because a preterm infant's lungs are often too fragile to handle even the gentlest ventilation techniques.

Neonatal deaths (i.e. deaths in the first 28 days of life), are largely related to premature birth and birth defects. The principal complications of premature birth involve five organs: the lungs, heart, gut, eyes, and brain. The lungs may be affected by respiratory distress syndrome, including its short and long-term complications, and/or chronic lung disease (CLD) or bronchopulmonary dysplasia (BPD). Regarding the heart, symptomatic patent ductus arteriosus is the major cardiac challenge in premature infants. The gut may be affected by necrotizing enterocolitis (NEC), a disorder that in its most extreme forms can cause death or substantial loss of bowel function. The eyes may be affected by retinopathy of prematurity (ROP), which is closely related to arterial oxygen levels. The epidemic level of this disorder encountered in the 1950s, when oxygen was freely administered without monitoring, was a major setback for neonatal medicine. However, even with more careful management of oxygen, retinopathy of prematurity continues to occur in about 3-16% of premature infants. Finally, the brain may be affected by intraventricular hemorrhages (IVH), white matter injury (WMI), which may be a more reliable indicator of long-term developmental disability, and cerebral palsy (CP).

Many of these complications are life threatening in the short term and may lead to long-term morbidity. The high frequency of brain damage in survivors of premature birth remains the one of the largest unsolved problems in neonatal medicine. The extraordinary decline in mortality rates has not been paralleled by similar declines in rates of neurodevelopmental disabilities in survivors. The costs of care of these complications, especially lifelong care of those with neurodevelopmental disability, may reach millions of USD.

These complications are caused partially by organ immaturity and partially by the attempts to treat these infants with the same strategies used to treat normal term infants. Many complications sustained by extremely low gestational age newborns are caused by or exacerbated by current methods of neonatal care used to treat their life-threatening problems. For instance, mechanical ventilation, procedures under inadequate sedation, and rapid administration of intravenous fluids have been implicated in the development of IVH. Other critical therapies have been associated with morbidity as well. Positive pressure ventilation has been associated with bronchopulmonary dysplasia, prompting minimal ventilation strategies to avoid it. High oxygen concentration has been linked with ROP, spurring efforts to reduce the fraction of inspired oxygen in neonatal care. The use of vasoconstrictors for the treatment of neonatal hypotension has drawn similar scrutiny. The systems, methods, and devices disclosed herein may introduce new designs and innovations to avoid the present issues with neonatal care of preterm infants.

The concept of the artificial placenta and uterine environment (APUE) offers an appealing option for, e.g., extremely preterm infants by returning them to a uterine-like environment. In some embodiments, the artificial placenta must match the performance of native placenta, and control or replace several organ systems on an as-needed basis. In some embodiments, the artificial placenta must retain the fetal circulation to bypass the developing lungs. In some embodiments, the artificial placenta could partially take over gas exchange function until the infant recovers from the initial cause of lung incompetence during the early postnatal period. In some embodiments, the artificial placenta could be applied to the newborn infant in conjunction with other forms of respiratory support. The additional extracorporeal gas exchange could improve survival rates of preterm and/or term newborn infants with respiratory failure when mechanical ventilation is insufficient. Further, the artificial placenta could decrease the occurrence of chronic lung disease by reducing the amount of mechanical ventilation. In some embodiments, this could especially benefit early preterm infants.

In some embodiments, the artificial placenta should mimic the function of the native placenta in totality, decrease mortality of preterm infants, and eliminate short and long term survivor morbidity, making it a better proposition than current standards of neonatal care.

In some embodiments, the patients most likely to benefit from artificial support are ELGANs (<28 weeks EGA). Infants at high risk for mortality can be identified within the first hour of life or the first 12 hours of life using, for example, the Clinical Risk Index for Babies (CRIB II) or the Score for Neonatal Acute Physiology—Perinatal Extension II (SNAPPE II). The overall mortality and morbidity of ELGANs has remained substantial; infants at 22-25 weeks EGA are reported to have 49% mortality by 18 to 22 months.

In some embodiments, the principle of treating a preterm infant as a fetus rather than a neonate is a paradigm shift in neonatal care. The innovative artificial placenta and amniotic bed technology described herein offers novel methods, devices, and systems for the treatment of preterm birth.

In some embodiments, the artificial placenta systems, method, and devices described herein can be used independently from any incubator. In some embodiments, the artificial placenta may be utilized with any standard neonatal air controlled incubator. In some embodiments, the artificial placenta system described herein can be coupled with, for example, an Amniotic Bed by Amnion Life. The Amniotic Bed by Amnion Life and described in U.S. Pat. No. 9,662,257, which is incorporated herein by reference in its entirety, provides significant improvements in the incubation of preterm infants. The Amniotic Bed is a fluid filled incubator designed to provide significant improvement in thermoregulation, hydration, comfort, and skin protection over conventional incubators and radiant warmers. However, the artificial placenta systems described herein do not require any amniotic bed/bath to operate and can also be used in conjunction with any air controlled incubators. For example, the artificial placenta systems, methods, and devices described herein may be utilized with incubators manufactured according to, for example, standard *ANSI/RAMI/IEC 60601-2-19:2009 Medical Electrical Equipment Û Part 2-19: Particular Requirements for the Basic Safety and Essential Performance of Infant Incubators.*

The devices, systems, and methods described herein relate in some aspects to neonatal incubators, and more specifically to amniotic bath incubators for mammals, such as infants including premature infants, preterm infants, and/or low birth weight term infants, including veterinary applications. In some embodiments, the incubators could be utilized for non-neonates, such as, for example, hypothermic or otherwise ill children or adults in some cases. Some embodiments of the devices, systems, and methods described herein can have several significant benefits for such infants compared to the currently existing technologies of convection and radiant-based incubators. Not to be limited by theory, some of such benefits can include, for example, one or more of the following: (1) improved thermoregulation, (2) improved hydration through reconstitution of the in-utero intramembranous pathway of fluid absorption, (3) provision of a fluid environment for exercise and movement of appendages of the infant, and (4) providing of a more natural environment for skin development.

As discussed, some devices, systems, and methods described herein can be used with a simulated fluid environment similar to the mother's womb to recreate a more familiar environment for infants, including infants born before their ideal due date, low birth weight term infants, and/or normal birth weight term infants during the first 24 or 48 hours. The devices, systems, and methods described herein can provide an artificial placenta with an amniotic bed system for improved thermoregulation, comfort, and hydration for pre-term, term, and/or older infants. One or more such advantages, such as thermoregulation, can be particularly important before, during, and/or after surgical procedures. In some embodiments, an amniotic bath incubator can comprise an incubating tank with synthetic or simulated amniotic fluid, a heating element(s), a temperature sensor(s), and/or thermostat(s) for temperature regulation. An infant or premature infant can be placed in the incubating tank to provide a thermo-regulated fluid environment to the infant, in which the fluid can be made similar to physiologic amniotic fluid. For example, the osmolality, electrolyte and mineral content of the synthetic or simulated amniotic fluid in which the infant is placed can be similar to those of physiologic amniotic fluid. In some embodiments, an infant can be placed in the incubating tank such that the body of the infant is submerged in synthetic amniotic fluid, while the head of the infant is maintained above fluid level. In some embodiments, an infant can be fully submerged in synthetic amniotic fluid.

The physiologic amniotic fluid in the mother's womb is the protective liquid bathing the fetus during pregnancy and serves as a heat reservoir for thermoregulation and a reservoir for absorption of water by the fetus through the intramembranous pathway. It also provides an environment for fetal movement and comfort while maintaining a steady temperature of 37° C. for the developing infant. Amniotic fluid contains electrolytes, minerals, proteins, peptides, lipids, lactate, pyruvate, enzymes, hormones and amniotic stem cells.

As such, in some embodiments, the temperature of the synthetic or simulated amniotic bath is regulated by use of one or more temperature sensors and/or heaters to maintain a temperature of about 37° C. for the infant. The synthetic or simulated amniotic fluid can also comprise one or more electrolytes, minerals, proteins, peptides, lipids, lactate, pyruvate, enzymes, hormones and amniotic stem cells.

In some embodiments, the systems, methods, and devices described herein are related to artificial placenta and amniotic bed systems, whether to be used in combination or separately. Generally speaking, the placenta provides oxygen and nutrients to the fetus, to ensure normal fetal growth and development, whilst removing carbon dioxide and other waste products. It metabolizes a number of substances and can release metabolic products into maternal and/or fetal circulations. Also, the placenta can help protect the fetus against certain xenobiotic molecules, infections and maternal diseases. In addition, it releases hormones into both the maternal and fetal circulations to affect pregnancy, metabolism, fetal growth, parturition and other functions. Many placental functional changes occur that accommodate the increasing metabolic demands of the developing fetus throughout gestation.

Generally speaking, in utero, the developing fetus is connected to the placenta, which serves as the interface between maternal and fetal circulations and provides fetal nutrient uptake, metabolites elimination, and gas exchange via the mother's blood. On the fetal side, the placenta is connected in parallel to the systemic circulation of the fetus; blood from the descending aorta is channeled through the umbilical arteries to the placenta and back to the body and central venous system via the umbilical vein. Fetal blood flow through the placenta ranges from 90 to 180 mL/kg per min, depending on gestational age of the fetus, which represents about 20% to 30% of total cardiac output.

After birth, the function of the organs of the newborn must immediately adapt to the extra-uterine environment after being disconnected from the placental supply. In preterm and term infants with developing lungs or severe postnatal respiratory insufficiency, it would be beneficial to re-connect these newborns to a placenta and allow partial fetal circulation to facilitate extracorporeal gas exchange. Although this cannot be done anymore with the natural placenta, yet, it may be useful to construct a device in its place.

As such, in some embodiments, an artificial placenta is provided to further return preterm infants to a uterine-like environment, for example in conjunction with an amniotic fluid incubator system. In some embodiments, the artificial placenta substantially matches the performance of native placenta, to control or replace several organ systems on an as needed basis. In addition, in some embodiments, the artificial placenta retains the fetal circulation to bypass the developing lungs. In some embodiments, this artificial placenta can partially take over gas exchange function until the infant recovers from the initial cause of the lung incompetence during the early postnatal period. In some embodiments, this device can be applied to the newborn in conjunction with other forms of respiratory support. In some embodiments, the additional extracorporeal gas exchange can improve survival rates of preterm and term newborns with respiratory failure when mechanical ventilation is insufficient. Further, in some embodiments, the artificial placenta can decrease the occurrence of chronic lung disease by reducing the amount of mechanical ventilation, which can especially benefit early preterm infants.

In some embodiments, the artificial placenta mimics the function of the native placenta in totality, decrease mortality of extremely preterm infants, and eliminate the short and long term survivor morbidity, making it a better proposition to the current standards of neonatal care.

In some embodiments, the artificial placenta can be defined by four characteristics: 1) maintenance of fetal circulation and recreation of the intrauterine environment including a low partial pressure of oxygen; 2) lack of mechanical ventilation; 3) simulated fetal breathing with fluid-filled lungs; and 4) incorporation of either AhV or VV-ECLS. One major obstacle to current use of extracorporeal support in premature babies, is the elevated risk of intracranial hemorrhage with heparinzation, which can be addressed in some embodiments with a fifth element of the AP, nonthrombogenic surfaces requiring little to no heparin.

As such, in some embodiments, the systems, methods, and devices described herein are related to extra-uterine support devices (EUSDs) and/or Ex-Vivo uterine Environments (EVEs). Oxygenating assemblies for artificial placenta systems, methods, and devices, such as those described in some embodiments herein, may generally comprise permeable gas membranes combined with a vascular network. Some embodiments of the artificial placenta and amniotic bed systems, methods, and devices are configured to maintain a flow of oxygenated blood into a fetus and a flow of carbon dioxide out of a fetus, during a period in which the fetal lungs are not ready to fully or even partially function. Some assemblies comprise modular systems that may require assembly prior to use. In some embodiments, modular systems require combining placental devices in parallel or series, which can lead to unwanted pressure drops. In some embodiments, assembling, disassembling, and/or reassembling connections may require complex processing on-site, which requires time, energy, and expertise, and may cause maintenance issues or introduce user error. Furthermore, dead volume within the system is potentially compounded during oxygenator assembly, disassembly, and/or reassembly of the system.

To address these issues, some embodiments described herein comprise an entire, all-in-one, self-contained oxygenating assembly system that may not require on-site assembly. Some embodiments herein are related to an extracorporeal life support system using a membrane oxygenation system in an extra-uterine setting. In some embodiments, the system inputs and/or outputs are connected to vessels in the subject's umbilical cord. In other embodiments, the system's inputs may be connected through vessels on or in other parts of the subject's body, including, for example, the neck, the mouth, the arm, or any other body part. Some embodiments herein are directed to artificial womb system and/or placenta. Some embodiments herein are directed to an artificial enclosure that mimics the womb whereby the subject is encased, submerged, or partly submerged in amniotic fluid. Some embodiments described herein are directed to 'plug-and-play' artificial placenta systems, method, and devices that allow for the administration of oxygenated blood and/or nutrients through an infant's umbilical cord ready for practical use in hospitals.

In some embodiments, the devices, systems, and methods described herein relate in some aspects to an artificial placenta. In particular, some embodiments relate to an artificial placenta that may receive blood from a preterm infant's umbilical cord and/or return treated blood to a preterm infant's umbilical cord. Although certain embodiments of the artificial placenta is illustrated and described in the context of being useful for preterm infants, the same and/or other embodiments can be useful in other instances, such as for non-preterm infants.

In some embodiments, the systems, methods, and devices are designed to support oxygen and carbon dioxide exchange of neonates including: term, preterm, very preterm and extremely preterm infants (extreme low body weight). In some embodiments, the subjects of the systems, devices, and methods described herein may range between about 22 to 40 weeks of gestational age. In some embodiments, the artificial placenta may be designed to support preterm, very preterm, and/or extremely preterm infants that do not have ability to use lungs in full capacity The systems, methods, and devices described herein provide a solution to the shortcomings in earlier systems for providing an artificial placenta. Some embodiments herein provide a non-invasive means to preserve the life of, for example, premature infants. For example, in many premature infants, the baby's lungs are severely immature and they cannot provide the brain, heart, and/or other organs the oxygen they need to survive. The systems, methods, and devices described herein may maintain fetal circulation and provide a normal partial pressure of oxygen thereby avoiding potentially harmful mechanical ventilation to the lungs. The systems, methods, and devices described herein can receive low-oxygen, venous blood from, for example, the umbilical cord of a preterm infant, sequester carbon dioxide and oxygenate the blood by means of a membrane oxygenator that delivers the oxygenated blood back to the preterm infant through the umbilical cord. In some embodiments, an artificial placenta can comprise a capillary tree system configured to deliver blood to one or multiple membrane oxygenators (e.g. semi-permeable hollow fibers capable of oxygenating a preterm infant's blood passing there through).

In some embodiments, the devices, systems, and methods described herein are directed to an artificial placenta. In particular, in certain embodiments, an artificial placenta can receive arterial blood from the umbilical cord of a preterm infant, oxygenate the blood, and/or deliver the oxygenated blood back to the preterm infant through the umbilical cord.

In certain embodiments, an artificial placenta can receive arterial blood from the umbilical cord of a preterm infant, oxygenate the blood and/or deliver nutrients to the blood, and/or deliver the oxygenated and/or nutrient rich blood back to the preterm infant through the umbilical cord.

In some embodiments, an artificial placenta as described herein is configured to be used for an infant that is partially submerged in simulated amniotic fluid and/or in combination with a simulated amniotic fluid injection system that fills the lungs of the infant with simulated amniotic fluid. For example, in some embodiments, an infant is placed in an amniotic fluid bath or bed such that the body of the infant is submerged in simulated amniotic fluid, while the head of the infant is maintained above the fluid level of the simulated amniotic fluid. In some embodiments, simulated amniotic fluid is injected into the lungs of the infant through the nose and/or mouth of the infant. In some embodiments, an artificial placenta system provides all of the oxygenation for the infant whose lungs are filled with simulated amniotic fluid and/or not fully developed. In some embodiments, a hybrid approach can also be possible, wherein once the lungs of the infant are developed or partially developed, some level of oxygen can be provided to the infant through the lungs of the infant while at the same time some level of oxygen can be provided to the infant through the artificial placenta system. In some embodiments that allow such hybrid processes, the artificial placenta system can comprise an oxygen level sensor that detects and thereby controls the level of oxygenation to be provided to the infant through the artificial placenta system.

In some embodiments, an artificial placenta can comprise a capillary tree system configured to deliver blood to one or multiple semipermeable hollow fibers capable of oxygenating a preterm infant's blood passing there through. In some embodiments, the capillary tree and/or hollow fiber(s) does not include any sharp edges to prevent damaging red blood cells.

Some embodiments herein provide an infant with hydration and nutrients. As described herein, various forms of nutrients and fluids may also be administered at various points within the system. For example, a nutrition disposable cartridge of predetermined volume can contain, for example, dissolved nutrients that can be delivered, via the systems, methods, and devices, described herein, into the bloodstream via an arterial line into, for example, the umbilical cord of the infant. In some embodiments, the arterial line delivers blood from arterial blood vessels (e.g. through the umbilical cord) to a gas exchange unit's (i.e. gas exchanger's) inflow capillary unit via, for example, two umbilical arterial catheters. In some embodiments, blood pressure, temperature, and blood reservoir level are continuously measured within the arterial line. In some embodiments, the design of the arterial line enables separation of the patient's blood in terms of blood pressure. In some embodiments, blood inflow from arteries is collected in a blood reservoir (e.g. bladder), thus effectively separating patient side and device side blood pressure.

In some embodiments, an artificial placenta system can comprise a three-prong catheter system further comprising two umbilical arterial catheters and one umbilical vein catheter. In some embodiments, the artificial placenta system can comprise an anchor for maintaining the location of the catheters above the fluid level, for example when in use with an infant whose body is submerged in simulated amniotic fluid while the head of the infant is maintained above simulated amniotic fluid, for example to prevent contamination of the catheter. In some embodiments, the artificial placenta system can comprise a water-sealing or water-tight cover around where the catheter is connected to the umbilical cord, for example to prevent contamination.

In some embodiments, the artificial placenta system comprises one or more sensors for detecting the flow of blood through the artificial placenta system. For example, in some embodiments, if the flow of blood through the artificial placenta system is detected to be below a predetermined level, an alarm may automatically be triggered to notify a health care provider. In some embodiments, if the flow of blood through the artificial placenta system is detected to be below a predetermined level, a ventilation machine can be automatically triggered to mechanically pump oxygen and/or air through the nose and/or mouth of the infant into the lungs. For example, in embodiments in which the lungs of the infant are filled with simulated amniotic fluid, the simulated amniotic fluid in the lungs of the infant can be flushed out with the oxygen and/or air that is pumped into the lungs of the infant in case the flow of blood through the artificial placenta system is detected to be below a predetermined level.

The systems, methods, and devices herein may allow health care providers to monitor and control all aspects of an artificial placenta. In some embodiments, the artificial placenta may considered to be a 'turn-key' solution that can be installed inside a maternity ward and/or hospital that can be managed by users, including, for example, doctors, nurses, and/or medical staff. The artificial placenta may include a plurality of sensors that continuously measure, for example, fluid and gas temperatures, pressures, and/or flow rates to ensure parameters are within pre-determined thresholds. In some embodiments, a controller may be connected to a human-machine interface (e.g. a dynamic user interface, graphical user, etc.). In some embodiments, the human-machine interface may incorporate various input devices, including, for example, a touch screen highlighting key values in real time, including, for example, alarms for parameters that exceed healthy ranges. In some embodiments, the controller and/or human-machine interface may comprise wireless capabilities to securely transmit data in real time to local, regional, global, and/or cloud networks for local and/or remote medical collaborations.

Artificial Placenta and Amniotic Bath

FIG. 1 is schematic diagram of an example embodiment of the artificial placenta and amniotic bed system according to various embodiments herein. Some embodiments of the artificial placenta and amniotic bed system described herein are configured to connect to an infant through umbilical blood vessels. In some embodiments, unlike adults, infant umbilical arteries carry blood with relatively low oxygen levels, whereas infant umbilical veins carry blood with relatively high levels of oxygen. In some embodiments, an artificial placenta and amniotic bed system 100 is designed to replace one or more of the functions of a natural placenta. For example, in some embodiments, the artificial placenta and amniotic bed system 100 may be connected to a preterm infant 105 and/or may serve to oxygenate the preterm infant's blood. In some embodiments, the infant 105 may be disposed in an amniotic bed 400 containing, for example, simulated amniotic fluid 395 therein. In some embodiments, the artificial placenta and amniotic bed system 100 comprises a gas exchanger 110 into which the infant's arterial blood may enter via of one or more arterial lines 125 (also referred to as umbilical catheters) and one or more gas exchanger inlet(s) 130. In some embodiments, as described herein, the gas exchanger 110 may be configured to oxygenate the arterial blood. In certain embodiments, the oxygenated blood can be administered to the infant 105 as venous blood after passing via a gas exchange outlet 140 and one or more umbilical vein catheters 135. In some embodiments, as illustrated in FIG. 1, the infant's umbilical cord 120 may be used to both collect arterial blood and to reintroduce venous blood. In some embodiments, one or more arterial lines 125 can be connected at one end to the umbilical cord 120 and the other end can be connected to one or more gas exchanger inlet(s) 130 into the gas exchanger 110. In some embodiments, one or more venous lines 135 connects an outlet 140 out of the gas exchanger 110 to the umbilical cord 120. However, in some embodiments, the one or more arterial lines 125 and/or one or more venous lines 135 may connected intravenously at any location on an infant's body.

In some embodiments, the venous line delivers blood from gas exchanger's outflow capillary unit to a venous blood vessel (e.g. through the umbilical cord) via, for example, a venous umbilical catheter. In some embodiments, the venous umbilical catheter is connected to a vein in the umbilical cord of the infant. In some embodiments, a bubble trap along the venous line may comprise a bubble trap to remove bubbles in the venous line. In some embodiments, there is a bubble detector located along the venous line to alert the system to presence of bubbles within the blood in the venous line. In some embodiments, blood pressure, temperature, oxygenation, and blood flow level are continuously measured within the venous line. In some embodiments, the venous line is equipped with a Luer port for direct pharmaceuticals administration into the oxygenated blood. In some embodiments, the design of the outflow capillary unit enables separation of the patient's blood in terms of blood pressure. In some embodiments, blood outflow from the outflow capillary unit is collected in the bubble trap, effectively separating patient side and device side blood pressure. In some embodiments, blood is delivered into umbilical cord vein via gravity flow by maintaining hydrostatic pressure equivalent to body vein pressure that enables blood flow into an umbilical cord vein.

Further, in some embodiments, as in the illustrated embodiment of FIG. 1, two arterial lines 125 are provided. In some embodiments, one arterial line 125 may be provided. In some embodiments, 1, 2, 3, 4, 5, 6, 7, 8, 9, or 10 arterial lines may be provided in the artificial placenta and/or amniotic bed system.

The arterial lines 125 may comprise, but are not limited to, two umbilical arterial catheters connected to two umbilical arteries at a cut end of the umbilical cord 120. The umbilical cord 120 of the infant 105 may be cut at a distance of, but not limited to, the current medical standard of 5 cm from the abdominal wall or cut at 6 cm, 10 cm or a longer length and maintained at a warm temperature to prevent solidification of Wharton's jelly in the umbilical cord 120. In some embodiments, the umbilical cord 120 of the infant 105 can be cut at a distance of about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 20 cm, about 25 cm, or any distance between two of the aforementioned values.

In some embodiments, the catheters can be placed using, for example, a clamp that is connected to a bridge. In some embodiments, the bridge can be connected to a fixed surface (e.g. incubator, amniotic bed, etc.). Along with the clamp, a water tight sleeve can be placed, for example, 2-3 cm below the umbilical cord cut (length of cord may be about 10 cm when cut). In some embodiment, the sleeve is wrapped so it does not interfere with the catheterization procedure.

In some embodiments, a guidewire can be inserted with a plug into the umbilical blood vessel at a depth of, for example, 2-5 cm. In some embodiments, the guidewire comprises a gauge for measuring the depth in, for example centimeters. In some embodiments, when the guidewire reaches a predetermined depth, the non-primed catheter can be emptied from the sleeve by sliding via a guidewire path (wherein the guidewire is inside the catheter hole). In some embodiments, the guidewire is longer than the catheter by, for example, 20 cm or more.

In some embodiments, when the catheter slides down, prior to entering umbilical vessel, the guidewire end is freed and fixed to prevent accidental sliding of the guidewire from the vessel. The catheter can be pushed through the guidewire path until it reaches a predetermined insertion depth. The insertion depth can be determined by a plug on the end of guidewire (i.e. part of guidewire inside a vessel). In some embodiments, the guidewire's free end is released from the fixture to allow for the guidewire to be pulled out. In some embodiments, the catheter is held in place (e.g. at a maximum depth) by hand, while another hand holds the free end of the guidewire. In some embodiments, the guidewire is pulled out of umbilical vessel through the catheter hole.

The plug may be designed to completely seal internal walls of the catheter during the pulling out procedure. By doing so, the plug may act as a piston which sucks blood in the catheter from the umbilical vessel on lower side of the plug. At the same time, the plug may push air out of catheter on upper side of plug. In this way, the catheter may be primed with blood from an umbilical blood vessel.

A variation to this procedure is to use a primed catheter, which can be drained during the procedure. Despite draining, the catheter may stay wet and decrease friction during the pulling out of guidewire. In some embodiments, the catheter is primed with the patient's blood without danger of air bubbles being left in catheter.

In some embodiments, all the catheters described herein can be placed in the manners described herein (e.g. one vein and two arterial catheters). In some embodiments, the catheter can be a three-prong catheter comprising one umbilical vein catheter and two umbilical arterial catheters. In some embodiments, the clamp with the watertight sleeve can be secured to the umbilical cord to prevent fluid contacting any tissue near the cut (i.e. location where the umbilical cord is cut). In some embodiments, the watertight sleeve can comprise plastic or other water-sealing material. In some embodiments, the clamp also holds the catheters in place. In some embodiments, the catheters are secured (i.e. fixed) to a bridge so that the catheters remain in a relatively fixed position relative to the umbilical cord cut. In some embodiments, the clamp is secured to a bridge, which is fixed to the incubator or amniotic bed. In some embodiments, the catheter can be configured to be used in conjunction with an anchor that maintains the location of the catheter above the fluid level, for example when used for an infant whose body is submerged in synthetic amniotic fluid but whose head is maintained above the fluid level. As such, the location of the catheter can be maintained in some embodiments to never be placed under or in the synthetic amniotic fluid to prevent contamination and/or the need to replace the catheter due to contamination.

In some embodiments, the sleeve may be unwrapped so it covers the clamp, catheters and bridge, which may prevent any contamination of the umbilical cord cut or any tissue contamination. In some embodiments, this configuration prevents the catheters from being pulled out from umbilical vessels, as the catheters are secured to the bridge and the clamp holding the catheters is also connected to a bridge, such that any pulling or pushing force that would move catheters out of their place in vessels will transfer to the bridge rather than produce relative movement (i.e. displacement of catheters in relation to the umbilical cord and thus displacement from blood vessels). This decreases the possibility of catheter displacement and need for recatheterization.

The procedures described herein may comprise placing the newborn infant 105 within simulated amniotic fluid 395 of an amniotic bed device 400, such as The Amniotic Bed by Amnion Life and described in U.S. Pat. No. 9,662,257. In some embodiments, the procedures, methods, devices and systems herein can be used independently or in combination with any air controlled incubator. In some embodiments, the arterial line(s)' umbilical catheters 125 are advanced within the umbilical arteries for a distance of 1 cm, 2 cm, or to the level of the umbilicus and anchored in place by means known by those skilled in the art, such as, for example, clamps. In some embodiments, the arterial lines 125 are advanced within the umbilical arteries for a distance of about 0.25 cm, about 0.50 cm, about 0.75 cm, about 1.00 cm, about 1.25 cm, about 1.50 cm, about 1.75 cm, about 2.00 cm, about 2.25 cm, about 2.50 cm, about 2.75 cm, about 3.00 cm, about 3.25 cm, about 3.50 cm, about 3.75 cm, about 4.00 cm, about 4.25 cm, about 4.50 cm, about 4.75 cm, about 5.00 cm, or any distance between two of the aforementioned values.

As shown in FIG. 1, the aforementioned one or more arterial line(s) 125 may connect to one or more gas exchange inlet(s) 130 into the gas exchanger 110 and join within the gas exchanger 110 and/or pass through separate circuits within the gas exchanger 110 and join on the venous side. The one or more umbilical vein catheter(s) 135 may deliver blood from the gas exchanger 110 to the umbilical vein on the cut end of the umbilical cord 120 for a distance of about 1 cm, about 2 cm, or further advanced through the umbilicus, umbilical vein, left portal vein, ductus venous, middle or left hepatic vein, and into the inferior vena cava. In some embodiments, the venous lines 135 are advanced within the umbilical cord for a distance of about 0.25 cm, about 0.50 cm, about 0.75 cm, about 1.00 cm, about 1.25 cm, about 1.50 cm, about 1.75 cm, about 2.00 cm, about 2.25 cm, about 2.50 cm, about 2.75 cm, about 3.00 cm, about 3.25 cm, about 3.50 cm, about 3.75 cm, about 4.00 cm, about 4.25 cm, about 4.50 cm, about 4.75 cm, about 5.00 cm, or any distance between two of the aforementioned values.

In some embodiments, venous line(s)' 135 umbilical vein catheter is anchored in place. In some embodiments, blood pressure, temperature, and/or other physical or chemical properties of the venous blood may also be monitored, as described herein. In some embodiments, one or more additional accessories, such as a bubble trap, a bubble detector, and/or a Luer port (i.e. port, lock) for pharmaceutical administration may also be associated with the one or more venous line(s).

In some embodiments, the artificial placenta and amniotic bed system may also comprise a gas delivery unit 155. In some embodiments, the gas delivery unit 155 may be in communication 160 with the interior of the gas exchanger 110. In some embodiments, the gas delivery unit 155 can be configured to supply a gas mixture—such as, but not limited to oxygen and the like, to the gas exchanger 110 at a predetermined pressure and/or temperature. In some embodiments, gas may be pressurized by an air pump (e.g. a vane pump, diaphragm pump, etc.), by a hospital's existing air and oxygen supply, and/or by external gas tanks. In certain embodiments, a heater and/or heat exchanger may heat the gas to the predetermined temperature before entering the gas exchanger 110. In some embodiments, the gas may be filtered for impurities, and the gas pressure may be regulated by, for example, control valves. In some embodiments, a control unit 165, as described further below, monitors and controls the gas delivery unit 155 components and/or the gas exchanger 110 components therein. For example, in certain embodiments, temperature and gas flow rates are constantly monitored with sensors and can be altered automatically using control unit 165. In some embodiments, a human-machine interface 170 allows a user to interface, monitor, and give commands to the control unit 165 by means of one or more input/output devices, such as a touch screen interface. In some embodiments, the control unit 165 may comprise a multitude of devices such as, but not limited to: a programmable logic controller (PLC) linked to sensors and components within the gas delivery unit 155, gas exchanger 110, and fluids delivery unit 250 (shown in FIG. 6) and networked to, for example, a computer having a graphical user interface herein referred to as human machine interface 170. In some embodiments, the human machine interface 170 may comprise proprietary software therein allowing a user to monitor and control the various components described herein.

In some embodiments, gases (e.g. oxygen and air) are supplied to the gas delivery unit from a hospital's central gas delivery system through, for example, a wall mount. The wall mounts may be connected to inlet gas connectors of the gas delivery unit. Alternatively, oxygen and air can be delivered from external gas tanks connected to the inlet gas connectors. In some embodiments, gases are mixed in a blender and a mixing ratio of oxygen and air are controlled by control valves. In some embodiments, a filter prevents impurities from entering the gas in the system. In some embodiments, gas temperature is maintained at a desired or required value with heater and valves, which may mix gases of different temperatures in required proportions to effect the temperature changes. In some embodiments, condensate removing is realized by a condenser located in the gas delivery unit. In some embodiments, gas temperature is constantly measured by a temperature sensor and gas pressure is constantly measured by pressure sensor. In some embodiments, a gas analyzer continuously measures gas components (e.g. 02 fraction). In some embodiments, gas pressure in the gas exchanger jacket is also regulated with control valves. In some embodiments, gas is transported through the artificial placenta device's internal tubing to the wall mount connector. In some embodiments, gas flow rate is continuously measured with a flow meter. In some embodiments, downstream of connector may be disposable tubing used to deliver gas to the gas inlet of the gas exchanger. After passing through the gas exchanger, gas may flow through, for example, disposable tubing back into gas delivery unit through a wall mount connector. In some embodiments, a gas analyzer is used for continuous measurements of the used gas components. In some embodiments, gas may be discharged into atmosphere through a strainer.

Figure 5A:
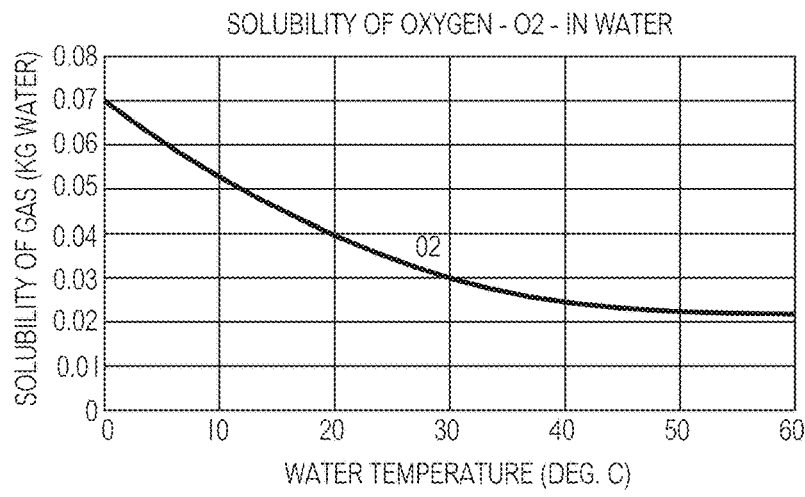
FIG. 5A is a graph showing the solubility of O2 in water.
Figure 5B:
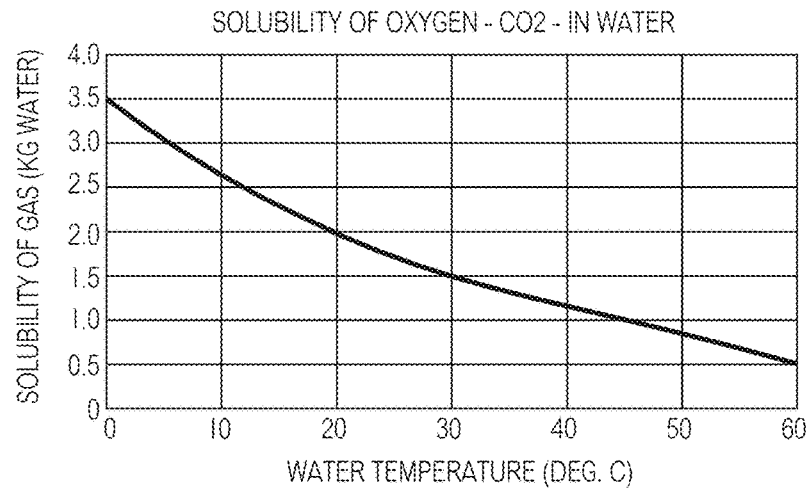
FIG. 5B is a graph showing the solubility of CO2 in water.
Figure 5C:
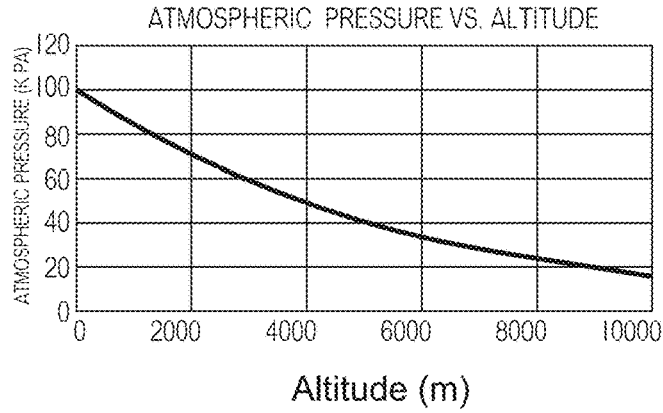
FIG. 5C is a graph showing atmospheric pressure vs. altitude.
Figure 5D:
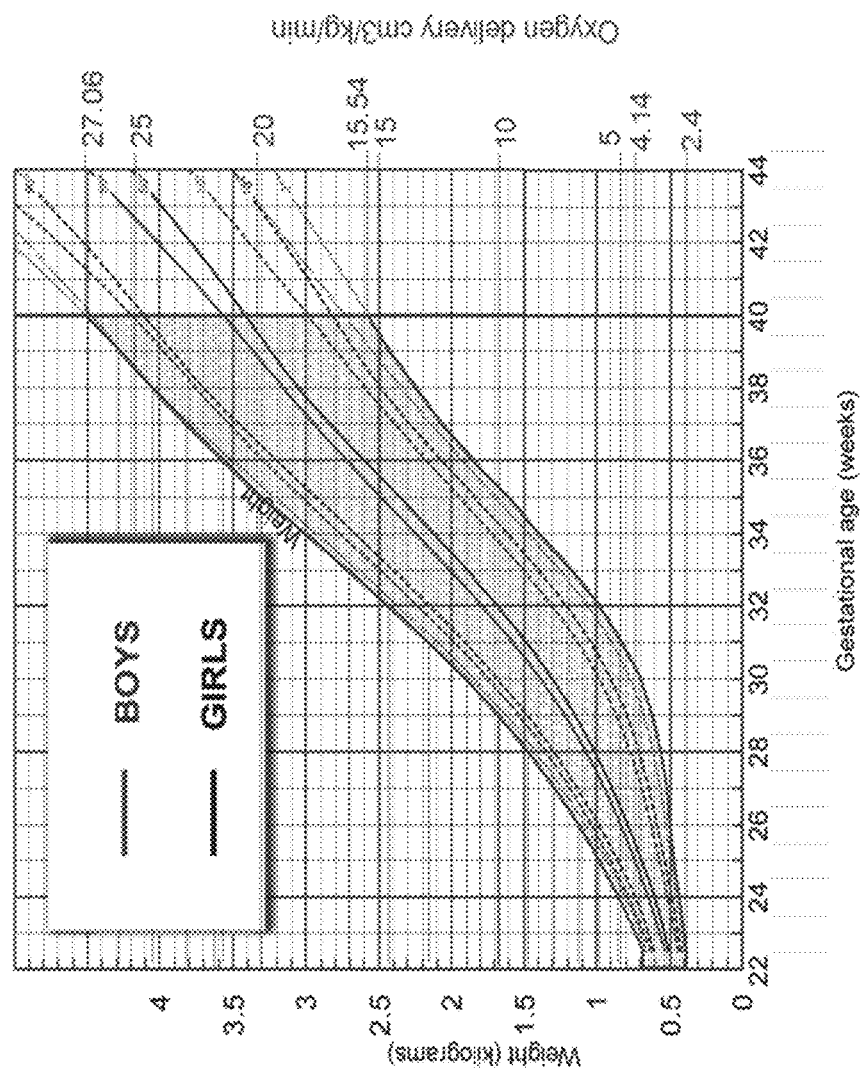
FIG. 5D is a graph showing oxygen delivery and weight vs. gestational age.

In some embodiments, the partial pressures of an air and oxygen mixture may be regulated with control valves to reach optimum O2 saturation according to, for example, the diagram shown in FIG. 5D.

In some embodiments, blood pump 260 may used to recirculate blood through the gas exchanger in order to increase oxygenation. In some embodiments, a backflow preventer 367 may be used along the recirculation path. In some embodiments, the pump 269 may have higher capacity than blood pump 260. In some embodiments, the difference may be equal to a system-determined patient need for blood flowrate. In some embodiments, a single pump 269 is used while flow from reservoir 364 to bubble trap 350 may be achieved by positioning tanks to produce hydrostatic pressure, thus enabling gravitational blood flow.

In some embodiments, the artificial placenta may comprise one or more pinch valves that can be used to quickly replace a defective gas exchanger with a new one. The pinch valves may be configured to allow the temporary disruption of blood flow through the gas exchanger.

In some embodiments, the artificial placenta comprises a venous blood bubble trap comprising a blood filter, the blood bubble trap configured to separate gas bubbles from blood and filter the blood. In some embodiments, the artificial placenta further comprises a bubble detector configured to detect gas bubbles in blood, which may occur because of breaches of the bubble trap or other reasons (e.g. a sudden pressure drop after the trap). In some embodiments, if a gas bubble is detected in the blood, an oxygenation failure procedure can be initiated by the control unit.

In some embodiments, pressure of blood in the system is continuously measured with pressure sensors. In some embodiments, temperature of blood in the system is continuously measured with temperature sensors. In some embodiments, blood oxygen saturation level is continuously measured with one or more $SvO_2$ sensors. If the blood oxygen saturation level drops below defined values in the venous line, oxygenation level may be increased by increasing pressure in the gas exchanger and/or by increasing the $O_2$ fraction in the infiltration gas mixture. If the SvO2 level measured with SvO2 sensor is not increased in a predefined limit of time, an oxygenation failure procedure can be initiated by the control unit. In some embodiments, one or more flow meters continuously monitor blood flow rate throughout the artificial placenta. In some embodiments, in the case that blood flow rate drops below a minimum required flow rate, an oxygenation failure procedure can be initiated by the control unit. In some embodiments, the venous line is equipped with Luer port for direct pharmaceuticals administration into the blood.

An oxygenation failure procedure may comprise audio alarm sounds and/or visual alarms, which can be displayed on the human machine interface. In some embodiments, gas flow paths can be closed by various valves in the system. In some embodiments, the blood flow paths can be closed by various valves in the system. In some embodiments, the gas exchanger may be depressurized with various valves in the system. In some embodiments, heaters within the system can be halted. In some embodiments, gas and fluid pumps within the system may be halted. In some embodiments, the artificial placenta's control unit may display, through the human machine interface, readings from all sensors and may display instructions to an operator about possible solutions determined by the system.

Gas Exchanger

Figure 2A:
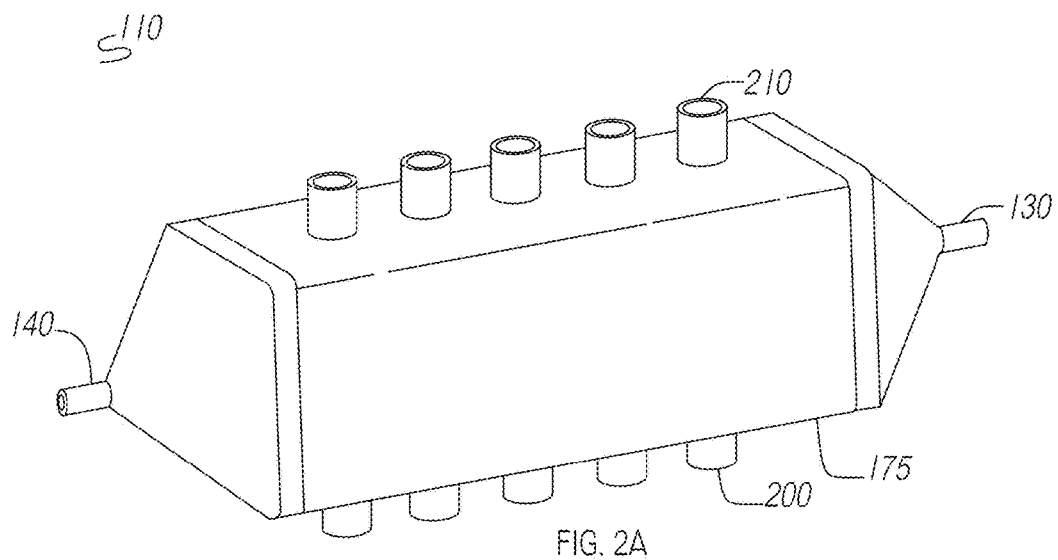
FIG. 2A is a schematic perspective view of an example embodiment of a gas exchanger according to various embodiments herein.

FIG. 2A is a schematic perspective view of an example embodiment of a gas exchanger according to various embodiments herein. In some embodiments, the gas exchanger 110 mimics the blood-gas exchange that occurs in a natural placenta. In some embodiments, for example, like a natural placenta, the gas exchanger 110 may comprise a membrane exchanger. In certain embodiments, the gas exchanger 110 comprises an outer shell 175 having a substantially rectangular shape. In other embodiments, the outer shell 175 of the gas exchanger 110 may comprise any suitable shape, including, for example, cylindrical, trapezoidal, cubical, spherical, triangular, polyhedral, prismatic, pyramidal, conical, ring-shaped, or otherwise.

The outer shell 175 of gas exchanger 110 may comprise a rigid material such as, but not limited to plastic, metal, or the like. The gas exchanger 110 may comprise one or more gas exchanger inlet(s) 130 on the outer shell 175 of the gas exchanger 110. In some embodiments, such as that shown in FIG. 2A, the one or more gas exchanger inlet(s) 130 may be located on an end of the gas exchanger 110. In other embodiments, the one or more gas exchanger inlet(s) 130 may be located on a side of the gas exchanger 110. The one or more gas exchanger inlets may be configured for receiving arterial blood from the one or more arterial line(s) 125.

In some embodiments, the outer shell 175 of gas exchanger 110 may comprise one or more gas exchanger outlet(s) 140 on an opposite end of the gas exchanger from the one or more gas exchanger inlet(s) 130. In some embodiments, the one or more gas exchanger outlet(s) 140 may be located on the same end as the one or more gas exchanger inlet(s) 130 or may instead be located on a side of the gas exchanger 110. In some embodiments, the one or more gas exchanger outlet(s) 140 may be configured for discharging or outputting blood from the gas exchanger 110 to the one or more venous line(s) 135.

Figure 2B:
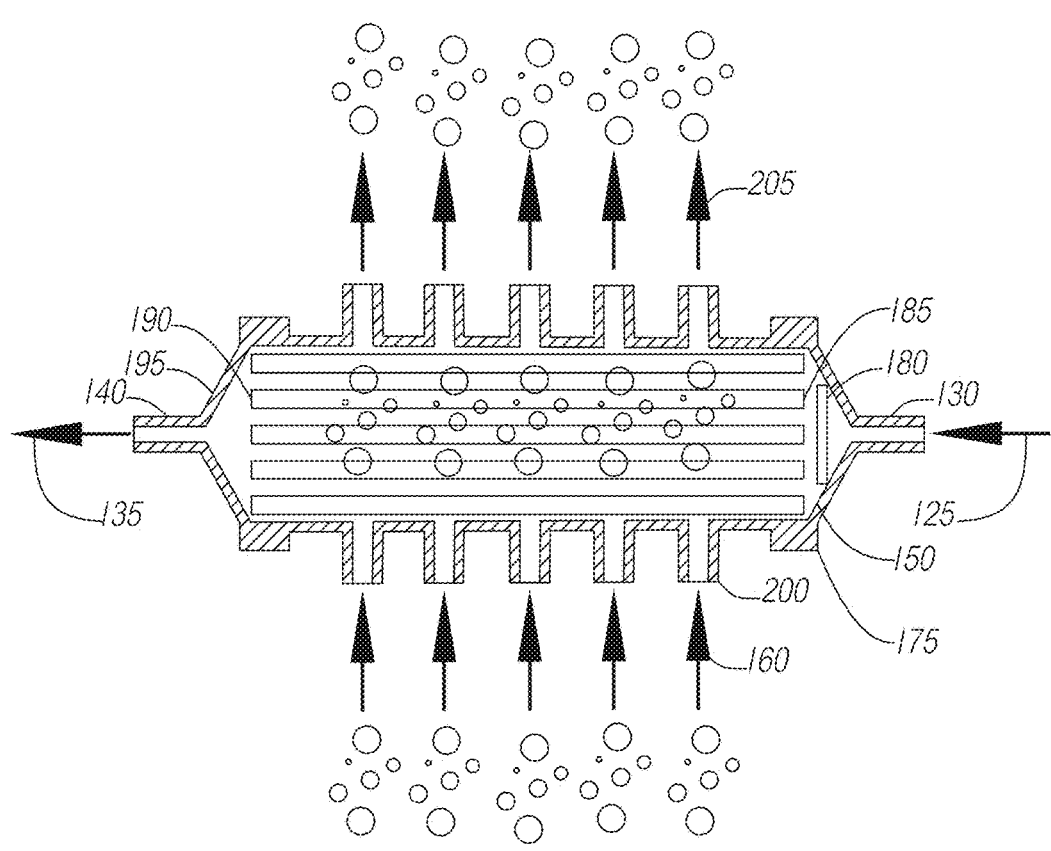
FIG. 2B is a schematic sectional view of the example gas exchanger of FIG. 2A according to various embodiments herein.

In some embodiments, arterial blood enters through one or more inlet(s) 130. In some embodiments, the blood is delivered, within the gas exchanger 110, to an inflow capillary tree 180, as shown in FIG. 2B. In certain embodiments, the inflow capillary tree 180 comprises one or more feed arteries that branch through several branching iterations to create, for example, several hundred or more sub-branches, as described herein. In some embodiments, the one or more feed arteries may branch to create 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 branches and/or sub-branches, or any multiple of the aforementioned number of branches and/or sub-branches, or any value between two of the aforementioned number of branches and/or sub-branches. In some embodiments, the capillary tree does not comprise any sharp edges to prevent breaking down of red blood cells.

In some embodiments, the arterial blood can be delivered to a hollow fiber unit 185 disposed, for example, along the longitudinal axis of gas exchanger 110. In the some embodiments, the gas exchanger 110 may comprise different shapes which may necessitate different orientations of the hollow fiber unit 185. For example, the hollow fiber unit 185 may be disposed along a radial axis, along an arcuate path, along a vertical or horizontal axis of the gas exchanger 110, or in any other suitable orientation according to the shape and size of the gas exchanger 110. In some embodiments, the hollow fiber unit does not comprise any sharp edges to prevent breaking down of red blood cells.

In some embodiments, the hollow fiber unit 185 comprises hydrophobic polymers such as, but not limited to, polypropylene. In certain embodiments, each sub-branch from the inflow capillary tree 180 is connected to one or multiple hollow fibers 190. In some embodiments, one end of the hollow fibers 190 can be potted (i.e. anchored or secured) on the inflow capillary tree 180 and the opposite end can be potted on an outflow capillary tree 195. In some embodiments, nine hollow fibers 190 are potted onto each sub-branch of the inflow capillary tree 180 and to a corresponding sub-branch in the outflow capillary tree 195. In some embodiments, 1, 2, 3, 4, 5, 6, 7, 8, 9, 10, 11, 12, 13, 14, 15, 16, 17, 18, 19, 20, 21, 22, 23, 25, 26, 36, 49, 64, 81, 100, 121, 144 hollow fibers, or any number of hollow fiber between two of the aforementioned values, can be potted onto each sub-branch of the inflow capillary tree 180 and/or the outflow capillary tree 195. In some embodiments, each pot or cubicle (i.e. end of branching of capillary three) ends with 9 hollow fibers arranged in a 3×3 array. In some embodiments, the number of hollow fibers of each cubicle enables equidistant design of the membrane. In some embodiments, each array or group of hollow fibers is located at a substantially same distance to each other and may be parallel (i.e. relatively equidistant) to each other. In some embodiments, each hollow fiber of the hollow fiber unit is located at a substantially same distance to each adjacent hollow fiber and may be parallel to each adjacent or neighboring hollow fiber. In some embodiments, this enables equal distribution of gas and uniform gas exchange to each hollow fiber, thus increasing performance of the gas exchanger. In some embodiments, the equidistant design enables superior gas exchange performance with minimum priming blood volume (e.g. 30 ml or 15 ml or less depending on configuration).

In some embodiments, each cubicle (i.e. end of branching of capillary three) ends with 9 (or another number enabling equidistant design of the membrane) hollow fibers. In some embodiments, each group of 9 hollow fibers is located at the same distance from each other and is oriented parallel (i.e. relatively equidistant) to each other. In some embodiments, each group of 9 hollow fibers is located at substantially the same distance and substantially parallel to every other group of 9 HFs. This enables equal distribution of gas and uniform gas exchange to each hollow fiber, thus increasing performance.

In certain embodiments, the outflow capillary tree 195 can comprise a reverse configuration of the inflow capillary tree 180, wherein oxygenated blood flows from the hollow fibers 190 into the sub-branches of the outflow capillary tree 195. In some embodiments, the sub-branches of the outflow capillary tree 195 gather into one or more branches in an iterative branching arrangement. In some embodiments, the branches further group into one or more venous line(s) 135. In some embodiments, the one or more venous line(s) exit the gas exchanger 110 through one or more gas exchanger outlet(s) 140. In some embodiments, blood is delivered to the one or more venous line(s) 135 via the one or more outlet(s) 140.

FIG. 2B is a schematic sectional view of the example gas exchanger of FIG. 2A according to various embodiments herein. FIG. 2B is a sectional view of the example gas exchanger 110 and its interior 150. In some embodiments, oxygenation and CO2 sequestration of a preterm infant's 105 blood can occur on the interior 150 of the gas exchanger 110.

In some embodiments, the hollow fibers 190 may comprise semi-permeable fibers which can allow for gas exchange across their membranes. Thus, gas exchange may occur as blood flows through the fibers while an infiltration gas 160 flows into one or more inlet passageways 200 and around hollow fibers 190. The infiltration gas 10 may leave the gas exchanger 110 as deoxygenated air 205. The infiltration gas may comprise, for example, oxygen, nitrogen, and other gases. In some embodiments, infiltration gas 160 may be heated and/or oxygenated prior to entering the gas exchanger 110 or while inside the gas exchanger 110. In some embodiments, the infiltration gas may enter gas exchanger 110 through the inlet passageways 200 and flow around fibers 190 in a perpendicular direction to the flow of blood such that the infiltration gas 160 can be exchanged across the hollow fiber's 190 semipermeable membrane therein. In some embodiments, the inlet passageways 200, hollow fibers 190 and infiltration gas 160 may be oriented such that the infiltration gas flows in a parallel direction or other angle (e.g. acute, obtuse, etc.) to the flow of the blood through the hollow fibers 190.

In some embodiments, deoxygenated air 205 can flow out of the gas exchanger 110 through one or more outflow passageways 210. In some embodiments, gas properties, such as temperature and pressure, outside and within gas exchanger 110 may be monitored continuously and controlled via a controller, as discussed herein. In some embodiments, the gas exchanger 110 may also be provided with a several failsafe mechanisms, including, for example, a blood leak detector. In some embodiments, the blood leak detector may be configured to be triggered if a threshold amount of blood is determined to leak from the capillary trees and/or hollow fibers within the gas exchanger 110. In some embodiments, the blood leak detector may be configured to trigger an alarm and/or initiate a response mechanism if a blood leak of more than, for example about 1 to 2 ml is detected. In some embodiments, the blood leak detector may be configured to trigger an alarm and/or initiate a response mechanism if a blood leak of more than, for example, about 0.001 ml, about 0.01 ml, about 0.1 ml, about 0.2 ml, about 0.3 ml, about 0.4 ml, about 0.5 ml, about 0.6 ml, about 0.7 ml, about 0.8 ml, about 0.9 ml, about 1 ml, about 2 ml, about 3 ml, about 4 ml, about 5, ml, about 6 ml, about 7 ml, about 8 ml, about 9 ml, about 10 ml, about 20 ml, about 30 ml, about 40 ml, about 50 ml, about 100 ml, about 200 ml, about 300 ml, about 400 ml, about 500 ml, or about 1000 ml, or any volume between two of the aforementioned volumes is detected.

Figure 3A:
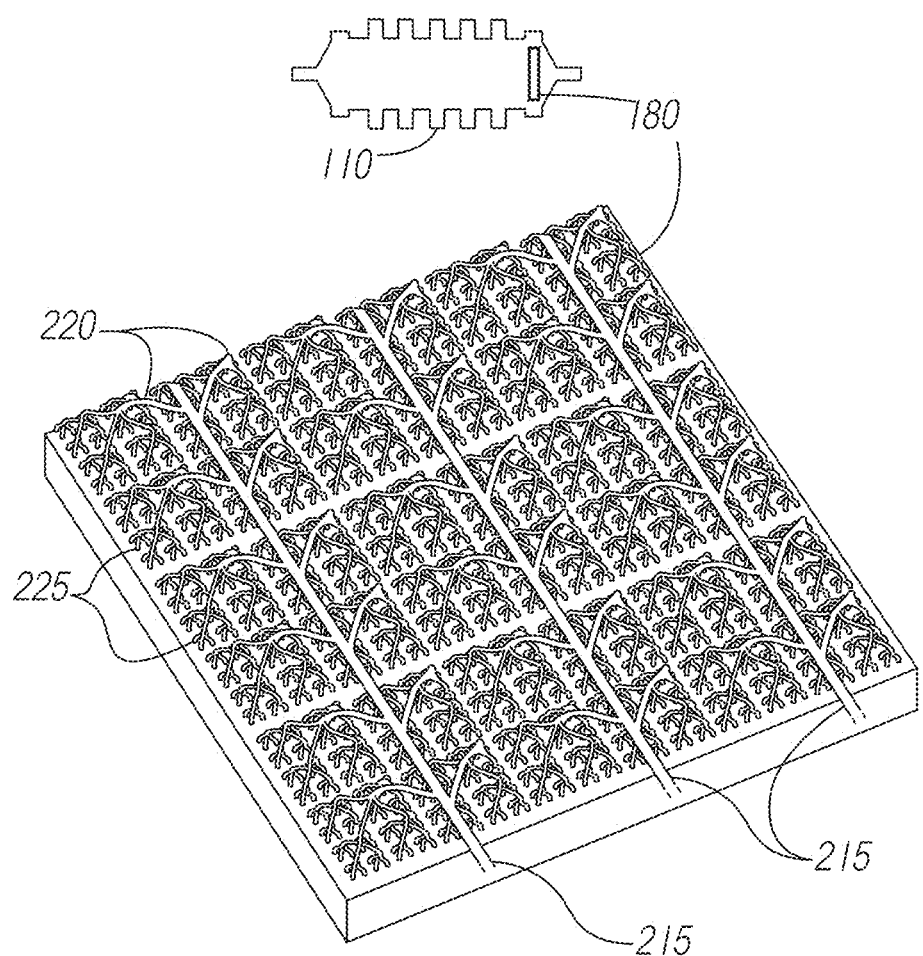
FIG. 3A is a schematic perspective view of an embodiment of an example gas exchanger's capillary tree according to various embodiments herein.

FIG. 3A is a schematic perspective view of an embodiment of an example gas exchanger's capillary tree according to various embodiments herein. FIG. 3A illustrates a perspective view of an example embodiment of the inflow capillary tree 180 and/or outflow capillary tree 195 inside gas exchange unit 110. In some embodiments, the one or more arterial lines 125 comprise one or more main feed arteries 215, which may be rigidly affixed to a substrate comprising the inflow capillary tree 180 thereon. In some embodiments, the inflow capillary tree 180 may be located on the interior 150 of the gas exchanger unit 110. In some embodiments, the inflow capillary tree 180 may be located near an end of the gas exchanger 110, adjacent to the one or more gas exchanger inlets 130.

In some embodiments, the one or more arterial lines 125 may comprise 1, 2, 3, 4, 5, 6, 7, 8, 9, 10, 15, 20, 25, or 50 main feed arteries 215, or any number of main feed arteries 215 between two of the aforementioned values.

In some embodiments, the substrate may comprise a square-shaped rigid material such as, for example, plastic, metal, and the like. In some embodiments, the substrate may comprise a rectangular, triangular, circular, ovular, arcuate, trapezoidal, pentagonal, hexagonal, or octagonal shape, or any other shape which may be fit within the gas exchanger 110.

In some embodiments, the one or more arterial lines 125 comprise one or more umbilical catheters. Each umbilical catheter may comprise a tubular, rigid material such as, for example, plastic compounds. In some embodiments, the arterial lines may supply blood to the one or more feed arteries 215. In some embodiments, each of the one or more feed arteries 215 may be separated into two or more branches 220, thereby forming clusters 225.

In some embodiments each of the one or more feed arteries 215 may be separated into 8 branches 220. In some embodiments, each of more feed arteries 215 may be separated into 2, 3, 4, 5, 6, 7, 8, 9, 10, 11, 12, 15, 16, 18, 20, or 25 branches 220, or any value between two of the aforementioned values.

In some embodiments, the branches 220 of the feed arteries 215 may form 16 clusters. In some embodiments, the branches 220 of the feed arteries 215 may form 1, 2, 3, 4, 5, 6, 7, 8, 9, 10, 11, 12, 15, 16, 18, 20, 24, 25, 28, 30, 32, 40, 50, 64, 81, 100, 200, 300, 400, 500, or 1000 clusters, or any value between two of the aforementioned values In some embodiments, as shown in FIG. 4B, from a central node 230 of each cluster 225, the cluster may be divided further to create additional sub-branches and sub-clusters, as described herein. In some embodiments, the division of branches and/or clusters of branches may continue until the sub-branches are sufficiently small such that they may successfully deliver blood to the hollow fibers 190 potted to the substrate and connected to the inflow capillary tree 180. In some embodiments, the division of branches continues until there are, for example, 256 or 1024 sub-branches. In some embodiments, division of branches continues until there are, for example, 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 sub-branches, or any value between two of the aforementioned values. In some embodiments, the division of clusters may continue until there are, for example, 1, 2, 3, 4, 5, 6, 7, 8, 9, 10, 11, 12, 15, 16, 18, 20, 24, 25, 28, 30, 32, 40, 50, 64, 81, 100, 200, 300, 400, 500, or 1000 sub-clusters, or any value between two of the aforementioned values.

Figure 3B:
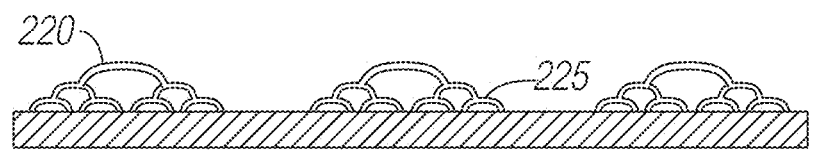
FIG. 3B is a schematic front view of the example capillary tree of FIG. 3A.
Figure 3C:
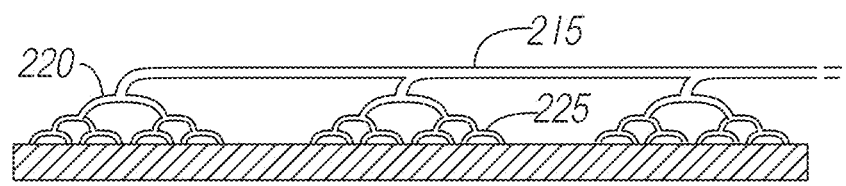
FIG. 3C is a schematic side view of the example capillary tree of FIG. 3A.

FIG. 3B is a schematic front view of the example capillary tree of FIG. 3A. FIG. 3B illustrates a front view of an example inflow capillary tree 180 and/or outflow capillary tree 195 according to various embodiments herein. In some embodiments, the inflow capillary tree 180 and/or outflow capillary tree 195 may comprise clusters 225 and branches 220. FIG. 3C is a schematic side view of the example capillary tree of FIG. 3A. In some embodiments, the inflow capillary tree 180 may comprise one or more feed arteries 215, which may be split into branches and/or clusters of branches as described herein.

FIG. 4A is a schematic perspective view of an example pot grid for connecting sub-branches of a capillary tree with hollow fibers according to various embodiments herein. In some embodiments, the inflow capillary tree 180 and/or outflow capillary tree 195 inside gas exchange unit 110 may comprise an array of pots 245. In some embodiments, one end of each pot of the array of pots 245 may be connected to a hollow fiber of the hollow fibers 190.

In some embodiments, the inflow capillary tree 180 and/or outflow capillary tree 195 may comprise an array of 256 or 1024 pots. In some embodiments, the inflow capillary tree 180 and/or outflow capillary tree 195 may comprise an array of 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 pots, or any value between two of the aforementioned values. In some embodiments, an array of, for example, 256 pots 245 can be provided as shown in the example embodiment of FIG. 4A.

The branching of the inflow capillary tree 180 and/or outflow capillary tree 195 is further shown in the example embodiment illustrated in the sectional view depicted in FIG. 4B. In some embodiments, the inflow capillary tree 180 comprises a feed artery 215 that divides into two or more branches 220, as discussed above. At a cluster central node 230, the branches 220 can divide into two or more first sub-branches 232. In some embodiments, the branches 220 may divide into 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 first sub-branches, or any value between two of the aforementioned values. In some embodiments, the branches 220 divide into 2 or 4 first sub-branches 232.

In some embodiments, the first sub-branches 232 can be further divided. For example, at a second node 234, the first sub-branches 232 can be divided into second sub-branches 236. In some embodiments, the first sub-branches 232 may divide into 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 second sub-branches, or any value between two of the aforementioned values. In some embodiments, the first sub-branches 230 divide into 2 or 4 second sub-branches 236.

In some embodiments, the second sub-branches 236 can further divide at a third node 238 into third sub-branches 240. In some embodiments, the second sub-branches 236 may divide into 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 third sub-branches, or any value between two of the aforementioned values. In some embodiments, the second sub-branches 236 divide into 2 or 4 third sub-branches 240.

The various sub-branches may continue to be divided iteratively until a desired branch size is reached. In some embodiments, ultimately, the sub-branches can reach a final node 242 (e.g. a fourth node as shown in FIG. 4B) where entering sub-branches can divide into the smallest sub-branches 244. Although only four divisions are shown, there can be additional nodes and divisions between third nodes 238 and final nodes 242 shown in FIG. 4B. In some embodiments, the inflow capillary tree 180 and/or outflow capillary tree 195 may comprise 2, 3, 4, 5, 6, 8, 10, 12, 16, 20, 24, 32, 40, 48, 64, 80, 96, 128, 144, 160, 192, 256, 288, 320, 384, 512, 576, 640, 768, 1024, 1152, 1280, 1536, 2048, 2304, 2560, 3072, 4096, 4608, or 5120 nodes, or any value between two of the aforementioned values. In some embodiments, the smallest sub-branches 244 can be potted into the array of pots 245.

FIG. 4B illustrates the hollow fibers 190 received in each pot of the array of pots 245, such that the hollow fibers 190 may be in fluid communication with the smallest sub-branch 244 of the inflow capillary tree 180 and/or the outflow capillary tree 195 in the gas exchanger unit 110. FIG. 4B also illustrates a cross-sectional, close-up view of the pots of the array of pots 245 and of the potted hollow fibers 190 connected to one of the smallest sub-branches 244.

Finally, FIG. 4B illustrates a close-up sectional view of first node 234, which may be representative of the structure of any of the nodes described herein. In some embodiments, first sub-branches 232 may divided into multiple second sub-branches 236. In some embodiments, at the node 234 where the division occurs is a small arcuate section 246 comprising a radius. The small arcuate section 246, which may take the form of a flattened dome, may serve to reduce damage to red blood cells and molecules as they branch within the capillary tree. In some embodiments, the gradual curvature of the small arcuate section may reduce or eliminate damage to red blood cells and molecules as they move through the capillary trees described herein.

FIG. 4C illustrates a close-up sectional view of a pot of the array of pots 245. As illustrated, the pot houses one or more hollow fibers 190 and couples the hollow fibers 190 to the smallest sub-branches 244 of the inflow capillary tree and/or outflow capillary tree. In some embodiments, as shown in the example pot of FIG. 4C, the pot or cubicle is configured to hold an array of hollow fibers 190. For example, each pot or cubicle may couple a 3×3 array of hollow fibers to a sub-branch of the inflow capillary tree and/or outflow capillary tree.

Some embodiments described herein relate to systems, methods, and devices for potting, assembling, and sealing the hollow fiber unit of the gas exchanger. In some embodiments, the hollow fibers of the hollow fiber unit must be potted and sealed in a grid array, as discussed herein. In some embodiments, potting and sealing of the hollow fibers may involve an assembling device, and may involve methods for sealing a nutrient space from a blood space, sealing and fixing a hollow fiber unit exterior and/or shell, and resin potting into a hollow fiber assembly. In some embodiments, each of the inflow and/or outflow capillary tree branches and/or sub-branches must be sealed from each other.

In some embodiments, because of the unique design, structure, and function of the artificial placentas described herein, traditional potting, sealing, and assembly techniques used for similar devices may not be applicable. As such, in some embodiments, the artificial placentas described herein require unique potting, sealing and assembling technology for the hollow fiber membrane module.

In some embodiments, potting of the hollow fibers can be completed in units or sub-units, such as 3×3, 6×6, 9×9, 12×12, 15×15, 25×25, 27×27, 36×36, or 81×81 sub-units, any of the array dimensions discussed above, or any suitable array. In some embodiments, each of the, for example, 3×3 (or other dimension) sub-units can be combined to form a larger aggregate hollow fiber unit comprising, for example, a 32×32 array of 3×3 sub-units. In some embodiments, the aggregate unit array (e.g. 32×32 unit of 3×3 sub-units) may be potted and sealed to form a single hollow fiber unit. In some embodiments, the hollow fiber unit may be assembled using an assembly device, and assembly may comprise sealing a nutrient space from a blood space, sealing and fixing an exterior or shell of the hollow fiber unit, and resin potting the hollow fiber array into an assembly.

Figure 19A:
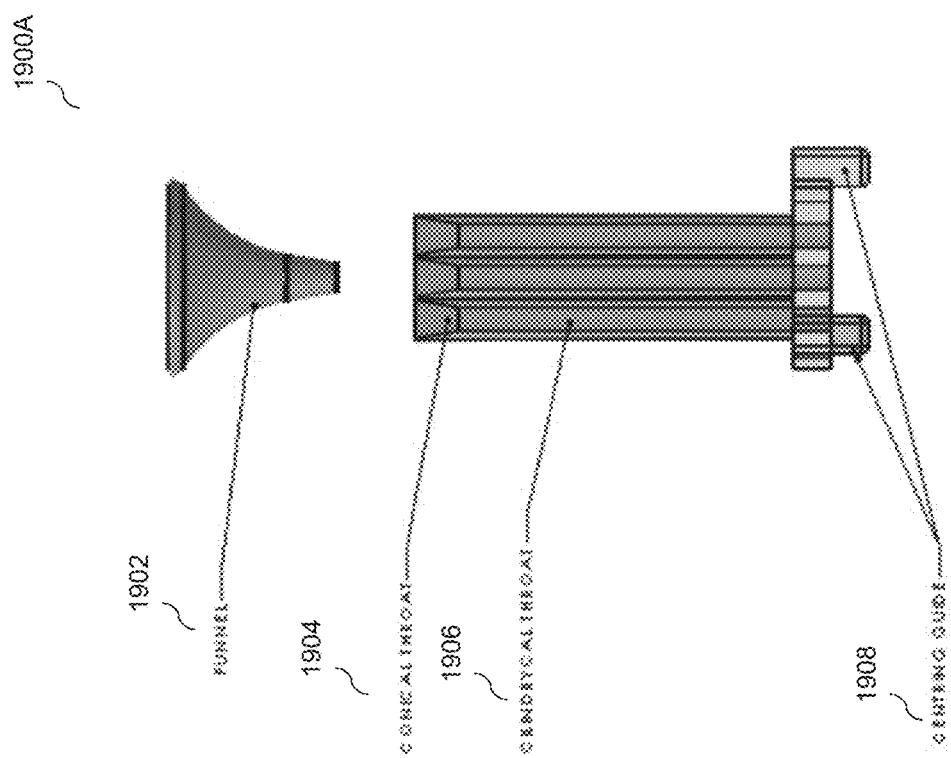
FIG. 19A illustrates an example potting assembly mechanism according to various embodiments herein.

In some embodiments, a series of potted hollow sub-units must be assembled. In some embodiments, each hollow fiber must be guided into a suitable pot via an assembly device or system, such as that shown in FIG. 19A. In some embodiments, an assembly mechanism 1900A comprises a suitable funnel 1902 configured to avoid damage to nearby hollow fibers during insertion of a hollow fiber there through. In some embodiments, the funnel 1902 enables the guiding of a hollow fiber into a conical throat 1904 of the assembly mechanism 1900A. In some embodiments, the hollow fiber is guided further through a cylindrical throat 1906 into a potting mold. In some embodiments, the number and arrangement of conical throats 1904 and cylindrical throats 1906 of the assembly mechanism 1900A will match the number and arrangement of the hollow fiber sub-units to be potted. In the example assembly mechanism 1900A, the conical throats 1904 and cylindrical throats 1906 are arranged in a 3×3 array to form a 3×3 sub-unit of hollow fibers according to various embodiments herein. It is to be understood that various numbers and arrangements of the conical throats 1904 and cylindrical throats 1906 may be used.

In some embodiments, the hollow fiber must be cut before or during the potting operation to an appropriate length to avoid fluid leakage and maintain a seal. In some embodiments, the hollow fibers may be cut using conventional tools known in the art. In some embodiments, the hollow fibers may also be cut once the entire sub-unit or unit is potted. In some embodiments, the cut of the hollow fibers may be completed after potting and assembly of each sub-unit, and may involve a precise cut of some or all of the hollow fibers of the hollow fiber unit. In some embodiments, one or more cuts of the hollow fibers may be completed using, for example, a simple knife or electric bread knife (for individual and/or multiple hollow fibers).

In some embodiments, coils of hollow fibers may be situated above the mold in order to unwind during the potting process. In some embodiments, there may be one hollow fiber coil. In some embodiments, there may be multiple coils of hollow fibers. In some embodiments, washing of the hollow fibers is necessary before potting may be completed. In some embodiments, the arrangement of conical throats 1904 and/or the cylindrical throats 1906 may be configured to dismantle vertically, such that the hollow fibers may be potted on both ends. In some embodiments, the potted ends of the hollow fibers may connect to, for example, an inflow capillary tree and/or outflow capillary tree.

In some embodiments, the assembly mechanism 1900A may be connected to a molding mechanism 1900B to enable potting of the hollow fibers into a fixed and stable mold. In some embodiments, the assembly mechanism may be coupled to the example molding mechanism 1900B of FIG. 19B. In some embodiments, the assembly mechanism and/or molding mechanism may comprise a centering guide 1908, which may assist in coupling the assembly mechanism with the molding mechanism, such that the hollow fibers can be properly potted and sealed.

The molding mechanism 1900B may comprise a mold 1910 configured to house the potted hollow fibers in proper placement while a resin sets. Resin may be inserted into the molding mechanism via a resin-in funnel 1912 and may be heated by heater 1914. The heater 1914 may be connected to a power supply 1915. The molding mechanism may also comprise a bottom sliding plate 1916, which slides under the mold 1910 and locks in the correct placement. A plate limiter 1918 prevents movement of the bottom sliding plate 1916 beyond its intended placement beneath the mold 1910.

Figure 19E:
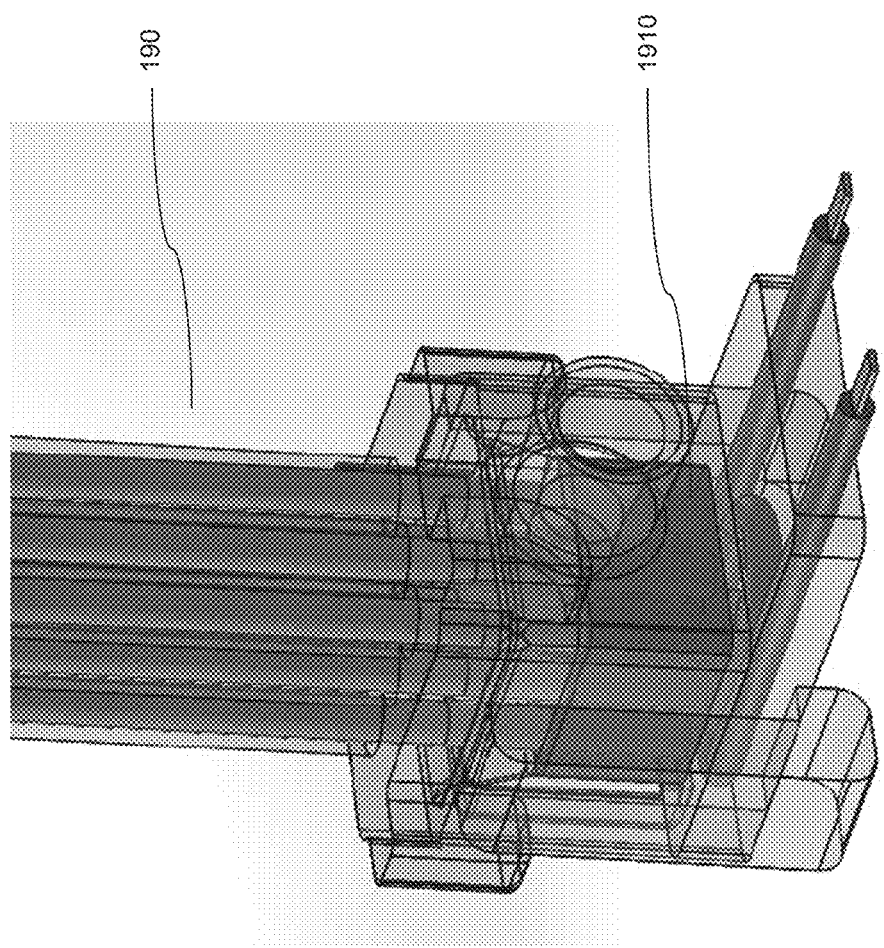
FIG. 19E illustrates a perspective translucent view of a combined assembly and molding mechanism with implanted hollow fibers according to various embodiments herein.

FIG. 19C illustrates a top view of the combined assembly and molding mechanism. FIG. 19D illustrates a side view of the same. In the example embodiment of FIG. 19C, the bottom sliding plate has not been inserted beneath the mold while the example embodiment of FIG. 19D illustrates the assembly and molding assembly 1900 with the bottom sliding plate in position for hollow fiber potting and sub-unit assembly. The example embodiments of FIG. 19C-19D also illustrate the funnel 1902 inserted into the one of the conical throats 1904, which may be attached to the cylindrical throats 1906, which may be inserted into the mold, such that they can be used to guide the hollow fibers into their correct equidistant and parallel placements. In some embodiments, as shown in FIG. 19D the hollow fibers may be inserted through the funnel 1902 and guided into the mold 1910 by conical throats 1904 and cylindrical throats 1906. In some embodiments, vacuum may be applied in order to pull the hollow fibers downwards into the mold 1910. Each hollow fiber may be inserted into the mold individually through a separate conical throat 1904 and cylindrical throat 1906, such that the hollow fibers are arranged vertically in an equidistant array, such as that shown in FIG. 19E.

In some embodiments, after implantation of the hollow fibers 190 into the mold 1910, a resin can be applied within the mold 1910, via, for example, the resin-in funnel 1912. The resin can be applied with a syringe or other similar device and/or method of insertion. In some embodiments, the height of the mold and the volume of resin applied may be determined and may be optimized to maximize the sealing characteristics of the cartridge or pot. In some embodiments, the hollow fibers may slightly curve between the top and bottom of the mold 1910. The height of the mold 1910 can be optimized to minimize the curve ratio of the hollow fibers within the mold 1910. However, the level-height of resin to-be-added must also be determined, which will also affect the height of the mold.

In some embodiments, after resin has been applied, the heater 1914 can be used to heat the resin within the mold 1910. In some embodiments, heat may be applied according to resin manufacturer's instructions. For example, for epoxy LOCTITE® EA E-30CL™, the manufacturer states that a resin mass of 250 g should be heated at 100° C., with a cure time of 90-150 seconds. During the cure process, resin may leave varnish on the external walls of the hollow fibers. The height of varnish may be unknown prior to application, but it may be anything between around 0.1 mm to 10 mm, or any value between the aforementioned values. In some embodiments, the height of varnish may depend on resin type. The height of varnish may be optimized by experimentation with cure temperatures. In some embodiments, appropriate venting of the area around curing resin will lead to optimal (i.e. minimum) height of varnish. In some embodiments, the varnished surface should be taken into account when determining hollow fiber length, because the varnished surface may decrease hollow fiber capacity.

In some embodiments, the mold for the 3×3 hollow-fiber sub-unit may have chamfer on the edges in order to provide an air pocket that may be filled with resin during the unit (e.g. 32×32) potting process. In some embodiments, the 3×3 (or other dimension) sub-units may be potted into 32×32 (or other dimension) units. Thus, one end of the hollow fiber unit may comprise a 32×32 array of 3×3 hollow fiber sub-units.

Figure 19F:
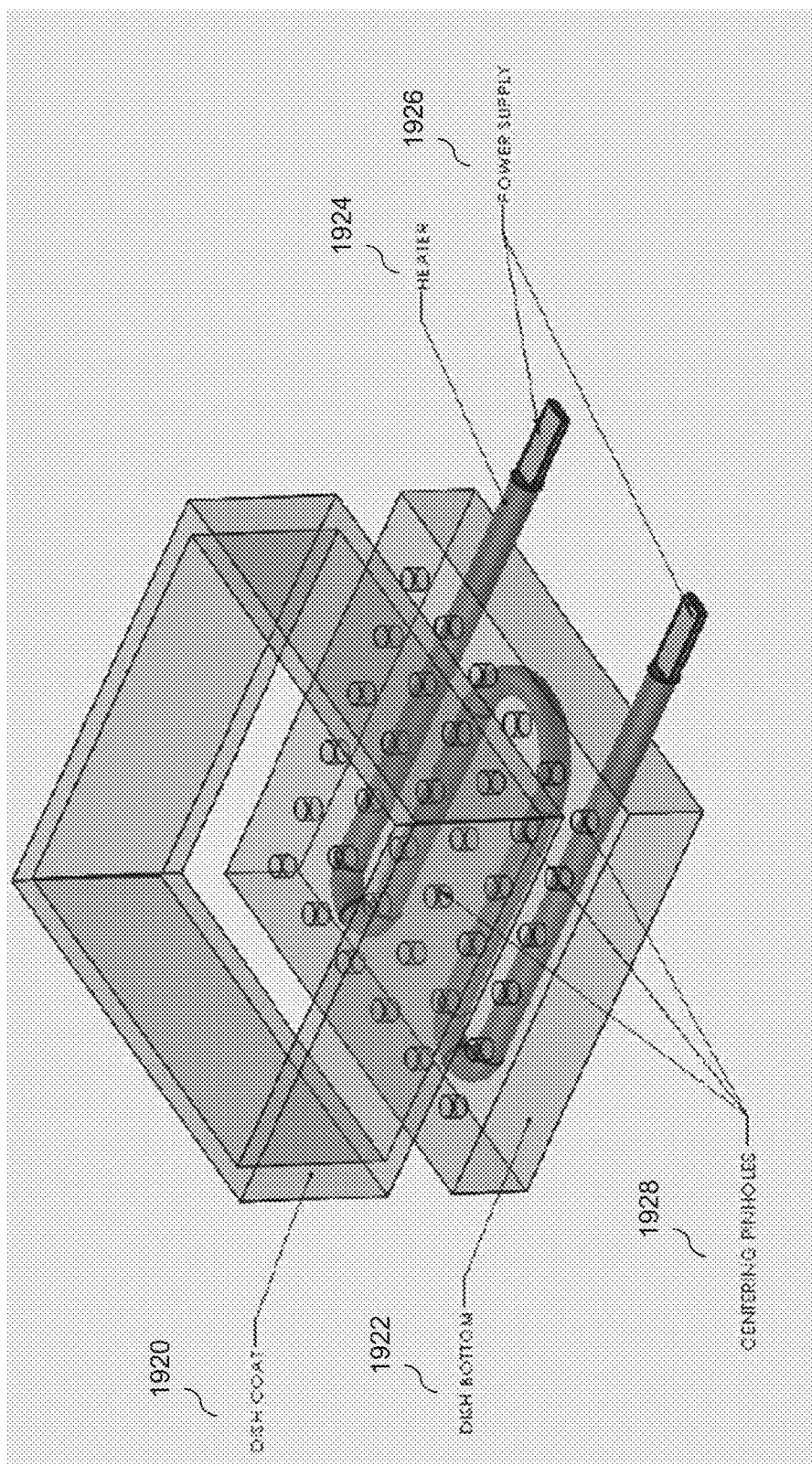
FIG. 19F illustrates an example unit potting dish according to various embodiments herein.

FIG. 19F illustrates an example unit potting dish according to various embodiments herein. The illustrated embodiments shows 6×6 potting dish, but the same principle can be used on 32×32 (or other dimensions) potting. In some embodiments, the potting dish may comprise an exterior potting coat 1920, a dish support bottom 1922 a heater 1924, and a power supply 1926. In some embodiments, the example potting dish may comprise one or more centering pinholes 1928 for centering the 3×3 hollow fiber sub-units into the proper locations within the potting dish. In some embodiments, the dish bottom 1922 can be made out of two parts for the purpose of separation after molding and cleaning for reuse of the mold. In some embodiments, for both the 3×3 sub-unit and 32×32 unit potting, disposable rubber/silicone seals and clamps that would can be used to hold the mold and seal the mold tight in order to prevent resin from leaking out. In some embodiments, a thin film of fast-cure resin is to be used on the button surface of each 3×3 sub-unit, rather than on the surface of dish bottom 1922.

Figure 19G:
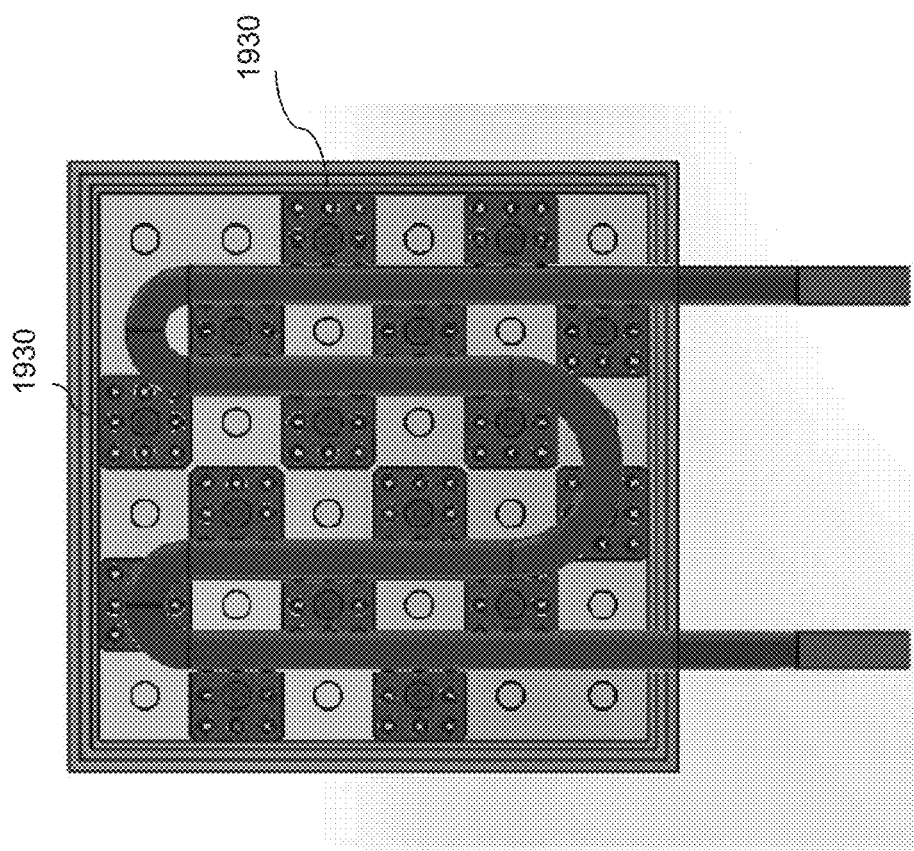
FIG. 19G illustrates an example embodiment of a first phase hollow fiber unit potting pattern according to various embodiments herein.

In some embodiments, unit potting should be completed in two phases. In the first phase, the pattern 1930 shown in FIG. 19G should be potted, in a zigzag manner. In the second phase, the remaining 3×3 (or other dimension) sub-units can be potted. In some embodiments, if phase two proves to be difficult to handle, the height of 3×3 resin may be completed in two different sizes. A smaller height can be used for phase one and a larger height can be used for phase two in order to ease the potting of the phase two 3×3 sub-units. In some embodiments a pin on the end of the 3×3 (or other dimensions) sub-unit may be inserted into one of the centering pinholes 1928 to lock the sub-unit into its exact place. In some embodiments, the shape of the pin should be conical to enable easy separation in later steps of the assembly process.

Once both phases of the unit potting have been completed, the other ends of the hollow fibers should be potted into sub-units and unit according to the same process. In some embodiments, it may be optimal to pot the 3×3 (or other dimension) sub-units simultaneously in both dishes (both ends). In some embodiments, to enable simultaneous potting, the dishes will need to be oriented at an angle to one another. In some embodiments, the two dishes cannot share the same flat surface during potting, because length of the hollow fibers will not be sufficient to simultaneously pot both ends. In some embodiments, an angle among the dishes may be achieved with V shaped pad (e.g. open book shape) that can be removed before resin is applied.

In some embodiments, the exact shape of the potting dish (i.e. mold) must be designed in detail in order to assure resin inflow and air discharge. In some embodiments, the bottom plate should be designed in such manner to allow a thin layer of resin to flow under the 3×3 sub-units and pack them in single unit after curing process. Also, in some embodiments, the dish should be designed in such manner that removing the cast (e.g. 96×96 hollow fiber unit) is easiest by applying, for example, angles, cones and fillets.

In some embodiments, resin can be applied to one or both dishes via single or multiple funnels. In some embodiments, resin may be applied with gravitational flow (i.e. free flow). In some embodiments, after resin is applied in the dish-mold, heat can be applied by heater 1924. In some embodiments, the cure process is relatively fast depending on resin. In some embodiments, if a dish position is not found that will enable application resin in both molds simultaneously, one dish can be completed at the time, while the other dish is positioned sideways (e.g. making L shape with dish o which resin is being applied). In some embodiments, this may be necessary because the current free length (e.g. 50 mm) of the hollow fibers is not sufficient to reach both ends when they are positioned in dish-molds, which are both laying on a flat surface. In some embodiments, during application of the resin, the molds are to be submitted to centrifuge, having a predetermined speed and optional centrifuge direction change.

As with the 3×3 sub-unit potting, in some embodiments, the resin varnish surface should be taken into account when deciding on fiber length, because the varnish surface will decrease hollow fiber capacity. Also, in some embodiments, it may be inevitable that some percentage of the hollow fibers will be penetrated by resin or flatten during potting process. In some embodiments, this issue may be solved by adding a safety factor in the number of required hollow fibers for proper functionality.

In some embodiments, the hollow fibers must be cut subsequent to potting the sub-units and units. In some embodiments, the cut has a purpose of opening all hollow fibers on both sides, enabling them to transport blood from one side to another. In some embodiments, the cut is a critical operation and needs to be done very precisely to allow proper functionality of the hollow fiber unit. In some embodiments a constructed cutting machine may be utilized for a sliding cut of the hollow fibers. In some embodiments, it may be suitable to complete the cutting in two steps: first a raw cut and then a fine cut (or multiple fine cuts) in order to get a smoother surface.

Figure 19H:
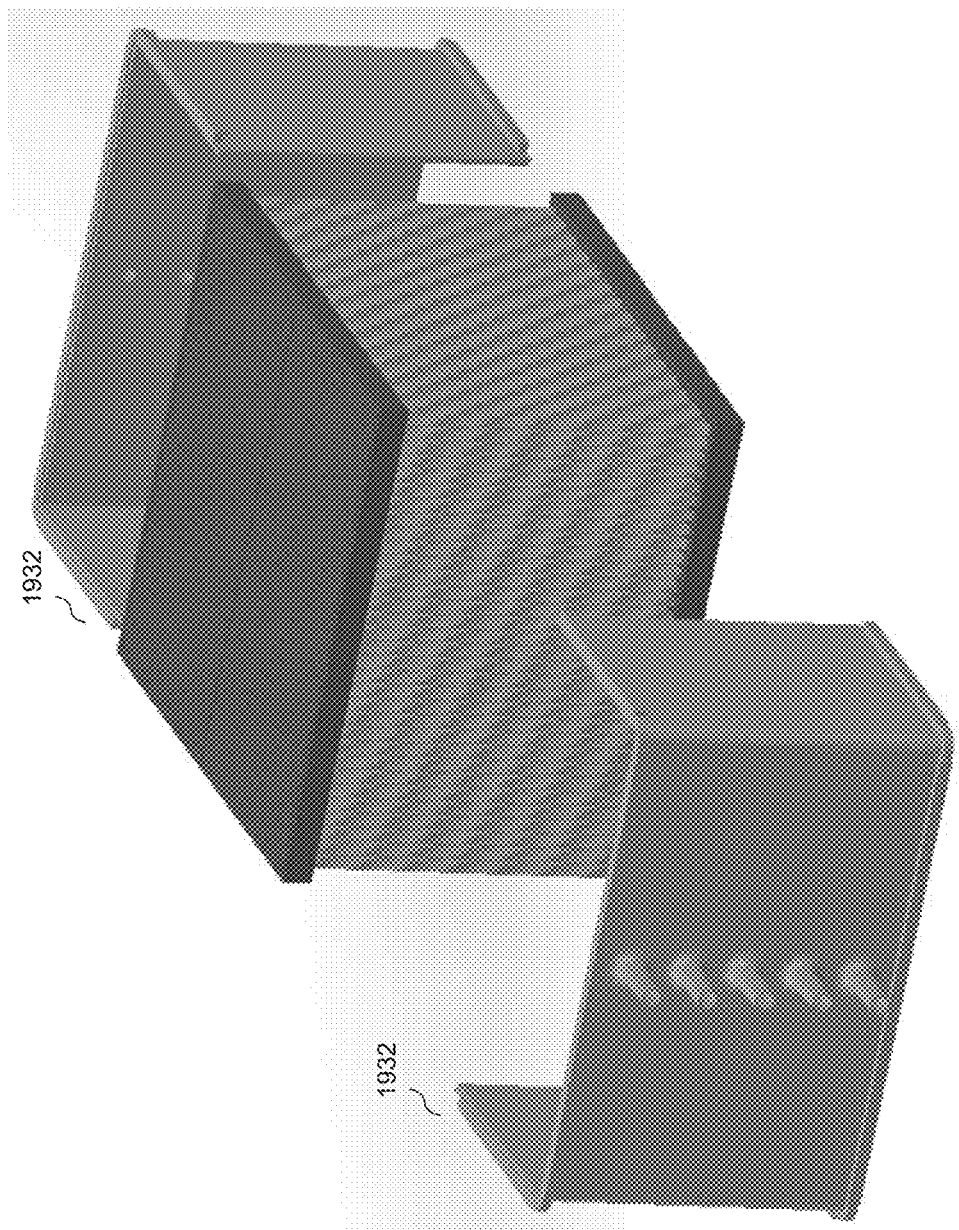
FIG. 19H illustrates a hollow fiber unit side shell according to various embodiments herein.
Figure 19I:
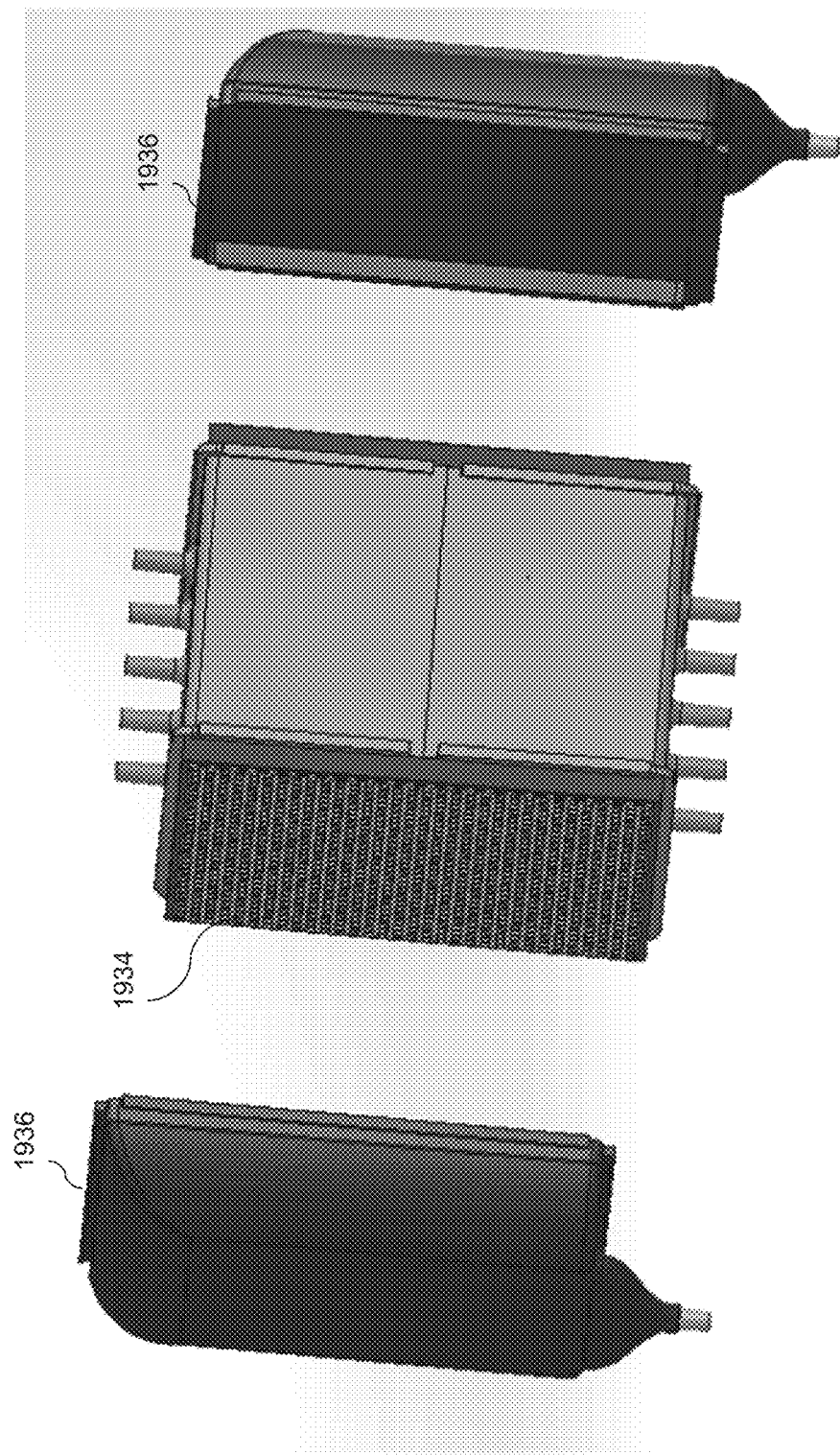
FIG. 19I illustrates an example embodiment of a hollow fiber unit and application of exterior shells according to various embodiments herein.

After potting and cutting of the hollow fibers on both ends, the assembly may comprise a 32×32×9 hollow fiber unit, which be further assembled using a side shell 1932, as show in FIG. 19H. In some embodiments, the side shell 1932 may comprise a two-piece assembly, which may mover the hollow fibers after being put into place. After the side shell 1932 is put together on the exterior of the potted hollow fibers, ultrasonic welding can be applied to create, for example, a strip seal. The strip seal may be used along with a belt clamp to hold the shell in a tight position and seal the hollow fibers from the outside atmosphere. In some embodiments, fast acting plastic glue can be sued for the seal. In some embodiments, the pressure rating inside the shell must be verified before applying a seal. In some embodiments, gaskets 1934 can be added at each exterior end of the hollow fiber unit, as shown in FIG. 19I. Gasket may be applied between the capillary body and cured resin in order to prevent blood mixing from separate capillary branches.

Figure 19J:
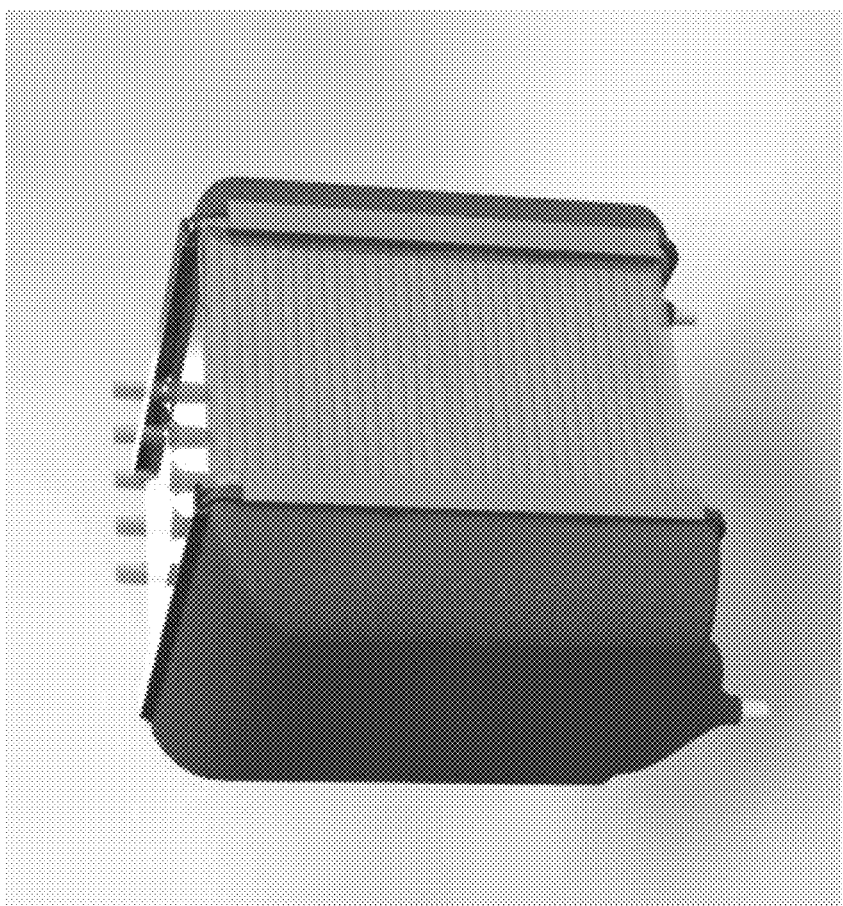
FIG. 19J illustrates an example embodiments of an assembled hollow fiber unit according to various embodiments herein.

In some embodiments, an end shell 1936 may also be used to encapsulate the ends of the hollow fiber unit. The end shell 1936 may comprise multiple pieces which may be assembled to create a sealed exterior of the hollow fiber unit. In some embodiments, between the multiple pieces of the end shell and between the capillary bodies a square seal comprising silicone may be used. In some embodiments, capillary bodies may be positioned to match the resin squares of the hollow fiber unit and to allow flow of blood into the hollow fibers. Clamps and/or may be used to seal the end shell 1936 to the side shell 1932 and the hollow fiber unit. In some embodiments, gasket thickness and claw sizing may be completed after the area of surface of resin is known (e.g. after calculation of number of hollow fibers). An example assembled hollow fiber unit is illustrated in FIG. 19J.

In some embodiments, hollow fibers must be washed thoroughly before and during assembly in the hollow fiber unit. In some embodiments, hollow fibers are filled with non-toxic fluid (e.g. isopropyl), which helps maintain structure during the manufacturing process. In some embodiments, after cutting the hollow fibers, the fibers are open and fluid may leak out. In some embodiments, it is necessary to wash the fibers in order to remove leftovers of any oily substances. In some embodiments, Freon (e.g. dichlorodifluoromethane) may be a suitable washing liquid. In some embodiments, because of environment risks other substances may be more suitable.

Gas Exchange

In some embodiments, the exchanges of gases occurring within the gas exchanger unit 110 are carefully controlled and adjusted based on external factors by controlling blood and gas pressures and flow rates in the gas exchange unit. In some embodiments, the exchange of gases may be controlled via thresholds and triggers established by a user, or automatically generated by the control unit 165.

FIG. 5A is a graph illustrating the solubility of oxygen in water. FIG. 5B is a graph illustrating the solubility of carbon dioxide in water. As shown in FIBS. 5A and 5B, carbon dioxide has a much higher solubility than oxygen in water. As such, in some embodiments, the control unit may be configured to strictly monitor and control the exchange of oxygen into blood within the gas exchanger 110. For example, by utilizing various dynamic algorithms, the control unit 165 may be configured to automatically monitor and control the necessary oxygen gas exchange. In some embodiments, the oxygen gas exchange may depend on fixed values and/or variable conditions, which the control unit 165 may be configured to evaluate. In some embodiments, the fixed values may comprise the membrane area, the membrane thickness, and/or solubility, among others. In some embodiments, variable conditions may comprise atmospheric pressure, differential partial pressure, and/or decreased capacity of the membrane because of serum leak through microspores, among others.

FIG. 5C is a graph showing atmospheric pressure as a function of altitude. FIG. 5C illustrates the importance of atmospheric pressure and how it can vary with altitude. In some embodiments, the control unit 165 may be configured to monitor altitude and/or atmospheric pressure in making various calculations to control the gas exchange process. In some embodiments, by taking this information into consideration, control unit 165 may change oxygenation pressure by altering the partial pressure of oxygen in the infiltration gas 160. In some embodiments, the control unit 165 may alter the partial pressure of oxygen by increasing or decreasing the oxygen fraction in the infiltration gas mixture. In some embodiments, the partial pressure and gas fractions in the infiltration gas 160 may be altered automatically or manually by the use of various valves of the system, as described herein. The oxygenation pressure can be changed by, for example, changing the partial pressure of oxygen in the gas, which can be achieved by affecting the oxygen fraction in the gas mixture, and/or by affecting gas pressure in the gas exchanger 110. The latter can be limited since excessive pressure (bubble point pressure) across the filter medium can allow the passage of air through the pores of the membrane.

The gas exchanger may comprise a jacket configured to encase the hollow fiber unit and seals the interior of the gas exchanger from the atmosphere, thus producing a sealed gas exchange chamber. In some embodiments, the gas exchanger further comprises manifolds for multiple gas inlets 200 and outlets 210 as shown on FIG. 2A, wherein the position of the manifolds in relation to the hollow fibers enable perpetual gas flow through the jacket in relation to blood flow through the hollow fibers.

Alternative Artificial Placenta

Figure 6:
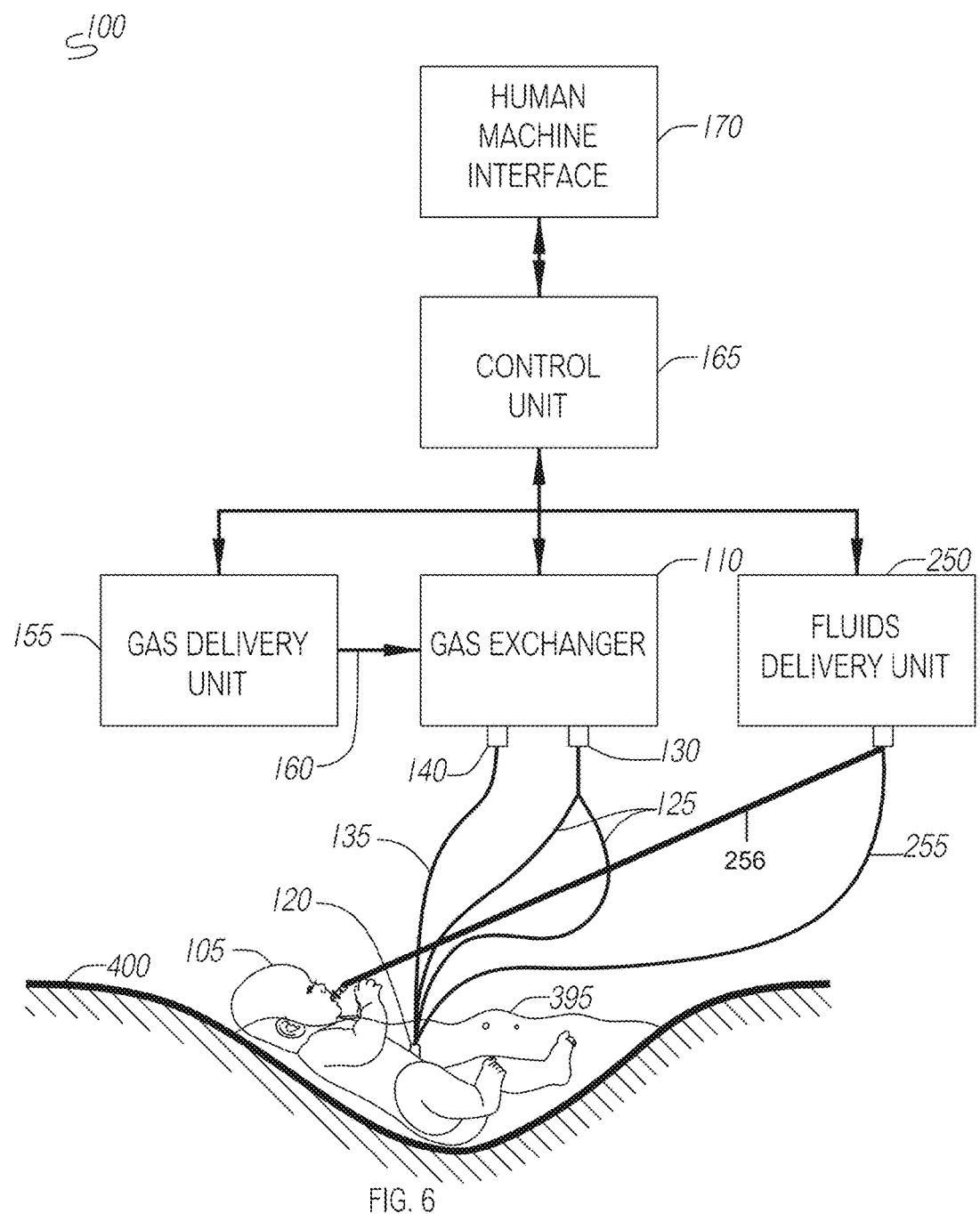
FIG. 6 is schematic diagram of another example embodiment of the artificial placenta, nutrients delivery, heparin delivery and amniotic fluid oral delivery system according to various embodiments herein.

FIG. 6 is schematic diagram of another example embodiment of the artificial placenta and amniotic bed system according to various embodiments herein. In some embodiments, instead of an amniotic bed, a standard air control incubator may be used in combination with the artificial placenta. In some embodiments, no incubator or amniotic bed system is required; the artificial placenta system may operate as a stand-alone apparatus. The example embodiment of FIG. 6 may comprise some or all of the features of the example embodiment illustrated in FIG. 1, and may further comprise a fluids delivery unit 250. In some embodiments, the fluids delivery unit 250 comprises one or more fluids that may be selectively administered to the blood of the infant 105. In some embodiments, the fluids may comprise, for example, heparin, water, nutrients and the like. In some embodiments, the fluids may be administered via one or more fluids lines 255, 256, which may be connected to the one or more arterial lines 125 prior to oxygenation and/or to the one or more venous lines 135 after oxygenation. In some embodiments, fluid may be administered via the fluid delivery unit 250 and the one or more fluids lines 255 independent of the gas exchanger, one or more arterial lines 125, and/or one or more venous lines 135. In some embodiments, amniotic fluid and/or other fluids may be administered orally via fluid line 256.

In some embodiments, the fluids may be administered via the one or more fluids lines 255 to the one or more venous lines 135. In some embodiments, heparin may need to be administered additionally or alternatively to the one or more arterial lines 125 and/or venous lines 135 to minimize coagulation of blood within the system.

In some embodiments, the fluids may be contained within disposable cartridges of predetermined volume. In some embodiments, fluids can be delivered with, for example, metering pumps. In some embodiments, flow rates and other fluid properties (i.e. chemical and physical properties of the fluid) may be continuously monitored by sensors in communication with the control unit 165. In some embodiments, the control unit 165 monitors and controls the operation of the fluid delivery unit based on user defined presets. In some embodiments, the control unit dynamically monitors and updates system parameters using artificial intelligence (AI) and or machine learning (ML).

Detailed Artificial Placenta Schematic

Figure 7:
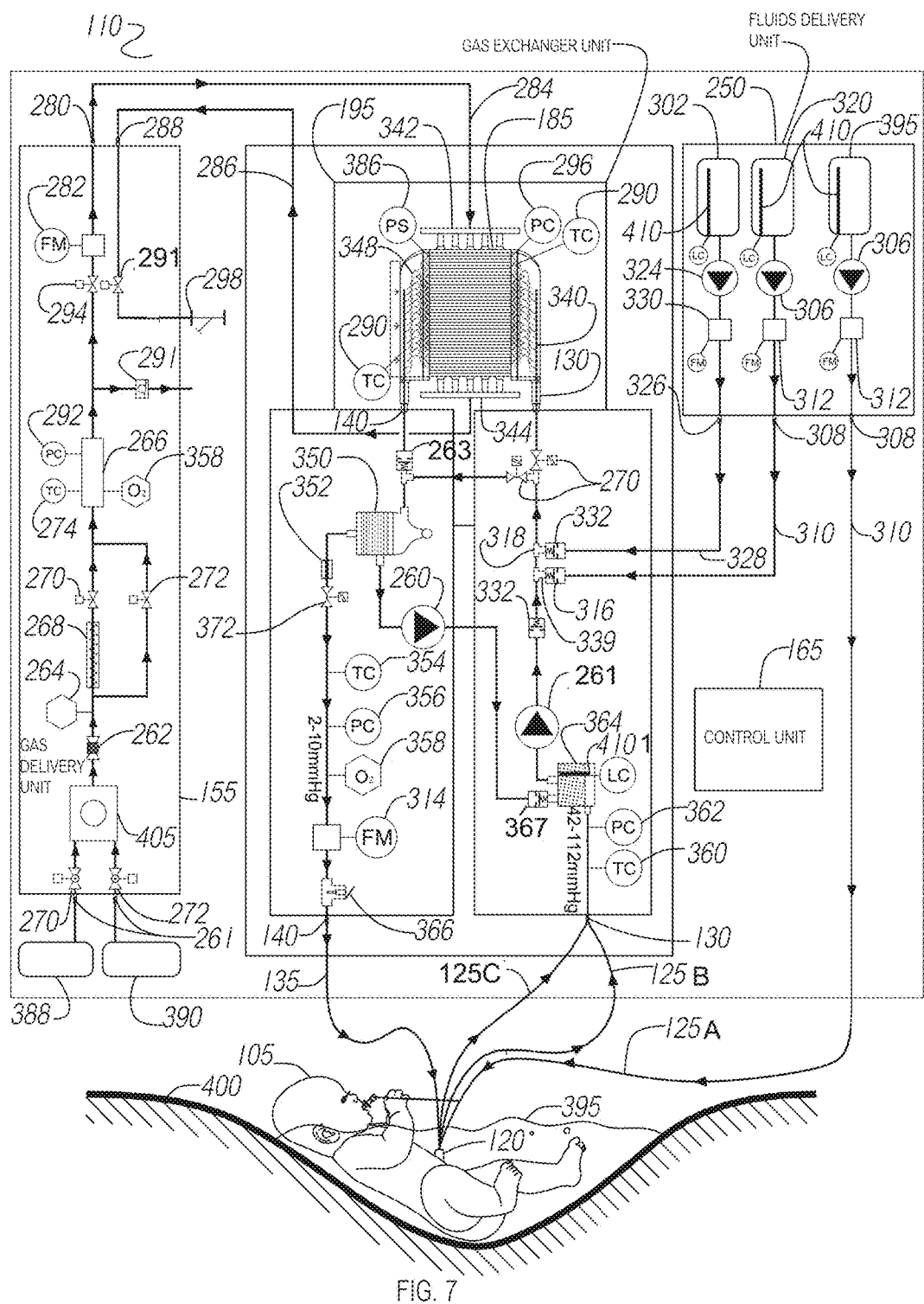
FIG. 7 is a detailed schematic diagram of the example embodiment of the artificial placenta, nutrients delivery, heparin delivery and amniotic fluid oral delivery system according to various embodiments herein.

FIG. 7 is a detailed schematic diagram of an example embodiment of the artificial placenta and amniotic bed system according to various embodiments herein. In some embodiments, instead of an amniotic bed, a standard air control incubator may be used in combination with the artificial placenta. In some embodiments, no incubator or amniotic bed system is required; the artificial placenta system may operate as a stand-alone apparatus. It should be noted that the configuration and order of components of the system is not limited to the illustrated embodiment. Various alternative configuration and component orders will be recognized by a person of ordinary skill the art. In some embodiments, a first gas input into the gas exchanger system may be provided by a gas delivery unit 155.

In some embodiments, gases may be selectively introduced into the gas exchanger 110 via the gas delivery unit 155. Gas, such as, for example, oxygen gas, nitrogen gas, and/or ambient air may be sourced to the gas delivery unit via, for example, feeder lines, wherein the feeder lines may be connected on one end to gas tanks such as, for example, oxygen tank 388 and ambient air tank 390. The other end of the feeder lines may be connected to one or more inlet ports 261 on the exterior of the gas delivery unit 155. Some embodiments may comprise one or more gas pumps for effecting delivery of one or more gases to the gas delivery unit 155 and/or gas exchanger 110.

In some embodiments, the gases passing through the inlet ports 261 may be received by valves 270 and 272. In some embodiments, valves 270 and 272 comprise, for example, metering-type valves with solenoids. In some embodiments, the valves 207 and 272 may be remotely controlled by, for example, signals sent from control unit 165. In some embodiments, gases from valves 270 and 272 may enter a blender 405. In some embodiments, additional valves 270 and 272 may be located downstream of blender 405. In some embodiments, the blender may comprise a manifold having Diameter Index Safety System (DISS) and/or National Institute of Standards and Technology (NIST) compliant oxygen fittings with internal valves. In some embodiments, the internal valves may be controlled by the controller unit 165, which may allow for predetermined, selective gas blend outputs from the blender 405. In some embodiments, the controller 165 may dynamically control the internal valves of the blender 405 based on the fixed values and variables factors described herein to create a constantly varying gas blend.

In some embodiments, gas from the blender 405 may be delivered to an air filter 262 comprising a porous filter membrane. In some embodiments, the porous filer membrane comprises a submicron filter. In some embodiments, the porous filer membrane comprises a filer having pore sizes of approximately 0.2 micron diameters. In some embodiments, the porous filer membrane comprises a filer having pore sizes of about 0.01, about 0.02, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 20, about 30, about 40, about 50, about 100, about 200, about 300, about 400, about 500, or about 1000 microns, or any value between two of the aforementioned values. In some embodiments, the air filter 262 may prevent dust and large impurities from entering system.

In some embodiments, gases from the air filter 262 may be delivered to a gas analyzer 264. In some embodiments, the gas analyzer 246 may periodically or continuously measure various gas parameters. Gas parameters may include, for example, temperature, gas quality, partial pressures, and/or gas fractions (e.g. oxygen gas fraction), among others. In some embodiments, data from the gas analyzer 264 may be transmitted to control unit 165 and utilized in various gas blending algorithms to govern the functionality of, for example, blender 405.

In some embodiments, gas from the blender 405 and gas analyzer 264 may be sent to a heater 268. The heater 268 may alter and/or maintain the gas temperature to a desired or required value. In some embodiments, the temperature of the gas mixture may be controlled with heater 268 in combination with valves 270 and 272, which may alter the temperature of the gas mixture by mixing gases of different temperatures (e.g. oxygen gas at a first temperature and ambient air at a second temperature) in desired or required proportions. In some embodiments, the valves 270 and 272, the blender 405, and the heater 268 may controlled in combination to heat or cool the gas mixture temperature to desired or required set point(s), as dictated by control unit 165. In some embodiments, gas temperature may be periodically or continuously measured using one or more temperature sensors 274, which may be located upstream, within, or downstream of the heater 268. In some embodiments, gas pressure may be monitored using one or more pressure sensors 292. In some embodiments, the heater surface temperature is constantly measured by one or more temperature sensors, which may transmit temperature data to the control unit 165.

In some embodiments, gas from the heater 268 may be transported through internal tubing to one or more wall mount connectors 280. In some embodiments, gas flow rate may be periodically or continuously measured with, for example, a flow meter 282 upstream and/or downstream of one or more wall mount connectors 280. In some embodiments, disposable tubing 284 may be used to deliver gas to one or more gas inlets of the gas exchanger unit 110. The gas exchanger unit may comprise various components for oxygenating blood according the various embodiments described herein. In some embodiments, gas may exit the exchanger unit 110 through one or more gas outlets.

In some embodiments, gas may return from the gas exchanger 110 through disposable tubing 286 into gas delivery unit 155 through one or more wall mount connectors 288. In some embodiments, gas temperature within the gas exchanger unit 110 may be periodically or continuously measured with one or more temperature sensors 290. In some embodiments, if the gas temperature varies from predefined or dynamically defined levels (i.e. set within controller unit 165), valves 270 and/or 272 may alter respective gas flow rate to control gas temperature, as discussed above. In some embodiments, a condensation removal system 293 is also provided to remove excess water built up inside gas exchanger unit 110 and/or gas delivery unit 155.

In some embodiments, a second input to the gas exchanger may be fluids from a fluids delivery unit 250. In some embodiments, the fluids delivery unit 250 may be continuously monitored and controlled by the control unit 165. In some embodiments, fluid inputs can include, for example, Heparin or another anti-coagulant from a Heparin tank 302, nutrients from a nutrient tank 320, and/or simulated amniotic fluid from an amniotic fluid tank 395, and the like. In some embodiments, fluid tanks used by the system may comprise disposable cartridges, which may comprise predetermined volumes and/or level sensors 410 connected to the control unit 165. In some embodiments, the level sensors 410 may send data to the control unit 165 to be utilized in algorithms, which may trigger alterations in fluid distribution or may trigger alarms based on predetermined or dynamically determined thresholds.

In some embodiments, each fluid may be metered into the blood by means of pumps 306 and 324 through flow meters 312 and/or 330, which may also be connected to, monitored by, and controlled by control unit 165. In some embodiments, readouts from the pumps 324 and/or 306 may be relayed to control unit 165 and factored into algorithms to govern fluid volumes and flow rates into the blood. In some embodiments, heparin and/or nutrient fluids may be introduced to gas exchanger unit 110 through, for example, disposable tubes 328 and/or 310. In some embodiments, the fluids may pass through back flow preventers 332 and/or 316 into outflow ports 318 and/or 339. In some embodiments, to exit the tanks, fluids may pass through connectors 308 and disposable tubing 310 and/or 328. Simulated amniotic fluid may be delivered into, for example, the one or more arterial lines 125 and administered to infant, or directly to the infant orally through an oral line 125A. In some embodiments, nutrients may be administered into the one or more arterial lines 125B and 125C similar to the aforementioned simulated amniotic fluid.

In some embodiments, the gas exchanger 110 comprises the main circulation portion of the system. As described above, one or more gas exchanger inlets 130 may be connected to one or more arterial lines 125 delivering blood from a, for example, preterm infant to the gas exchanger 110. In some embodiments, low-oxygen blood from the infant may enter the system and be monitored by one or more temperature monitors 360, pressure monitors 362, level sensors 410 and oximeters in a reservoir 364. In some embodiments, data from the various monitors may be transmitted to control unit 165 for monitoring and controlling the blood properties. In some embodiments, blood may delivered to the gas exchange unit 110 by means of one or more pumps 260, 269 from a reservoir 364. In some embodiments, the blood may pass through one or more backflow preventers 332 and valves 270 before reaching the aforementioned inflow capillary tree 180.

In some embodiments, the gas exchanger unit 110 comprises an inflow capillary unit 340 comprising inflow capillary tree 180, and each sub-branch end of the capillary tree delivering blood to the hollow fiber unit 185. In some embodiments, an inlet gas manifold 342 may deliver gas from the gas delivery unit 155 to the gas exchanger unit 110.

In some embodiments, an outlet gas manifold 344 may transfer gas out of gas exchanger 110 to, for example, the gas delivery unit 155.

In some embodiments, the gas exchanger 110 may comprise a jacket encasing hollow fiber unit 185 and sealing the gas exchanger 110, producing a gas exchange chamber. In some embodiments, the position of inlet gas manifold 342 and outlet gas manifold 344 in relation to the hollow fibers may enable perpetual gas flow through the gas exchanger jacket in relation to blood flow through the hollow fibers.

As previously mentioned, the hollow fiber unit 185 may comprise a plurality of hollow fibers 190 arranged in a geometric pattern or array for transporting blood from an inflow capillary unit 340 to an outflow capillary unit 348. During blood passage through the hollow fibers 190, oxygen and carbon dioxide gas exchanges may occur between blood in the hollow fibers 190 and gas outside of the hollow fibers 190. In some embodiments, the blood in the hollow fibers 190 becomes oxygenated by the gas exchange occurring within the hollow fiber unit. In some embodiments, the outflow capillary unit 348 may contain an outflow capillary tree 195, which may mirror the inflow capillary tree 180, and may transport blood to the one or more outlets 140, which may be connected to one or more venous lines 135.

In some embodiments, as the blood flows back to the infant 105 via the one or more venous lines (i.e. umbilical vein catheters) 135, it may pass through a backflow preventer 263 and a venous bubble trap 350 comprising a blood filter configured to separate gas bubbles from the blood. In some embodiments, the blood may also pass through a bubble detector 352, configured to monitor and detect bubbles to ensure that any bubbles are extracted into the bubble trap 350. The one or more venous lines 135 may also comprise a temperature monitor 354, a pressure monitor 356, a flow meter 314 and/or oximeter 358, which can be connected to the control unit 165, such that pressure, temperature and oxygen levels can be periodically or constantly monitored by control unit 165. In some embodiments, the one or more venous lines 135 may also be equipped with a Luer port 366 for direct pharmaceuticals administration.

In some embodiments, the gas exchanger 110 may also comprise gas-tight ports for non-disposable sensors, a gas temperature sensor 290, a gas pressure sensor 296, and/or a presence sensor 386 for detecting blood leakage. In some embodiments, these sensors may be provided in the jacket of the gas exchanger 110. In some embodiments, circulation of the blood may be completed by returning the one or more venous lines 135 to umbilical cord of a preterm infant 105. In some embodiments, the infant 105 may be disposed inside an amniotic bed 400, such as those described herein, which may be filled with simulated amniotic fluid 395.

The system may also comprising a control unit 165 comprising, for example, a programmable logic controller (PLC), supervisory control and data acquisition (SCADA), and the like, along with a human machine interface 170. In some embodiments, the human machine interface may comprise a graphical interface with input/output devices, such as, for example, a touch screen. In some embodiments, firmware or software within the control unit 165 and human machine interface 170 may be compatible with various forms of software programming languages such as, for example IEC 61131-3 compliant PLC languages such as Ladder Diagram (LD), Function Block Diagram (FBD), IL, SFC, ST and similar or other general purpose programming languages, Java, C++, Visual Basic™, Fortran, Basic and the like. In some embodiments, the human machine interface 170 may comprise software compatible with a plurality of operating systems such as, for example Windows, Apple operating systems, and Android operating systems, and compatible with a multitude of hardware platforms such as, but not limited to: personal desktops, laptops, tablets, smartphones and the like. In some embodiments, compatibility with other software platforms may allow practitioners to share and utilize data in common formats and allow data to be transmitted to, for example, cloud networks for medical researchers and staff.

In some embodiments, the controller unit may comprise firmware comprising, for example, an oxygen failure procedure algorithm. For example, when an oxygen failure is detected, such that blood oxygen levels are below predefined or dynamically determined ranges within gas exchange unit 110, an alarm sound and a visual alarm may initiated on the human machine interface 170. In some embodiments, the control unit 165 may be further connected with oxygenation input and output systems. In some embodiments, the control unit 165 may configured to send a signal to an oxygenation machine to start operating when oxygen levels are determined to need adjustment within the system. In some embodiments, if the oxygenation machine does not have an available input/output system connectable with an output signal of the control unit 165, the human machine interface 170 may be configured to display one or more instructions to supervising personnel to immediately turn on the oxygenation machine manually. In some embodiments, the blood and gas flow paths may be closed by operating valves 270, 272, and/or 372. In some embodiments, heater 268 and pump 260 can also be halted automatically by the control unit 165 and/or manually. In some embodiments, a hospital's existing source of pressurized gas and/or one or more external pressurized gas tanks can be used by the system. An oxygen supply line and/or an air supply line can be connected to entrance valves. Alternatively, the oxygen line can connect to an oxygen tank and the air line can connect to an air tank.

In some embodiments, gas pressure in the gas exchanger 110 may be periodically or continuously measured with pressure transmitter 296 and control unit 165. In some embodiments, excess gas buildup may be released into the atmosphere through a strainer 298. In some embodiments, the control unit 165 may govern gas pressure in the gas exchanger 110 to maintain a range between about 50-390 mm/Hg in order to prevent bubbles from forming in the blood-carrying channels of the hollow-fiber. In some embodiments, in the unlikely event that gas breaches an upper or lower threshold predetermined by the control unit 165, the gas exchanger 110 may be configured to depressurize automatically by means of gas outlet valve 294, gas inlet valve 291, and/or other valves. In some embodiments, gas outlet valve 294 on the gas outlet side may be used to maintain pressure within the gas exchanger unit by working in conjunction with gas inlet valve 291.

System Flowcharts

FIG. 8 is a flowchart of example gas delivery process according to various embodiments herein. In some embodiments, these steps of the gas delivery system occur before the gases are introduced into the gas exchange unit. In some embodiments, the gas delivery unit supplies a gas mixture at a defined pressure and temperature to a gas exchange unit. In some embodiments, gas is pressurized by an air pump or by a medical facility's air and oxygen supply, or from external gas tanks. In some embodiments, a heater and/or heat exchanger heats up gas to the desired or required temperature. In some embodiments, gas is filtered for impurities prior to entering the gas exchanger. In some embodiments, gas pressure in the system is regulated with one or more control valve as discussed above. In some embodiments, temperature, gas flow rate, and gas concentrations are constantly monitored with various sensors. In some embodiments, the gas delivery unit delivers an adjustable oxygen supply to the gas exchange unit in order to enable sufficient blood oxygenation to a level needed by patient metabolism. In some embodiments, the gas delivery unit can deliver, for example, up to about 100 $cm^3$ per minute. In some embodiments, the gas delivery unit can deliver, for example, around 1, around 2, around 3, around 4, around 5, around 10, around 25, around 50, around 100, around 200, or around 500 $cm^3$ per minute.

In some embodiments, at 415, gases, such as, for example, oxygen, nitrogen, ambient air, and the like may be introduced via gas tanks and/or pumps. In some embodiments, at 420, the gases may be blended and/or mixed via a blender, as discussed herein. In some embodiments, at 425, the gases may be filtered by, for example, a membrane filter. In some embodiments, at 430, the gas quality may be monitored, for example, via an analyzer. In some embodiments, at 435, may be heated via a heater as discussed here. In some embodiments, at 440, the gas temperature, pressure and flow rate may monitored and/or adjusted via instructions from the control unit 165 before entering gas exchange unit.

FIG. 9 is a flowchart of an example fluid delivery process according to various embodiments herein. In some embodiments, these steps of the fluids delivery unit may occur before the fluids enter the gas exchange unit 110. In some embodiments, Heparin and nutrients stored in disposable cartridges of corresponding volume may be used for delivery directly into an arterial catheter, before the catheter enters a capillary tree of the gas exchanger. In some embodiments, an amniotic fluid disposable cartridge of corresponding volume may be used for amniotic fluid oral administration. In some embodiments, fluids may be delivered with metering pumps. In some embodiments, flow rates may be constantly measured and controlled by a control unit.

In some embodiments, at 445, nutrients, heparin (or other anti-coagulants), and/or simulated amniotic fluid may be introduced in cartridges. In some embodiments, at 450, the levels of each fluid may be monitored via level sensors controlled by a control unit 165. In some embodiments, at 455, nutrients and heparin may be pumped into the gas exchanger 110. In some embodiments, at 460, the amniotic fluid may be pumped to the infant, as discussed herein.

Figure 10:
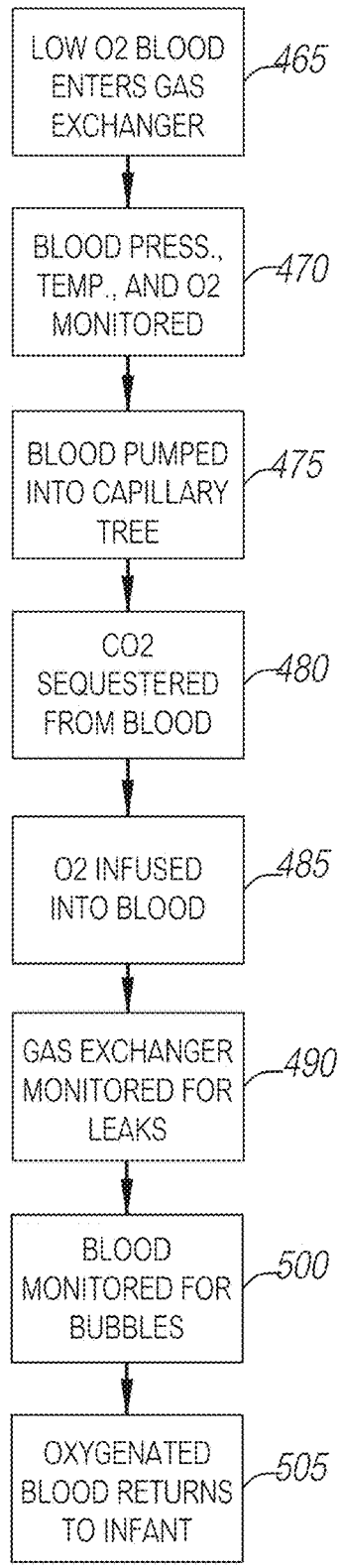
FIG. 10 is a flowchart of example gas exchange process according to various embodiments described herein.

FIG. 10 is a flowchart of an example gas exchange process according to various embodiments described herein. In some embodiments, a gas exchange unit (GEU) may serve as a blood-gas (e.g. $O_2$ and $CO_2$) exchange unit. In some embodiments, it may also serve as a heat exchanger, wherein blood is warmed by gas flowing through the gas exchanger. In some embodiments, gas directed to the gas exchangers may be a mixture of controlled proportions of air and oxygen. In some embodiments, the gas exchanger is divided into a blood side and a gas side. In some embodiments, the unit comprises a membrane exchanger, wherein blood flows through hollow fibers, and wherein the gas flows around the hollow fibers in a perpendicular direction to the flow path of the blood. In some embodiments, blood flows from the arterial line, through an inflow capillary tree (i.e. Afferent Capillary Unit). In some embodiments, from the inflow capillary tree, blood enters the hollow fibers, where gas exchange and warming of the blood occurs. In some embodiments, blood flows through the hollow fibers to an outflow capillary tree (i.e. Efferent Capillary Unit) and eventually into a venous line. In some embodiments, gas temperature and pressure inside the gas exchange unit are measured and controlled continuously. In some embodiments, the unit is equipped with a blood leak detection sensor. In some embodiments, the inflow capillary tree and outflow capillary tree may be designed to mimic natural blood vessels. In some embodiments, the inflow capillary tree and outflow capillary tree may comprise branching with branching angles and shapes of capillaries resembling the natural configuration of human blood vessel/capillaries branching In some embodiments, at 465, low-oxygen infant blood may enter the gas exchanger. In some embodiments, at 470, blood pressure, temperature and/or oxygen levels may be monitored. In some embodiments, at 475, the blood may be transmitted into an inflow capillary tree. In some embodiments, at 480, carbon dioxide may be sequestered from the blood. In some embodiments, at 485, oxygen may be infused into the blood through a membrane exchange, as discussed herein. In some embodiments, at 490, the gas exchanger may be monitored for leaks via a leak detection system. In some embodiments, at 500, the blood may be monitored for bubbles and/or bubbles may be removed from the blood. In some embodiments, at 505, oxygenated blood may be returned to an infant by way of, for example, the umbilical cord.

Figure 20:
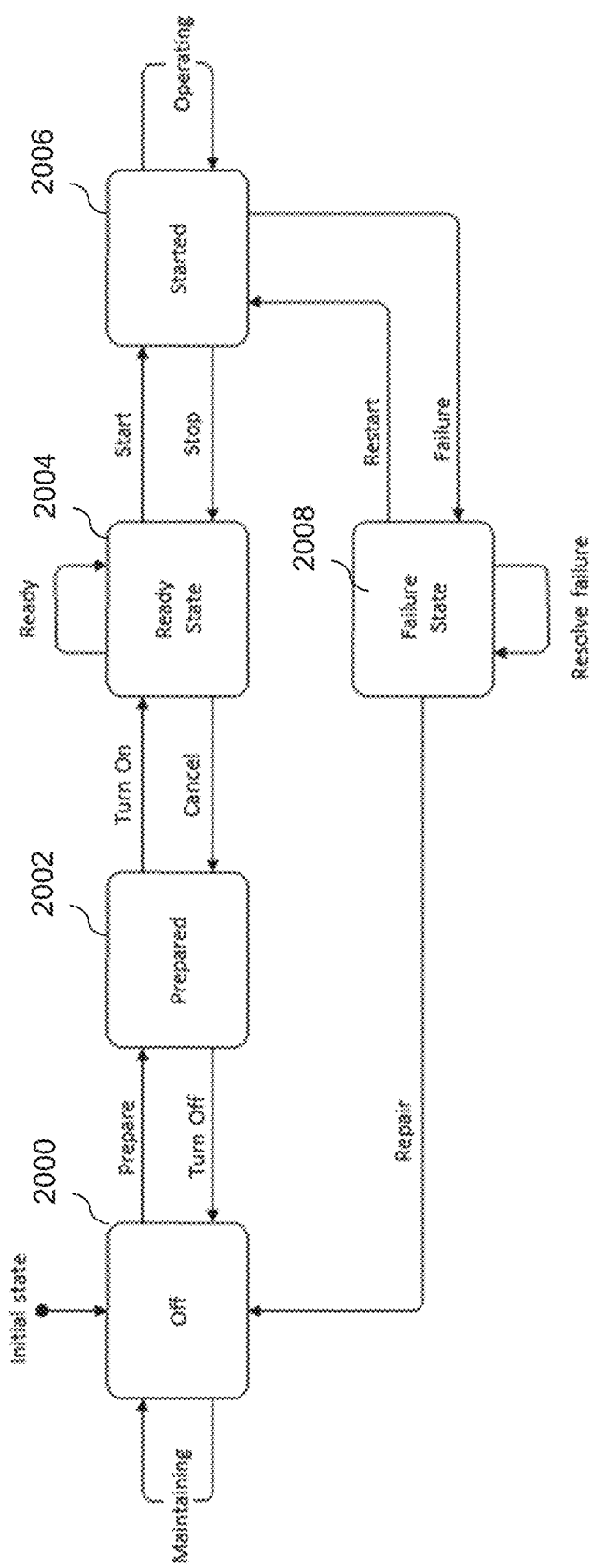
FIG. 20 illustrates a state diagram of an abstract representation of the behavior of the artificial placenta systems described herein.

FIG. 20 illustrates a state diagram of an abstract representation of the behavior of the artificial placenta systems described herein. The system may start in an initial state. In some embodiments, the initial state may be off state 2000 at which the artificial placenta system is off and not running. In some embodiments, the artificial placenta system may maintain its off state until it is instructed by a user to go into a prepared state 2002, in which the artificial placenta system will prepare to run. In some embodiments, the system will remain in a prepared state until it is turned off, returning the system to an off state 2000, or it is turned on. In some embodiments, when the system is turned on, it will enter a ready state 2004, in which the system is ready start the oxygenation of a patient's blood. The system may maintain in the ready state 2004 until it is cancelled (e.g. by a user input or timeout), at which time the system may return to a prepared state 2002, or until the system is started (e.g. by a user or after a predetermined period of time) and enters a started state 2006. In some embodiments, the system may operate and maintain a started state 2006 until it is stopped (e.g. by a user), returning the system to a ready state 2004, or until a system failure occurs. If a system failure occurs, the system may enter a failure state 2008. In some embodiments, the system may remain in a failure state until it is restarted or until it is repaired. In either case, the system may move to an off state 2000 or a started state 2006. In other embodiments, the system may return to a prepared state 2002 or a ready state 2004 upon restarting or repair.

Figure 21:
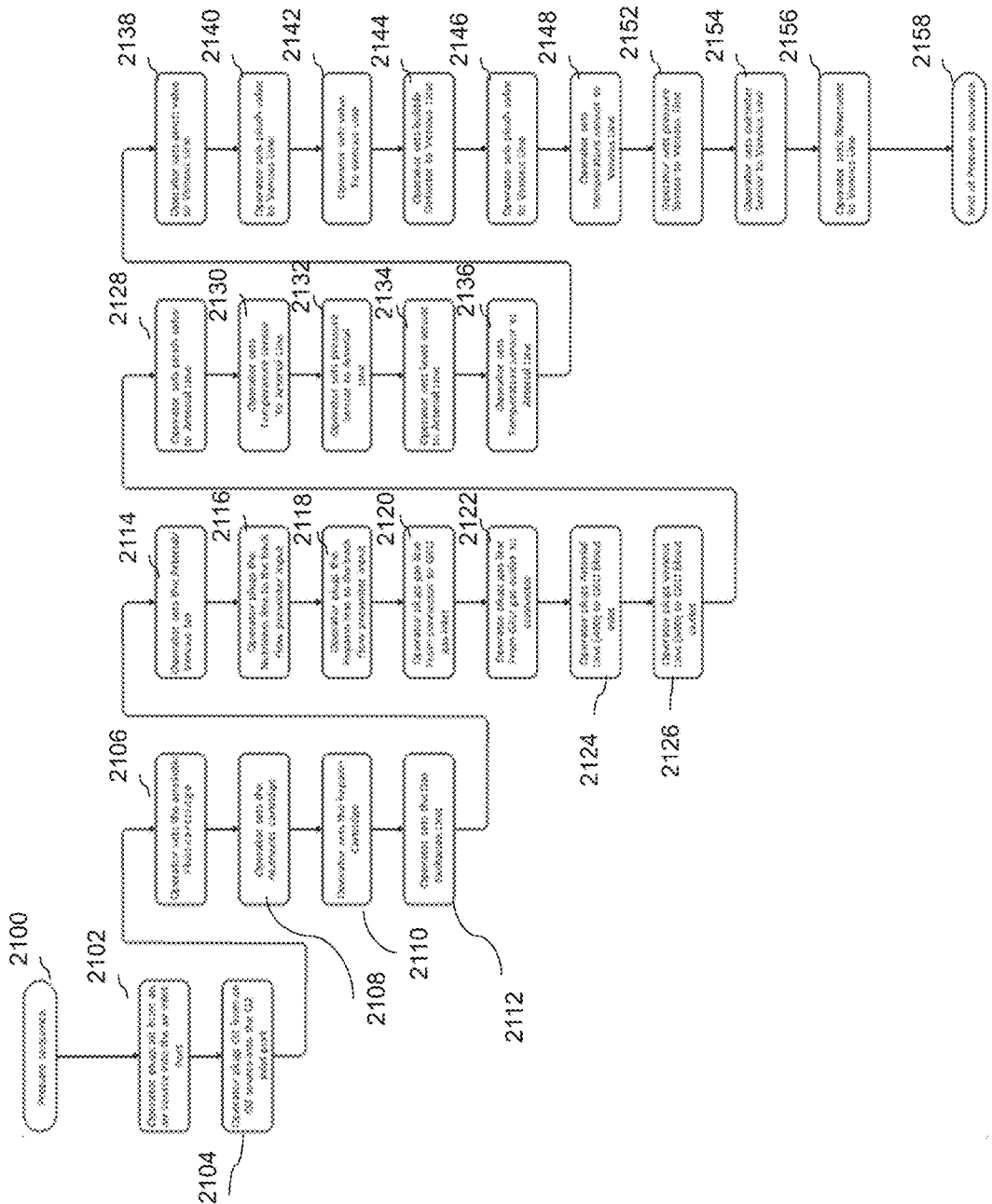
FIG. 21 illustrates an example flowchart of the steps that an operator may perform to bring an artificial placenta system from an initial state "Off" to the state "Prepared" according to various embodiments herein.

FIG. 21 illustrates an example flowchart of the steps that an operator may perform to bring an artificial placenta system from an initial state "Off" to the state "Prepared" according to various embodiments herein. A prepare sequence 2100 may begin with an operator plugging air from an air source into an air inlet port of the artificial placenta system at 2102. In some embodiments, an operator may plug an oxygen line from an oxygen source into an oxygen inlet port of the artificial placenta system at 2104. In some embodiments, at 2106, the operator may prepare an amniotic fluid cartridge for use by the artificial placenta system. In some embodiments, at 2108, the operator may prepare a nutrient fluid cartridge for use by the artificial placenta system. In some embodiments, at 2110, the operator may prepare a heparin cartridge for use by the artificial placenta system. In some embodiments, at 2112, the operator may prepare the gas exchange unit, as discussed herein, for use by the artificial exchange system. In some embodiments, the operator, at 2114, may prepare the arterial and/or venous lines for use by the artificial placenta system. In some embodiments, at 2116, the operator may plug a nutrients fluid line into a back flow preventer input. In some embodiments, at 2118, the operator may plug a heparin fluid line into a back flow preventer input. In some embodiments, at 2120, the operator may plug a gas line from a connector to an inlet of the gas exchange unit of an artificial placenta system. In some embodiments, at 2122, the operator may plug a gas from a gas outlet of the gas exchange unit to a connector. In some embodiments, at 2124, the operator may plug an arterial to the gas exchange unit blood inlet. In some embodiments, at 2126, the operator may plug a venous line into the gas exchange unit blood outlet port. In some embodiments, at 2128, the operator may set a pinch valve on the arterial line. In some embodiments, at 2130, the operator may set a temperature sensor on the arterial line. In some embodiments, at 2132, the operator may set a pressure sensor on the arterial line. In some embodiments, at 2134, the operator may set a level sensor on the arterial line. In some embodiments, at 2136, the operator may set another temperature sensor at second location along the arterial line. In some embodiments, at 2138 and 2140, the operator may set pinch valves at one or more locations along the venous line. In some embodiments, at 2142 the operator may prepare one or more valves along the venous line. In some embodiments, at 2144, the operator sets a bubble detectors along the venous line. In some embodiments, at 2146, the operator may set one or more additional pinch valves along the venous line. In some embodiments, at 2148, the operator may set one or more temperature sensors on the venous line. In some embodiments, at 2152, the operator may set one or more pressure sensors on the venous line. In some embodiments, at 2154, the operator may set one or more oximeter sensors on the venous line. In some embodiments, at 2156, the operator may set one or more flow meters on the venous line. In some embodiments, the prepare sequence may be completed at 2158 and the artificial placenta system may enter a "Prepared" state.

Figure 22:
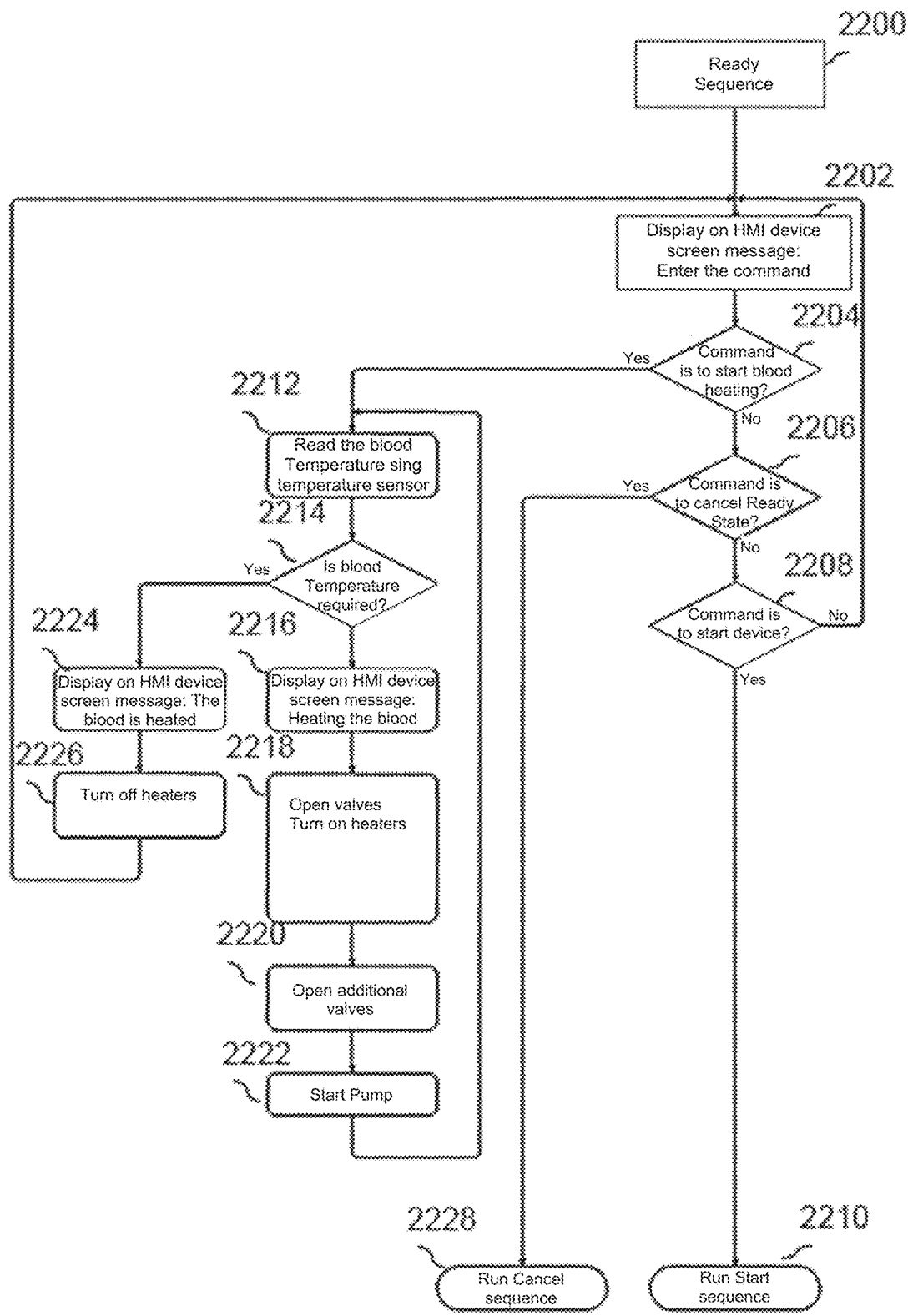
FIG. 22 illustrates an example flowchart of an example process executed while the artificial placenta system is in the "Ready state" according to various embodiments herein.

FIG. 22 illustrates an example flowchart of an example process executed while the artificial placenta system is in the "Ready state" according to various embodiments herein. In some embodiments, the process may lead the system to the "Started" state using a "Start" command, or return the system to the "Prepared" state using the "Cancel" command. Optionally, in some embodiments, blood warming can be performed.

In some embodiments, at 2200, the "Ready" sequence may be initiated. In some embodiments, at 2202, a message may be displayed on the human machine interface (HMI_of the artificial placenta system prompting an operator to enter a command, such as "enter the command." In some embodiments, at 2204, the system may determine if an operator has commanded the system to start a blood heating process. In some embodiments, at 2206, if the system determines that the operator has not commanded the system to start blood heating, the system may determine if an operator has commanded the system to cancel the "Ready" state of the system. In some embodiments, at 2208, if the system determines that the operator has not commanded the system to cancel the "Ready" state, the system may determine if an operator has commanded the system to start the artificial placenta. In some embodiments if the system determines that the operator has commanded the system to start the artificial placenta, the system may begin a "Start" sequence at 2210. In some embodiments, if the system determines that the operator has not commanded the system to start the artificial placenta, the process may return to step 2202 to determine an operator command.

If, at 2204 the system determines that the operator has commanded the system to start blood heating, the system may read the blood temperature using one or more temperature sensors at 2212. In some embodiments, at 2214, the system may determine if the blood temperature is at a predetermined threshold level. In some embodiments, if the system determines that the blood temperature has not reached the predetermined threshold level, the system may display, via the HMI, that the blood is being heated by, for example, a message displaying "heating the blood at 2216. In some embodiments, at 2218, the system and/or an operator may open one or more gas, fluid, and/or blood valves and turn on one or more heaters, as described herein, to heat the blood. In some embodiments, at 2220, the system and/or the operator may open additional gas, fluid, and/or blood valves to further the heating of the blood. In some embodiments, at 2222 the system and/or an operator may start one or more blood, fluid, and/or gas pumps of the system. In some embodiments, once the one or more pumps have been started and/or running for a predetermined period of time, the system may again read the blood temperature at 2212 and determine if the temperature of the blood has reached a predetermined threshold level at 2214. If, at 2214, the system determines that the blood temperature has reached the predetermined threshold level, the system may display, via the HMI, a message notifying an operator that the blood has been heated by, for example, a message reading "the blood is heated" at 2224. In some embodiments, at 222, the one or more heaters may be turned off. In some embodiments, once the heaters have been turned off the process may return to step 2202 to prompt an operator command.

In some embodiments, if, at 2206, the system determines that the operator has entered a command to cancel the "Ready" state, the system may run a "Cancel" sequence at 2228 to return the artificial placenta to a "Prepared" state.

Figure 23:
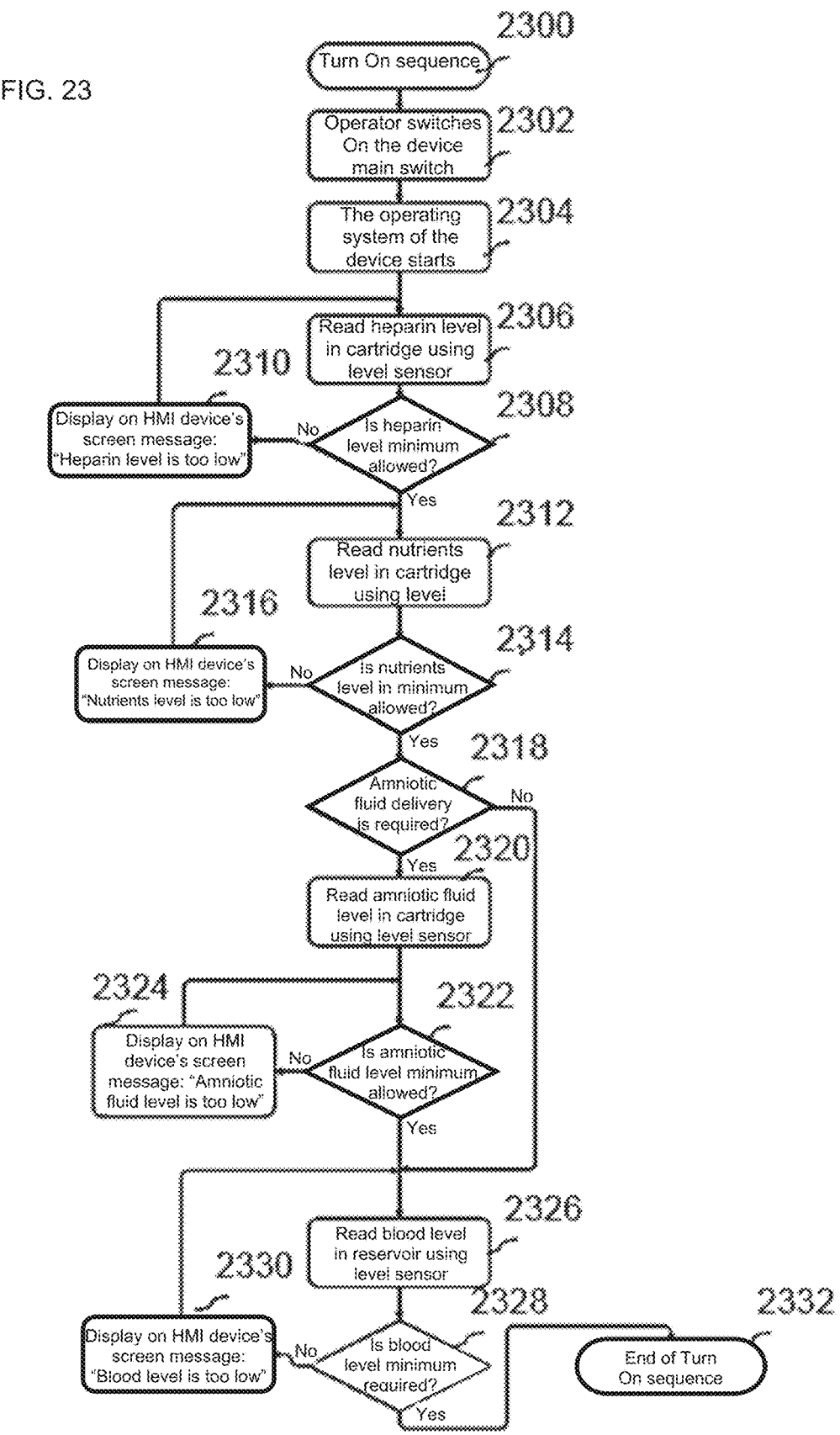
FIG. 23 illustrates a flowchart for a process of transferring the artificial placenta system from a "Prepared" State to a "Ready" state according to various embodiments herein.

FIG. 23 illustrates a flowchart for a process of transferring the artificial placenta system from a "Prepared" State to a "Ready" state according to various embodiments herein. In some embodiments, art 2300, a "Turn On" sequence may be initiated. In some embodiments, at 2302, an operator may turn the artificial main switch to an "On" configuration. In some embodiments, at 2304, the operating system of the artificial placenta system may start. In some embodiments, at 2306, the Heparin level in a Heparin cartridge may be measured using a level sensor. In some embodiments, at 2308, the system may determine whether the heparin level is above a minimum allowed level. In some embodiments, if the heparin level is determined by the system to be lower than the minimum allowed level, the system, at 2310, may prompt the operator to refill or replace the Heparin cartridge by displaying a message (e.g. "Heparin level is too low") to the operator via the HMI. In some embodiments, after a preset amount of time from displaying the message or upon detecting a replacement cartridge, the system may return to step 2306 to measure the heparin level.

If, at 2308, the system determines that the Heparin level is above the minimum allowed level the system may, at 2312, measure the nutrient level in a nutrient cartridge using a level sensor. In some embodiments, at 2314, the system may determine whether the nutrient level is above a minimum allowed level. In some embodiments, if the nutrient level is determined by the system to be lower than the minimum allowed level, the system, at 2316, may prompt the operator to refill or replace the nutrient cartridge by displaying a message (e.g. "nutrient level is too low") to the operator via the HMI. In some embodiments, after a preset amount of time from displaying the message or upon detecting a replacement cartridge, the system may return to step 2312 to measure the nutrient level.

If, at 2314, the system determines that the nutrient level is above the minimum allowed level the system may, at 2318, determine if amniotic fluid delivery is required, which may be the case when the artificial placenta is used in conjunction with an amniotic bed or air incubator, or as an independent system. In some embodiments, if the system determines the amniotic fluid delivery is required, the system may, at 2320, measure the amniotic fluid level in an amniotic fluid cartridge using a level sensor. In some embodiments, at 2322, the system may determine whether the amniotic fluid level is above a minimum allowed level. In some embodiments, if the amniotic fluid level level is determined by the system to be lower than the minimum allowed level, the system, at 2324, may prompt the operator to refill or replace the amniotic fluid cartridge by displaying a message (e.g. "amniotic fluid level is too low") to the operator via the HMI. In some embodiments, after a preset amount of time from displaying the message or upon detecting a replacement cartridge, the system may return to step 2320 and/or 2322 to measure the nutrient level and determine if the amniotic fluid level is above the minimum allowed level.

In some embodiments, if the system determines that the amniotic fluid level is above the minimum allowed level or that the amniotic fluid delivery is not required, the system may, at 2326, measure the blood level in a blood reservoir using a level sensor. In some embodiments, at 2328, the system may determine whether the blood level is above a minimum allowed level. In some embodiments, if the blood level is determined by the system to be lower than the minimum allowed level, the system, at 2330, may prompt the operator t take necessary steps to increase blood flow through the system by displaying a message (e.g. "blood level is too low") to the operator via the HMI. In some embodiments, the system may return to step 2326 to measure the blood level and determine if the blood level is above the minimum allowed level. In some embodiments, if the blood level is determined by the system to be above the minimum allowed level, the "Turn On" sequence may be completed at 2332. In some embodiments, completion of the Turn-On sequence may result in the artificial placenta system moving from a "Prepared" state to a "Ready" state.

Figure 24:
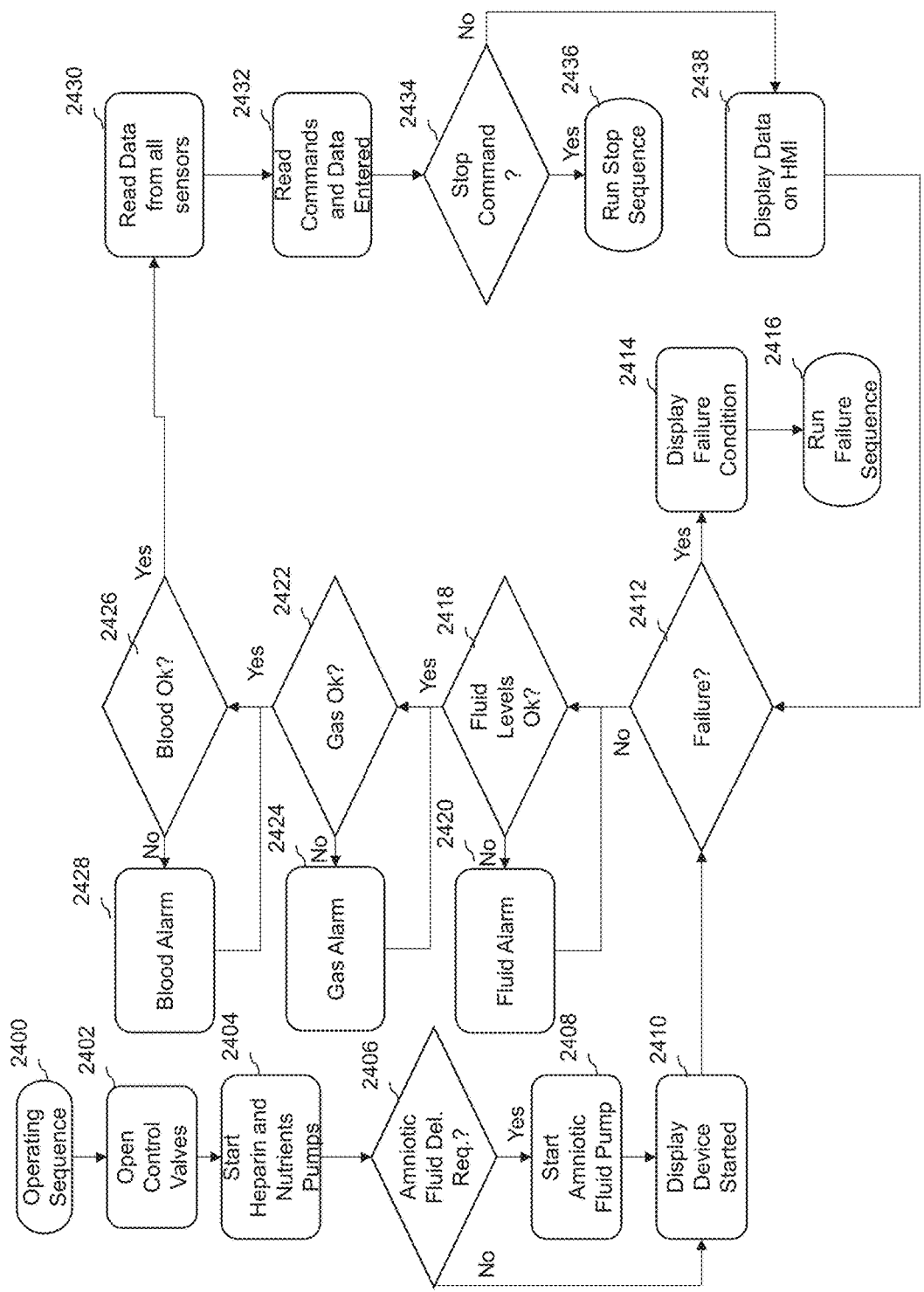
FIG. 24 illustrates a flowchart of an example operating sequence of the artificial placenta system according to various embodiments herein.

FIG. 24 illustrates a flowchart of an example operating sequence of the artificial placenta system according to various embodiments herein. In some embodiments, this sequence is executed while the artificial placenta system is in the "Started" state. In some embodiments, this sequence can lead the system to the "Failure" state if a failure occurs, or return the system to the "Ready state" using the "Stop" command. In some embodiments, the artificial placenta device first checks possible failures in the system. In some embodiments, the device then checks the appropriate parameters and, if necessary, issues appropriate warnings, or performs appropriate corrections according to, for example pre-set parameters. Finally, in some embodiments, the device displays all the necessary values via the HMI, and executes the commands assigned by the operator.

In some embodiments, an operating sequence 2400 may be initiated. In some embodiments, at 2402, various control valves may be opened to begin and/or increase blood/gas flow into the artificial placentas system. In some embodiments, at 2404, the heparin and nutrients pumps may be started to begin nutrient and heparin flow into the artificial placenta system. In some embodiments, the system, at 2406, may determine if amniotic fluid delivery is required, which may be the case when the artificial placenta is used in conjunction with an amniotic bed or air incubator, or used as an independent system. In some embodiments, at 2408, if amniotic fluid delivery is determined to be required, an amniotic fluid pump may be started to initiate the flow of amniotic fluid into the artificial placenta system. In some embodiments, at 2410, if the system determines that amniotic fluid delivery is not required, or after the amniotic fluid pump has been started, the system may display a notification via the HMI that the artificial placenta system has started (e.g. "device started).

In some embodiments, at 2412, the system will initiate a series of failure checks to determine if any failure states are present such that the system would need to be restarted or repaired (i.e. failure state). In some embodiments, the system, 2412, may check for one or more of the following example failure states: detection of gas bubbles in the blood by a bubble detector, unacceptable deviation in preset venous line flow rate, unacceptable deviation in preset venous line oxygenation level, unacceptable deviation in arterial line pressure, unacceptable deviation venous line pressure, unacceptable deviation in arterial line temperature, unacceptable deviation in venous line temperature, blood leakage above an acceptable value, any blood leakage in the gas exchanger, unacceptable deviation in gas exchanger gas temperature, unacceptable deviation in oxygenation level of gas exchanger gas mixture, and/or unacceptable gas temperature, among others.

In some embodiments, if a failure is detected at 2412, the system, at 2414 may display, via the HMI, a failure condition notification to the operator to alert the operator of the failure. For example, the failure condition notification may comprise one or more of the following messages: Gas Bubble in Blood, Venous Line Flow Rate, Venous Line Oxygen Level, Arterial Line Pressure Level, Venous Line Pressure Level, Arterial Line Temperature Value, Venous Line Temperature Value, Blood Leakage in GEU, GEU Gas Pressure Level, GEU Gas Temperature Value, GEU Oxygenation Level, Gas Temperature Value.

In some embodiments, if a failure is detected at 2412, the system may enter into a failure sequence 2416, which may require restarting the system and/or repair of the system.

In some embodiments, at 2418, the system may begin checking appropriate parameters of the system, including fluid levels. For example, the system may be configured to check the Heparin, nutrient, and/or amniotic fluid levels using level sensors as described in detail above with regard to FIG. 23. In some embodiments, at 2420, the system may be configured to display and/or set off one or more auditory and/or visual alarms notifying an operator regarding the insufficient fluid levels. In some embodiments, the system may also stop one or more fluid pumps if low fluid levels are detected. In some embodiments, after one or more fluid pumps are stopped and fluid levels are returned to adequate levels, the alarms may be shut off or removed from the HMI and the one or more fluid pumps may be restarted.

In some embodiments, at 2422, the system may check various properties of the gas in the artificial placenta system, for example, pressure, flow level, and oxygen levels in the gas supply and/or gas delivery unit using pressure sensors, flow meters, and/or gas analyzers. In some embodiments, when the measured values fall outside acceptable values, one or more auditory and/or visual alarms may be displayed and/or set off at 2424 to alert an operator of the unacceptable gas properties. In some embodiments, once the gas properties have been restored to acceptable levels, the one or more alarms may be removed from the HMI and/or shut off.

In some embodiments, at 2426, the system may check various blood parameters of the artificial placenta system. For example, properties such as the blood level in the blood reservoir, the blood flow rate measured by a flow meter, blood oxygenation level measured by an oximeter, and/or blood temperature measured by one or more temperature sensors may be checked by the system. In some embodiments, at 2428, if one or more of the blood parameters falls outside an acceptable range, one or more alarms may be displayed and/or set off to alert an operator of the unacceptable blood properties. In some embodiments, once the blood properties have been restored to acceptable levels, the one or more alarms may be removed from the HMI and/or shut off. In some embodiments, the system may automatically provide useful system data to the operator and/or take appropriate steps to correct any unacceptable deviation in blood parameters. For example, if the blood flow rate differ from a set value, the system may calculate the appropriate rounded hydrostatic height value for the bubble trap and provide that information to the operator via the HMI. Additionally, if blood oxygenation and/or blood temperature values fall outside of acceptable ranges, the system may automatically correct the oxygenation by adjustment of various gas valves in the gas delivery and/or gas exchange units.

In some embodiments, at 2430, if the system determines that the fluid, gas, and blood parameters of the system are acceptable, the system may collect and aggregate the various data from the sensors and meters throughout the artificial placenta system. Also, at 2432, the system may read and execute any commands, data, and/or parameters entered by the operator at, for example, the HMI. In some embodiments, at 2434, the system may determine if the operator has entered a "Stop" command into the system. If the system determines that a "Stop" command has been entered, the system may initiate a stop sequence at 2436 to cease the operation sequence.

In some embodiments, if no "Stop" command has been entered, the system, at 2438, may display, via the HMI, one or more data points and/or parameters of the artificial placenta system. For example, the system may display one or more of the following values: arterial line blood temperature, arterial line blood, venous line blood temperature, venous line blood pressure, venous line flow rate, venous blood oxygen level, gas exchange unit gas pressure level, gas exchange unit gas temperature, Heparin flow rate, nutrients flow rate, amniotic fluid flow rate, oxygen and carbon dioxide levels at the gas input, and/or oxygen and/or carbon dioxide levels at the gas output, among others. In some embodiments, if no stop command is entered, the process may return to step 2412 to check for failure states and system parameters and continue the operational sequence.

Fluid Injection

Pre-term infants can be accustomed to a far different environment for growth than term infants. As a non-limiting example, a term infant can rely on his or her lungs for oxygenation and gastrointestinal system for nutrition. In contrast, an in-utero fetus can receive oxygenation and nutrition through the placenta while the lungs, oral cavity, sinuses, auditory system and/or gastrointestinal tracts are flooded with amniotic fluid. The constant breathing motion of diaphragm in-utero can constantly pump amniotic fluid in and/or out of the lungs while an in-utero fetus swallows and fills the gastrointestinal tract with amniotic fluid. The auditory canal and middle ear of an in-utero infant can also be flooded with amniotic fluid. As such, in order to more closely simulate an in-utero environment, it can be advantageous to fill the lungs and/or gastrointestinal tract of a pre-term infant with synthetic or simulated amniotic fluid.

In order to fill the oral cavity, nasal cavity, lungs and/or gastrointestinal cavity of an infant, some embodiments can involve submerging a pre-term infant completely in synthetic or simulated amniotic fluid. However, one concern can be that body fluids (e.g. urine), skin tissue, hair and other certain manipulations by medical staff of the infant can cause contamination of the synthetic or simulated amniotic fluid, which can lead to bacterial pneumonitis, a potentially life-threatening infection of the lungs. For example, bacterial pneumonitis can develop secondary to pumping of contaminated simulated amniotic fluid in and/or out of the lungs by the motion of the diaphragm of the infant.

In order to address this concern, in certain embodiments, a sterile plastic bag or other containment device can be provided to contain the pre-term infant and simulated amniotic fluid. The sterile plastic bag or other containment device can be zipped or otherwise closed for the duration of the pre-term infant's submersion in order to prevent contamination of the fluid. Such embodiments, however, may not be fully compatible with needs of a hospital or medical facility setting in which medical staff may require constant or periodic access to the pre-term infant, thereby increasing risk of contamination of the amniotic fluid in which the pre-term infant is submerged in.

As such, some embodiments of the systems, devices, and/or methods for simulated or synthetic amniotic fluid injection can be configured to be compatible with one or more amniotic bath incubators described herein that allow an infant to be partially submerged in synthetic or simulated amniotic fluid. In other words, certain embodiments the systems, devices, and/or methods for simulated or synthetic amniotic fluid injection can be used to supply amniotic fluid to a pre-term infant that is partially, as opposed to completely, submerged in simulated or synthetic amniotic fluid with the head and/or neck of the infant placed above the fluid level. For example, in some embodiments, the system can comprise one or more tubes that are configured to provide and/or fill or at least partially fill the lungs and/or gastrointestinal system of a pre-term infant placed inside an amniotic bath incubator with the head and/or neck of the infant above the fluid level.

Figure 11:
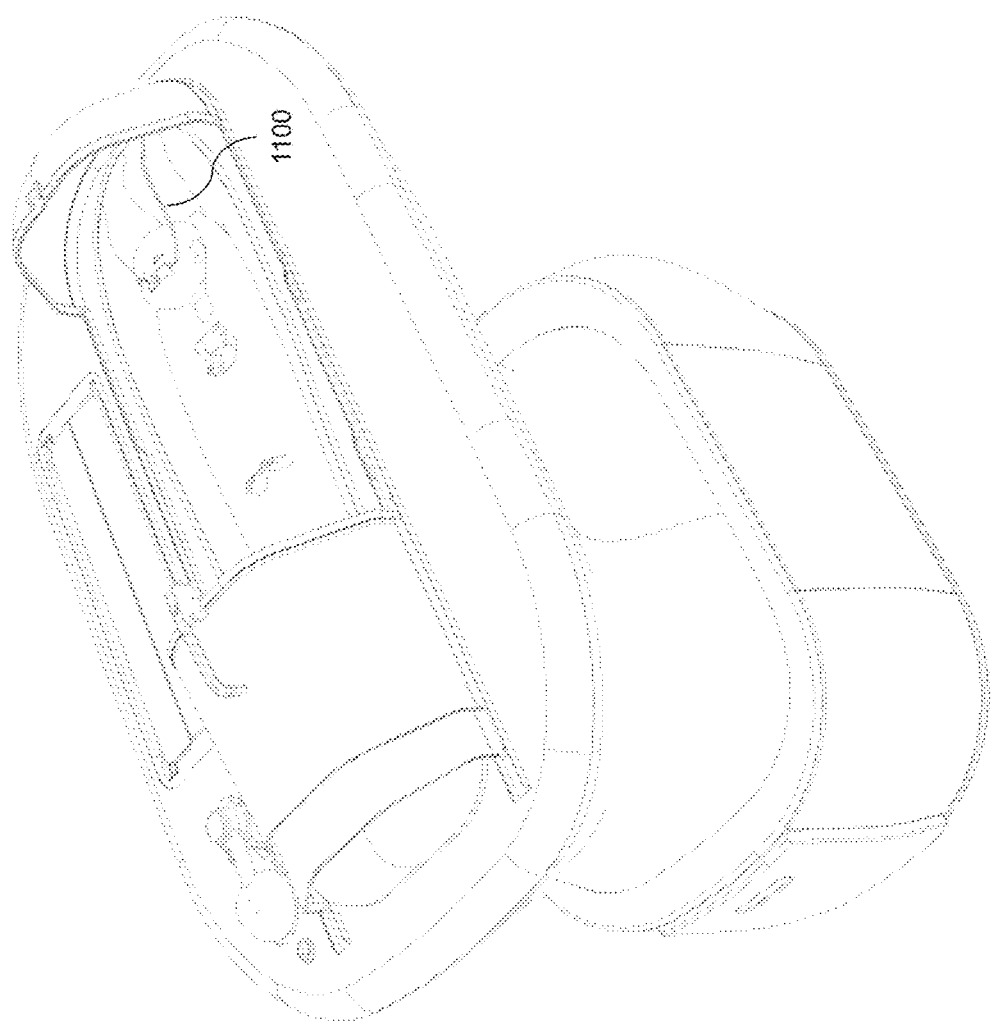
FIG. 11 illustrates a perspective view of an infant placed inside an embodiment of an amniotic bath incubator with an embodiment of a simulated amniotic fluid injector.

FIG. 11 illustrates a perspective view of an infant placed inside an embodiment of an amniotic bath incubator with an embodiment of a simulated amniotic fluid injector. In the embodiment illustrated in FIG. 11, an infant can be placed inside an amniotic bath incubator as described herein, with the infant's head and/or neck placed above the fluid level of the incubator. Certain embodiments of an amniotic fluid injection system 1100 can comprise one or more tubes for supplying simulated or synthetic amniotic fluid from an amniotic bath incubator to the pre-term infant's oral and/or nasal cavity, for example in order to flood the infant's nasopharynx, nasal cavity, sinuses, Eustachian tube, middle ear cavity, mastoids, oropharynx, hypopharynx, lungs and/or gastrointestinal system with simulated amniotic fluid. In other words, in some embodiments, an amniotic fluid injection system 1100 can be configured to be attached to the mouth and/or nose of an infant to fill the oral and/or nasal cavity of the infant with simulated amniotic fluid, for example while the infant is oxygenated through the umbilical vessels and nutrition is provided through the umbilical vein and/or using total parenteral nutrition.

Figure 15:
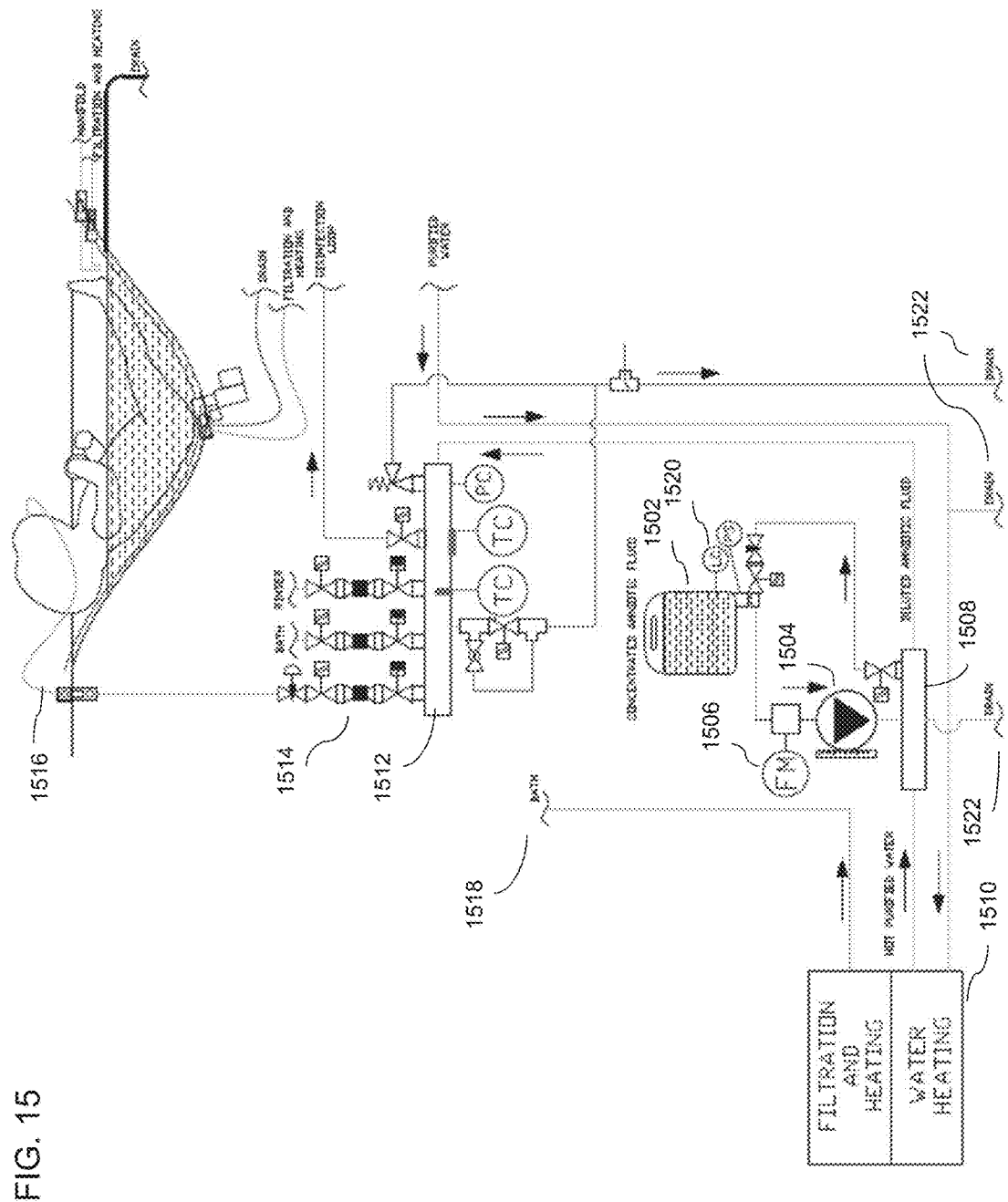
FIG. 15 is a block diagram depicting an embodiment of a simulated amniotic fluid injection system as part of amniotic bed device.

In embodiments, as shown in FIG. 6 and FIG. 7, simulated or synthetic amniotic fluid may distributed by a fluid delivery system of the artificial placenta system. In some embodiments, simulated or synthetic amniotic fluid can be created by an amniotic incubator through purified water warmed and combined with a concentrated crystalloid solution containing concentrated electrolytes and/or minerals with producing synthetic or simulated amniotic fluid for the amniotic bath incubator, as shown in FIG. 15. For example, a programmable dosing pump can be used to combine a concentrated solution containing concentrated electrolytes and/or minerals to create a simulated or synthetic amniotic fluid with osmolality, pH, electrolyte, and/or mineral balances matching, substantially matching, or mimicking physiologic amniotic fluid, which can be required by medical staff, and/or similar to balances in amniotic fluid at the gestation age of an infant.

In some embodiments, one end of one or more tubes of an amniotic fluid injection system 1100 can be configured to be attached to one or both nostrils and/or the mouth of an infant. Another end of the one or more tubes can be configured to be attached to an outlet of a source of simulated or synthetic amniotic fluid. A pump and/or other device(s) can be used to constantly, continuously, and/or periodically drip or provide fluid into the oral and/or nasal cavity of an infant, for example to flood the lungs, auditory canal, middle ear and/or gastrointestinal tract.

In certain embodiments, one or more tubes of an amniotic fluid injection system 1100 can comprise and/or be made of a non-toxic and/or biocompatible material for delivering fluids. In some embodiments, an amniotic fluid injection system 1100 can comprise one or more straps to be used in conjunction with the one or more tubes. For example, the one or more straps can be configured to hold one or tubes in place within the oral and/or nasal cavity of an infant. In some embodiments, excess synthetic or simulated amniotic fluid can be configured to drip from the face of an infant into the amniotic bath incubator and may be drained together with fluid in the incubator in which the infant can be partially submerged in.

Figure 12:
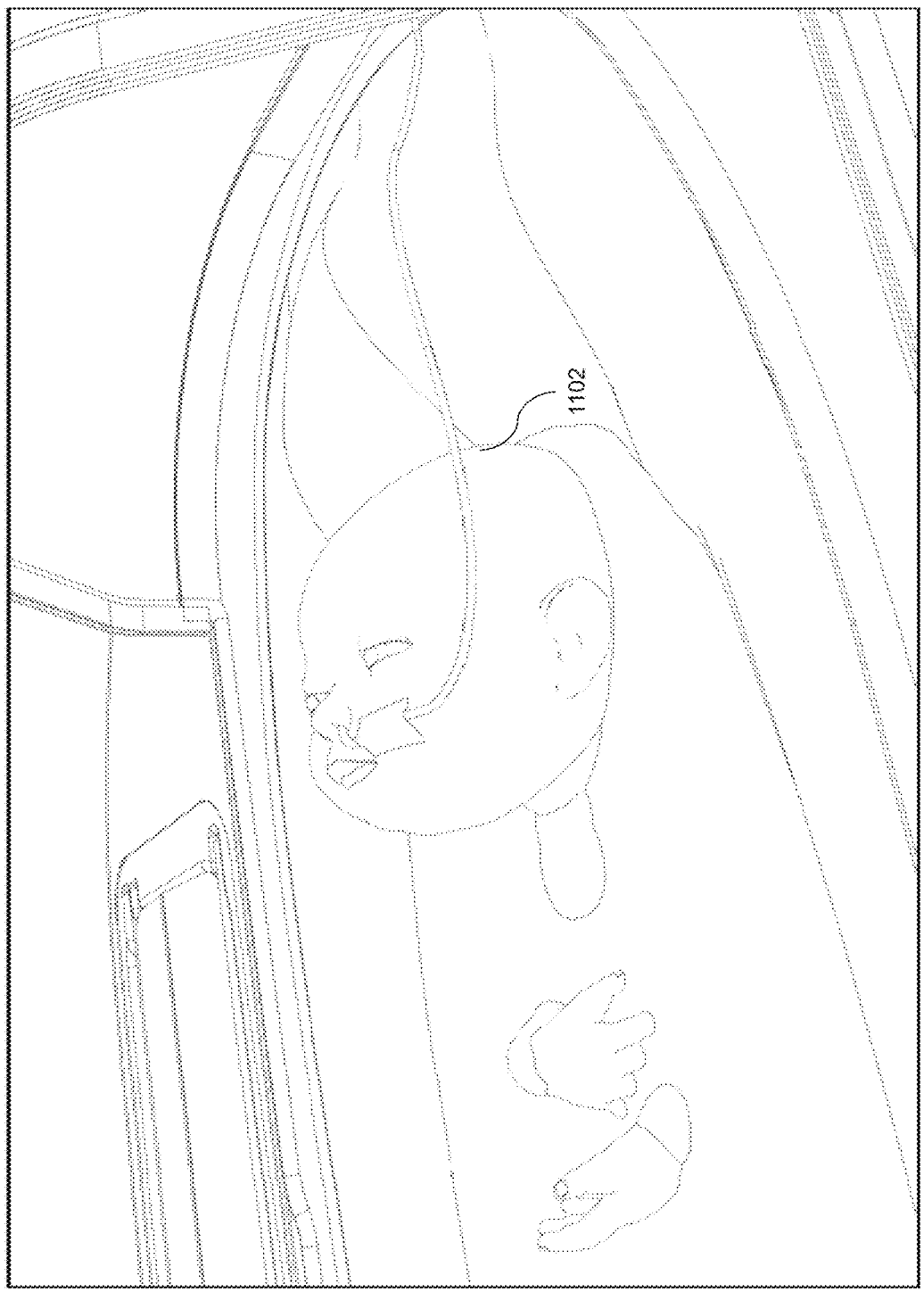
FIG. 12 illustrates a perspective view of an embodiment of a single nostril tube of an example simulated amniotic fluid injector connected to an infant placed inside an embodiment of an amniotic bath incubator.

FIG. 12 illustrates a perspective view of an embodiment of a single nostril tube of an example simulated amniotic fluid injector connected to an infant placed inside an embodiment of an amniotic bath incubator. As illustrated in FIG. 12, in some embodiments, an amniotic fluid injection system can comprise a tube 1102 configured to be coupled or attached to a single nostril of an infant. A single nostril tube 1102 can be configured to provide synthetic or simulated amniotic fluid into the nasal cavity of the infant or a portion thereof. In certain embodiments, an amniotic fluid injection system can comprise two tubes, in which each of the two tubes is configured to be coupled or attached to a nostril of an infant, thereby providing synthetic or simulated amniotic fluid to both nostrils of an infant.

Figure 13:
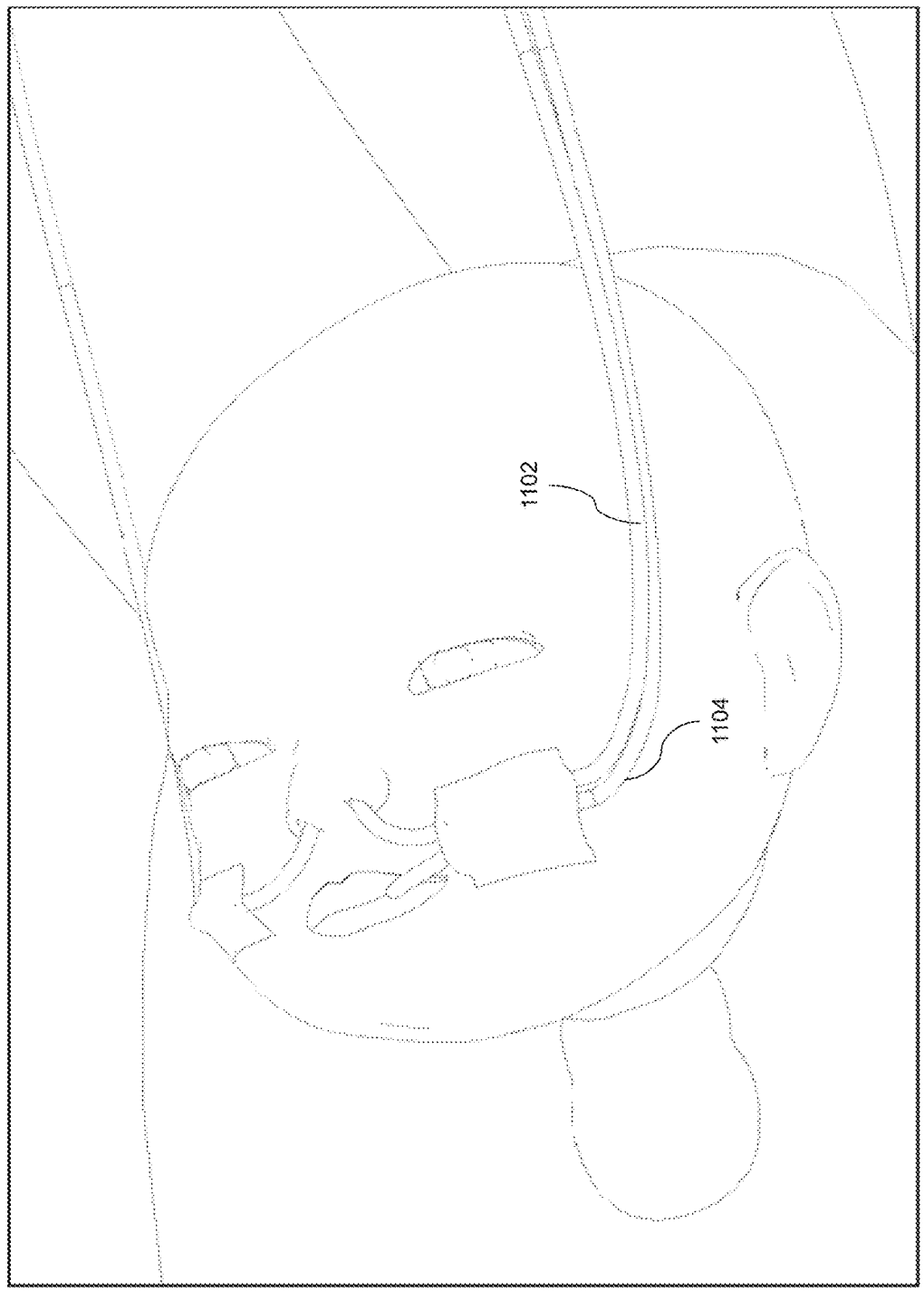
FIG. 13 illustrates a perspective view of an embodiment of double nostril and mouth tubes of an example simulated amniotic fluid injector connected to an infant placed inside an embodiment of an amniotic bath incubator.

FIG. 13 illustrates a perspective view of an embodiment of double nostril and mouth tubes of an example simulated amniotic fluid injector connected to an infant placed inside an embodiment of an amniotic bath incubator. As illustrated, in some embodiments, an amniotic fluid injection system can comprise an additional tube 1104 configured to be coupled or attached to the mouth of an infant to provide synthetic or simulated amniotic fluid to an oral cavity of an infant. As such, in some embodiments, an amniotic fluid injection system can comprise one tube 1102 configured to be coupled or attached to a single nostril of an infant, two tubes 1102 configured to coupled or attached to both nostrils of an infant, two tubes 1102, 1104, of which one is coupled or attached to a single nostril of an infant and the other is coupled or attached to the mouth of an infant, and/or three tubes 1102, 1104, of which two 1102 are coupled or attached to both nostrils of an infant and the third 1104 is couple or attached to a mouth of the infant.

Figure 14:
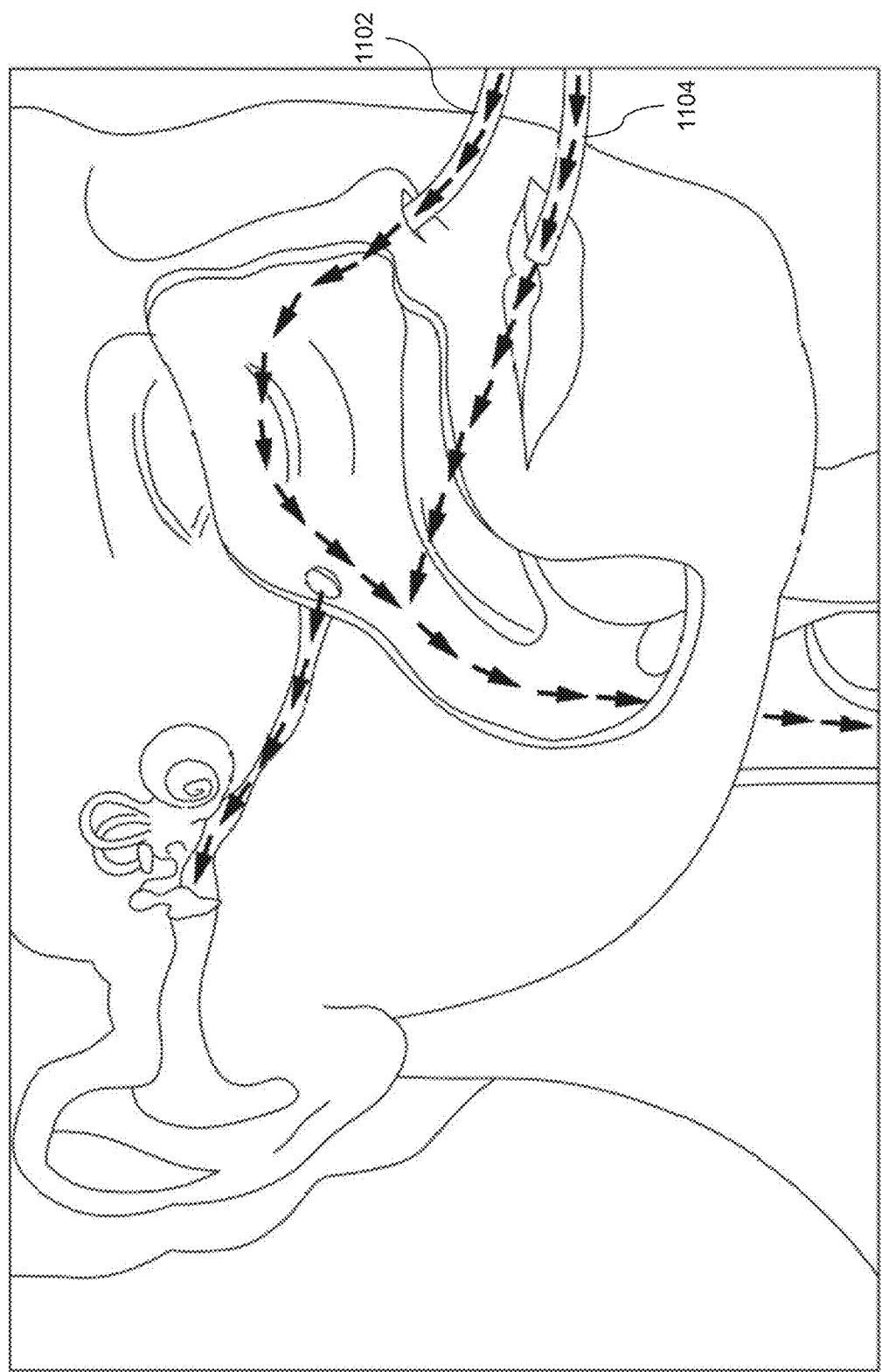
FIG. 14 illustrates a schematic of inner directional arrows of nostril and mouth tubes of an example simulated amniotic fluid injector connected to an infant.

FIG. 14 illustrates a schematic of inner directional arrows of nostril and mouth tubes of an example simulated amniotic fluid injector connected to an infant. As illustrated, a nasal tube 1102 of an amniotic fluid injection system can be configured to provide synthetic or simulated amniotic fluid to a nasal cavity of an infant, and an oral tube 1104 can be configured to provide synthetic or simulated amniotic fluid to an oral cavity of the infant. The injected synthetic or simulated amniotic fluid can flow through the nasal and/or oral cavities of an infant to fill the nasopharynx, nasal cavity, oral cavity, sinuses, Eustachian tube, middle ear cavity, mastoids, oropharynx, hypopharynx, lungs and/or gastrointestinal system with synthetic or simulated fluid.

FIG. 15 is a block diagram depicting an embodiment of a simulated amniotic fluid injection system as part of an amniotic incubator. In some embodiments, a concentrated amniotic fluid cartridge 1502 may be connected to a metering pump 1504. In some embodiments, the metering pump may be controlled by a control unit connected to a flow meter 1506, as described herein. In some embodiments, via the control unit and/or a human machine interface, a user may adjust osmolarity of the amniotic fluid. In some embodiments, the metering pump 1504 may pump concentrated into a pipe 1508. Amniotic fluid from the cartridge 1502 and heated purified water from a water heating system 1510 may be delivered into the pipe for mixing. In some embodiments, the mixed fluid may be delivered to a distribution manifold 1512 comprising various sensors (e.g. temperature sensor/controller, pressure sensor/controller, etc.) and control valves connected to the control unit. In some embodiments, an oral administration line valve 1514 may be opened to deliver amniotic fluid to an oral administration line 1516 as shown in FIG. 15.

In some embodiments, a simulated amniotic fluid injection system comprises one or more fresh water baths 1518. The fresh water baths can comprise a disposable and/or replaceable cover. The cover can be sterile in some embodiments. In certain embodiments, the fresh water bath may configured to be filled with a hose attached to faucet with slip-on fitting. The fresh water bath can be configured to be directly and/or indirectly connected to a water supply. In certain embodiments, the fresh water baths can be non-disposable and/or non-replaceable. The fresh water baths can be configured to be disinfected along with other non-disposable and/or non-replaceable components of the system that are in contact with water, synthetic amniotic fluid, cartridge fluid, and/or the patient or infant.

In certain embodiments, one or more water level sensors 1520 can be provided in a simulated amniotic fluid injection system. The one or more water level sensors 1520 can be configured to measure the water level in the bath during a fill process and/or the simulated amniotic fluid level.

In some embodiments, during a bath fill, the simulated amniotic fluid injection system is detached from the main artificial placenta system. In certain embodiments, the simulated amniotic fluid injection system does not need to be detached from the main artificial placenta system during a bath fill. The simulated amniotic fluid injection system can comprise one or more power supplies, such as a rechargeable battery.

In some embodiments, one or more level sensors 1520 of the simulated amniotic fluid injection system are configured to trigger an alarm that the faucet needs to be closed when the bath is full or is near full. In certain embodiments, a water supply is automatically closed when one or more level sensors 1520 of the simulated amniotic fluid injection system detect that the bath is full, near full, and/or at, above, and/or below a predetermined level.

In certain embodiments, if the water level continues to rise above the capacity of the fresh water bath, for example either because an operator or nurse does not close the faucet valve or if the system fails to automatically close the faucet valve, overflow positioned on the top of fresh water tank bath can discharge additional water from the bath through one or more drain openings 1522 out of the system.

In some embodiments, a system disinfection process can be performed periodically and/or continuously. For example, in certain embodiments, system disinfection is performed continuously by allowing disinfection fluid to continuously pass through the system. In some embodiments, system disinfection is performed periodically by allowing disinfection fluid to pass through the system or portions thereof at certain periods, for example when the patient or infant is placed out of the amniotic incubator. Periodic system disinfection can be performed periodically according to a predetermined schedule and/or as needed or convenient, for example when the infant or patient is placed out of the amniotic incubator.

In some embodiments, system disinfection can be performed by inserting a cartridge with concentrated disinfection fluid. For example, a disinfection cartridge may be placed instead of a concentrated amniotic bath fluid cartridge 1502. The contents of the disinfection cartridge can be dissolved in the water and allowed to pass through the system. For example, fresh water can be pumped by one or more pumps via a bypass valve and further into a water heating system 1510. In some embodiments, a disinfection cartridge and one or more amniotic bath fluid cartridges can be color coded using different colors and/or other markings for differentiation between the two. As such, in some embodiments, an operator or nurse can visually notice and/or determine that a correct cartridge has been installed. In certain embodiments, the disinfection can be colored, for example red, orange, yellow, blue, purple, or the like. As such, in certain embodiments, an operator or nurse can easily and/or immediately determine visually if disinfection fluid, or a small amount of disinfection fluid, reaches the amniotic bath while the patient or infant is placed in the bath. In some embodiments, the disinfection cartridge can comprise a shape that is different from that of an amniotic bath fluid cartridge. For example, the disinfection cartridge can comprise a small bump-tab that can be configured to trigger an electro-mechanical sensor. The electro-mechanical sensor, once triggered, can be configured to transmit a signal to a control unit that a disinfection cartridge has been installed. In some embodiments, the control unit can be configured to prevent filling of the amniotic bath until all pre-requirements, such as disinfection, are fulfilled. In certain embodiments, after the disinfection procedure is completed, the system can be washed from remnants of disinfection fluid by being washed by fresh, heated, and/or unheated water through all or a portion of the components of the system that were in contact with the disinfection fluid.

In certain embodiments, the system comprises one or more metering or dosing pumps 1504 to add a controlled amount of concentrated disinfection fluid to the water line to allow for controlled continuous mixing. In some embodiments, concentrated disinfection fluid can be dissolved via a batch process.

The mixed disinfection fluid can be returned to the fresh water bath through one or more valves to disinfect the water bath. For example, the mixed disinfection fluid can pass through a return line through one or more connected slip on fittings. Other portions of the system can be disinfected by pumping the mixed disinfection fluid from fresh water bath making necessary loops to reach all or one or more tubes, fitting and equipment in contact with bath fluid and water. After the disinfection process, remaining fluid can be drained from the system through one or more valves into a wastewater tank and the fresh water bath 1518 can be disposed. The one or more slip-on fittings can be configured to be connected only during the disinfection process.

Computer Systems

Figure 16:
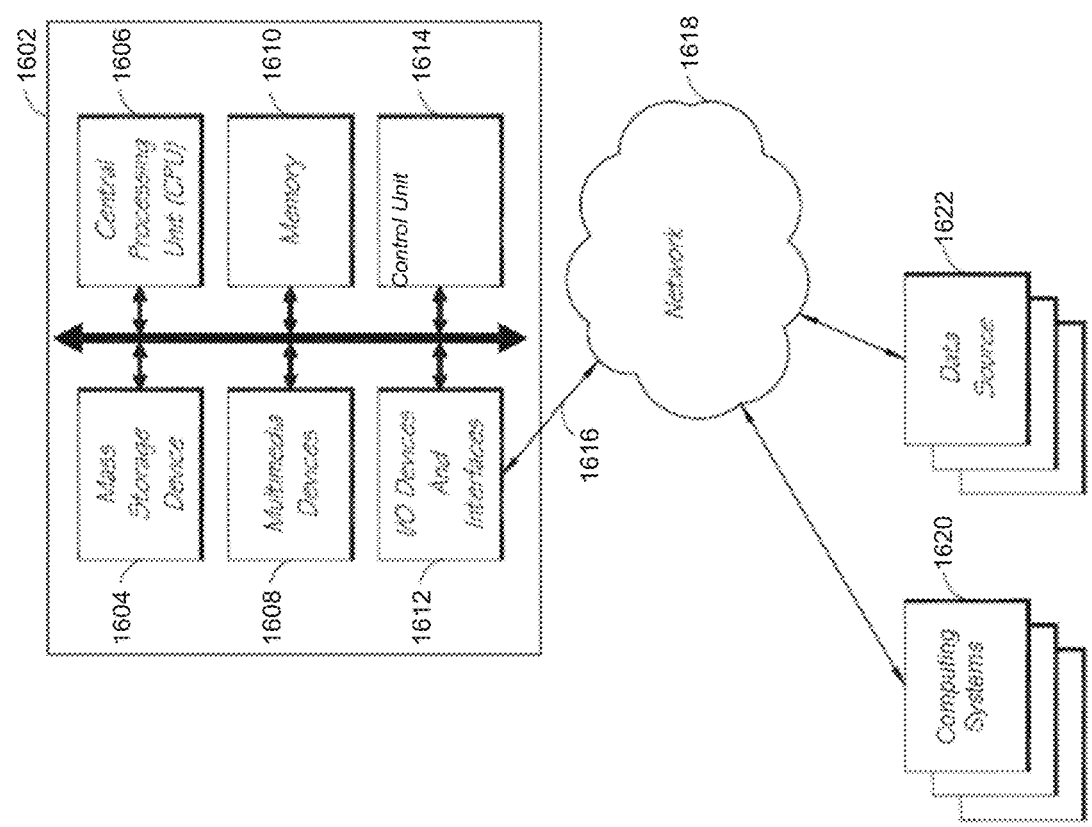
FIG. 16 is a block diagram depicting an embodiment of a computer hardware system configured to run software for implementing one or more embodiments of the control unit of the artificial placenta and amniotic bed systems, methods, and devices disclosed herein.

FIG. 16 is a block diagram depicting an embodiment of a computer hardware system configured to run software for implementing one or more embodiments of the control unit of the artificial placenta and amniotic bed systems, methods, and devices disclosed herein.

In some embodiments, the systems, processes, and methods described herein are implemented using a computing system, such as the one illustrated in FIG. 16. The example computer system 1602 is in communication with one or more computing systems 1620 and/or one or more data sources 1622 via one or more networks 1618. While FIG. 16 illustrates an embodiment of a computing system 1602, it is recognized that the functionality provided for in the components and modules of computer system 1602 may be combined into fewer components and modules, or further separated into additional components and modules.

The computer system 1602 can comprise a control unit 1614 that carries out the functions, methods, acts, and/or processes described herein. The control unit 1614 is executed on the computer system 1602 by a central processing unit 1606 discussed further below. In some embodiments, the control unit 1614 can comprise any and all of the modules described herein.

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1602 includes one or more processing units (CPU) 1606, which may comprise a microprocessor. The computer system 1602 further includes a physical memory 1610, such as random access memory (RAM) for temporary storage of information, a read only memory (ROM) for permanent storage of information, and a mass storage device 1604, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1602 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1602 includes one or more input/output (I/O) devices and interfaces 1612, such as a keyboard, mouse, touch pad, touchscreen and printer. The I/O devices and interfaces 1612 can include one or more display devices, such as a monitor, that allows the visual presentation of data to a user. More particularly, a display device provides for the presentation of GUIs as application software data, and multi-media presentations, for example. The I/O devices and interfaces 1612 can also provide a communications interface to various external devices. The computer system 1602 may comprise one or more multi-media devices 1608, such as speakers, video cards, graphics accelerators, and microphones, for example.

The computer system 1602 may run on a variety of computing devices, such as a server, a Windows server, a Structure Query Language server, a Unix Server, a personal computer, a laptop computer, and so forth. In other embodiments, the computer system 1602 may run on a cluster computer system, a mainframe computer system and/or other computing system suitable for controlling and/or communicating with large databases, performing high volume transaction processing, and generating reports from large databases. The computing system 1602 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1602 illustrated in FIG. 16 is coupled to a network 1618, such as a LAN, WAN, or the Internet via a communication link 1616 (wired, wireless, or a combination thereof). Network 1618 communicates with various computing devices and/or other electronic devices. Network 1618 is communicating with one or more computing systems 1620 and one or more data sources 1622. The control unit 1614 may access or may be accessed by computing systems 1620 and/or data sources 1622 through a web-enabled user access point. Connections may be a direct physical connection, a virtual connection, and other connection type. The web-enabled user access point may comprise a browser module that uses text, graphics, audio, video, and other media to present data and to allow interaction with data via the network 1618. The computer system 16602 can also be connected to other electronic devices, including for example, satellite communications and augmented and/or virtual reality devices (3D or 2D), which may transmit, for example, GPS information.

Access to the control unit 1614 of the computer system 1602 by computing systems 1620 and/or by data sources 1622 may be through a web-enabled user access point such as the computing systems' 1620 or data source's 1622 personal computer, cellular phone, smartphone, laptop, tablet computer, e-reader device, audio player, or another device capable of connecting to the network 1618. Such a device may have a browser module that is implemented as a module that uses text, graphics, audio, video, and other media to present data and to allow interaction with data via the network 1618.

The output module may be implemented as a combination of an all-points addressable display such as a cathode ray tube (CRT), a liquid crystal display (LCD), a plasma display, or other types and/or combinations of displays. The output module may be implemented to communicate with input devices 1612 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 1602 may comprise a physical or logical connection established between a remote microprocessor and a mainframe host computer for the express purpose of uploading, downloading, or viewing interactive data and databases on-line in real time. The remote microprocessor may be operated by an entity operating the computer system 1602, including the client server systems or the main server system, an/or may be operated by one or more of the data sources 1622 and/or one or more of the computing systems 1620. In some embodiments, terminal emulation software may be used on the microprocessor for participating in the micro-mainframe link.

In some embodiments, computing systems 1620 who are internal to an entity operating the computer system 1602 may access the control unit 1614 internally as an application or process run by the CPU 1606.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for web sites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 1602 may include one or more internal and/or external data sources (for example, data sources 1622). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

Figure 17:
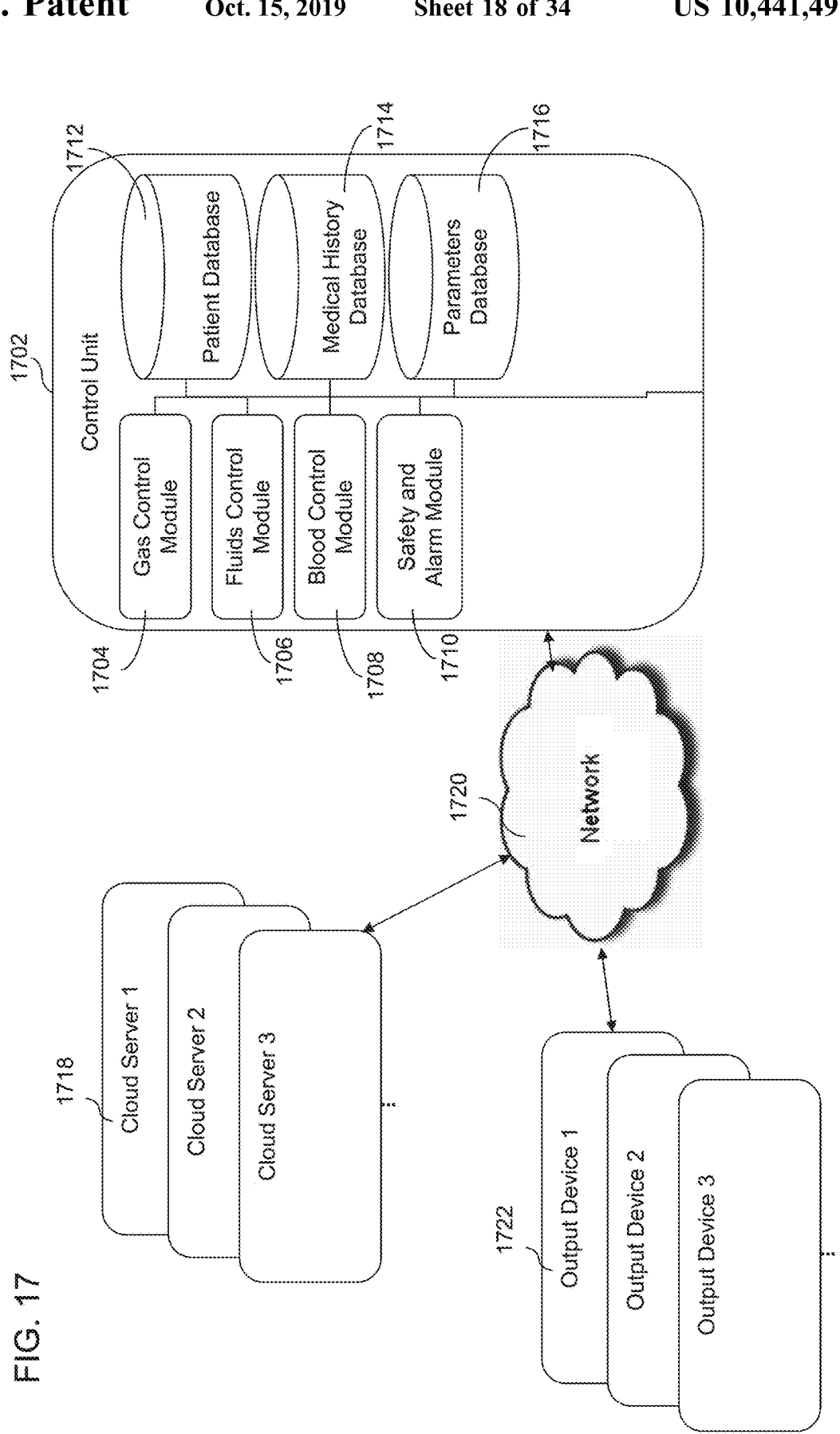
FIG. 17 is a block diagram illustrating an example embodiment of a computer system configured to run software for implementing one or more embodiments of the control unit of the artificial placenta and amniotic bed systems, methods, and devices disclosed herein.

FIG. 17 is a block diagram illustrating an example embodiment of a computer system configured to run software for implementing one or more embodiments of the control unit of the artificial placenta and amniotic bed systems, methods, and devices disclosed herein. In some embodiments, the various systems, methods, and devices described herein may also be implemented in decentralized systems such as, for example, blockchain applications.

In some embodiments, control unit of the artificial placenta and amniotic bed 1702 may be comprised of a gas control module 1704, a fluids control module 1706, a blood control module 1708, and a safety and alarm module 1710, a patient database 1712, a medical history database 1714, and/or a parameters database 1716. The control unit 1702 can be connected to a network 1720. The network 1720 can be configured to connect the control unit 1702 to one or more output devices 1722, including, for example, a human-machine interface, and one or more cloud servers 1718.

The gas control module 1704 may function by obtaining input data streams from a plurality of sensors and data sources as described herein. The gas control module 1704 can be connected to various sensors and valves throughout the system, including within in the gas exchanger and/or the gas delivery unit to monitor and control various chemical and physical properties and flow rates of the gases and gas mixtures moving through the system. In some embodiments, the fluids control module 1706 may function by obtaining input data streams from a plurality of sensors and data sources as described herein. In some embodiments, the fluids control module 1706 can be connected to various sensors and valves throughout the system, including within the gas exchanger and/or the fluids delivery unit to monitor and control various chemical and physical properties and flow rates of the fluids moving through the system. The blood control module 1708 may function by obtaining input data streams from a plurality of sensors and data sources as described herein. The blood control module 1708 can be connected to various sensors and valves throughout the system, including within in the gas exchanger to monitor and control various chemical and physical properties and flow rates of the blood moving through the system. The safety and alarm module 1710 may function by obtaining input data streams from a plurality of sensors and data sources as described herein. The safety and alarm module may be configured to interface with the human-machine interface to alert practitioners to any potential, existing, or predicted issues with the artificial placenta and amniotic bed system or with the infant's medical status.

The patient database 1712 and/or medical history database 1714 comprises patient information, including infant health data and information that may be used by the control system to monitor and control the artificial placenta and amniotic bed system. The parameters database 1716 may comprise one or more system parameters that may be used in the control unit algorithms to control the properties and flow of gas, fluids, and blood within the system, and to generate alerts and/or alarms to be displayed in the human-machine interface.

Figure 18A:
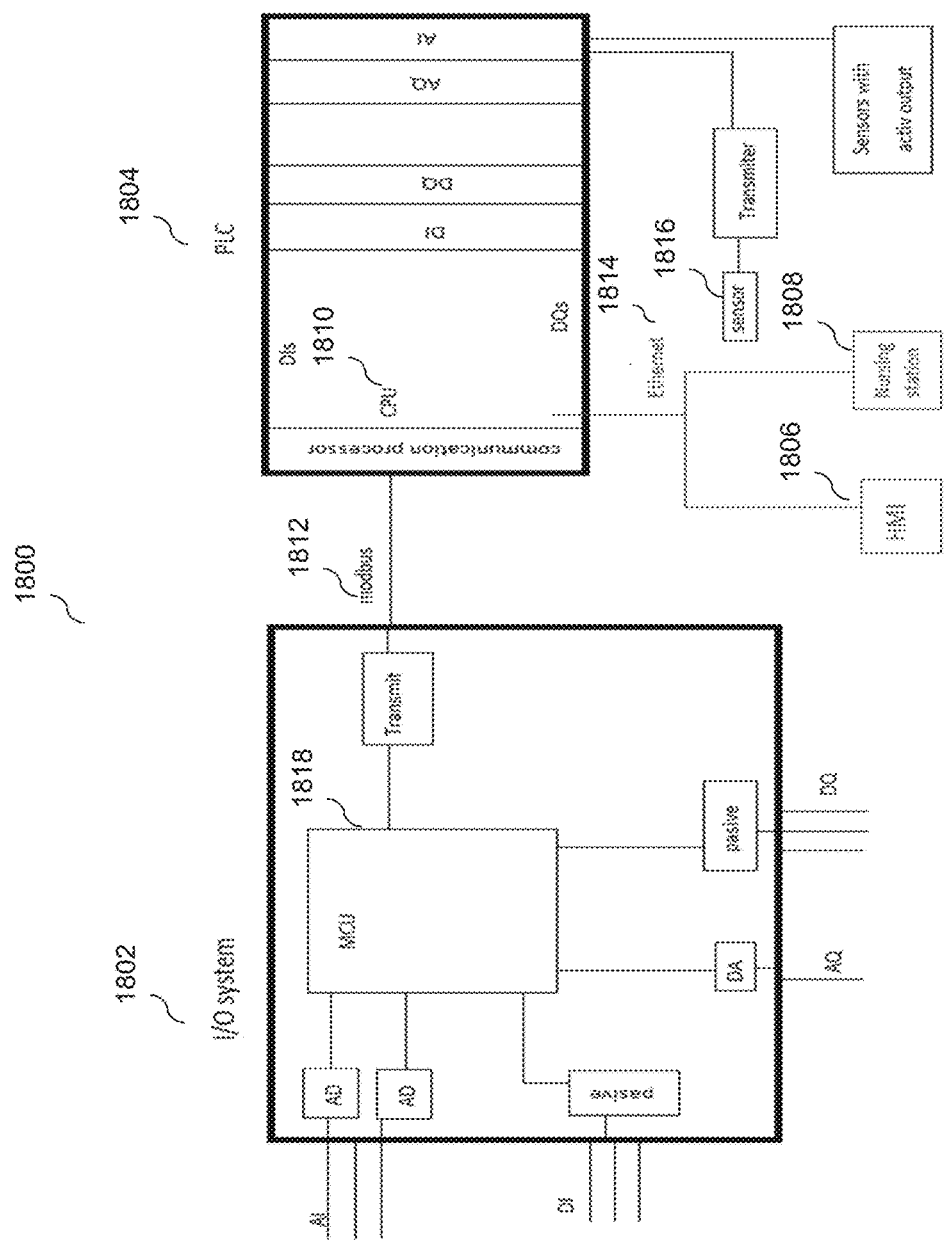
FIG. 18A illustrates an example control unit and human machine interface diagram according to various embodiments herein.

FIG. 18A illustrates an example control unit and human machine interface diagram according to various embodiments herein. In some embodiments, the control unit and monitoring system 1800 comprises four subsystems: an input/output (I/O) module 1802 that develops and displays proprietary software such as Amnionlife; a programmable logic controller (PLC) 1804, which may be a standard modular device; a human machine interface (HMI) 1806 configured to provide a usable interface between users and the control unit and monitoring system; and a "Nursing station" 1808, which may be a software application that serves for monitoring of the system and acquisition of data received from the system.

In some embodiments, the PLC 1804 may comprise one or more central processing units (CPUs) 1810. In some embodiments, the one or more CPUs 1810 process data received from: I/O system 1802, which may be received through a modbus 1812 or other communications processor; one or more inputs of the one or more CPUs 1810; one or more modules of the PLC 1804; via the HMI 1806 through, for example, an Ethernet connection 1814.

In some embodiments, the PLC system 1804 may be an industrial solution for monitoring and controlling the operation of the artificial placenta methods, systems, and devices herein. In some embodiments, the one or more CPUs 1810 may be programmed with a graphical environment, which may be configured to monitor the system online and change programs without restart and/or shutting down the entire system. The control unit and monitoring system may also comprise a ledger diagram. By writing software in the ledger diagram, it may be simpler to track changes and debug any issues with the software. In some embodiments, the PLC manufacturers may deliver a PLC 1804 equipped with standard control functions (e.g. PID) and communication protocols (e.g. modbus). In some embodiments, the PLC system 1804 may be upgradable. In some embodiments, the PLC 1804 may comprise standard communication ports. A number of different HMIs 1806 may be mutually compatible with the PLC system 1804.

In some embodiments, the system may comprise a small number of PLCs 1804 in a relatively slow scan of the system (e.g. greater than 10 ms), with a small number of fast (e.g. 100 kHz) inputs and outputs. In some embodiments, some of the processing of inputs and/or generation of outputs may be completed on the CPU.

In some embodiments, the I/O module 1802 may be designed to meet needs that cannot be achieved with standard PLC extensions, and to reduce the overall size of the extensions system. In some embodiments, because of the specific requirements for the scope and accuracy of measurement, as well as for specific dimensions, a specialized I/O component may be needed. In some embodiments, if the I/O selection condition is only the shape and functionality of the component, the choice of components may be significantly increased, but use of non-specialized components may require significant adjustments to the system.

In some embodiments, the I/O module 1802 may configured to measure the intensity of physical quantities (e.g. temperature, pressure, flow etc.) of blood, fluids, and/or gases with the necessary accuracy and with the required resolution using one or more sensors 1816. In some embodiments, the I/O module 1802 may be configured to count very fast digital signals (e.g. pulse from measure of flow). In some embodiments, the I/O system 1802 may be configured to control, for example, pulse width modulation (PWM) (e.g. faster than 1 ms, up to 20 microseconds) and Digital-Analog conversion. In some embodiments, the I/O system 1802 may be configured to read sensors using a processor's communications protocols (e.g. SPI, I2C). In some embodiments, the I/O system 1802 may comprise one or more microcontroller 1818 configured to complete the functions described herein.

Figure 18B:
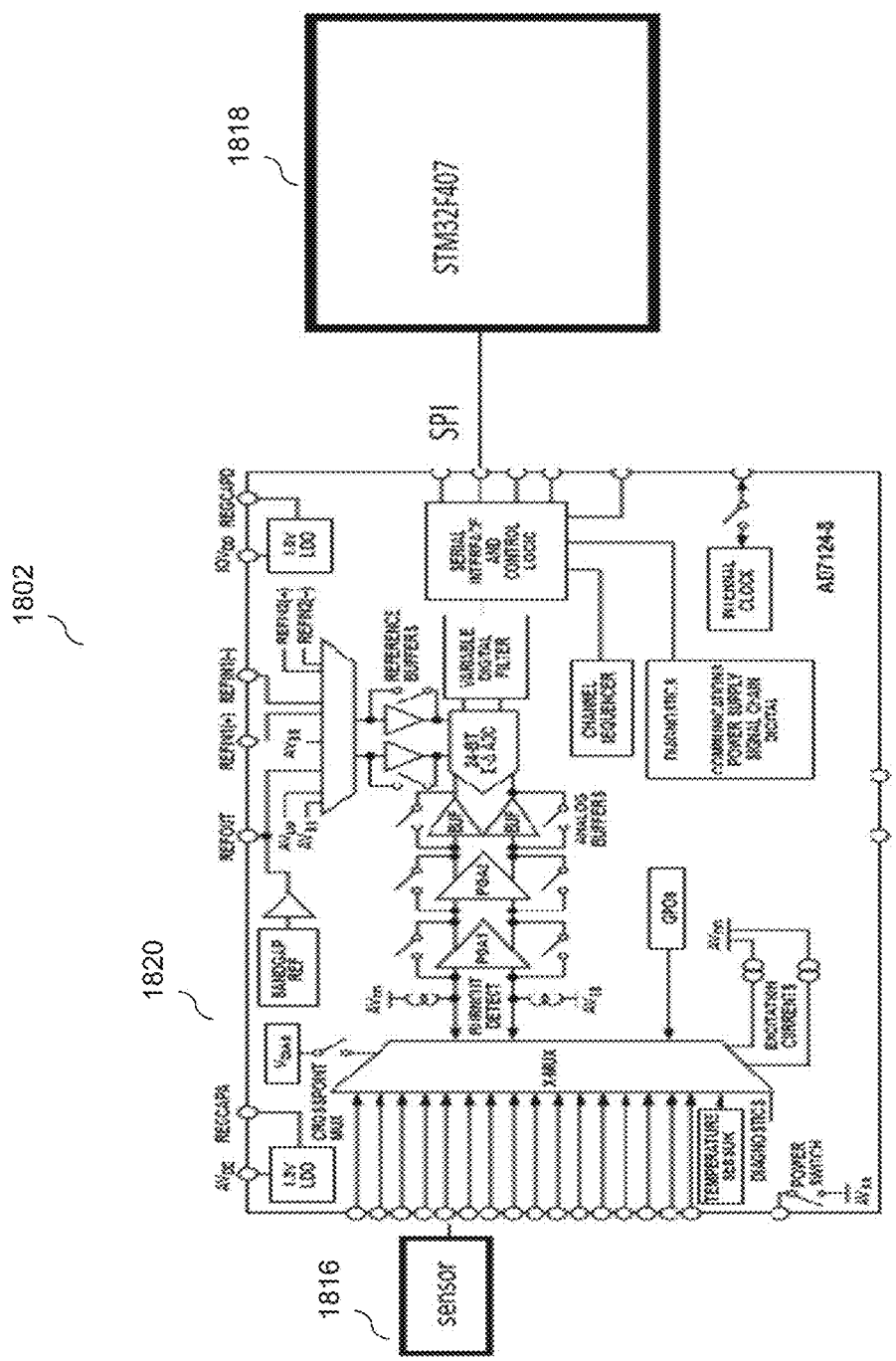
FIG. 18B illustrates an example I/O unit of the artificial placenta methods, systems, and devices according to various embodiments herein.

FIG. 18B illustrates an example I/O unit 1802 of the artificial placenta methods, systems, and devices according to various embodiments herein. In some embodiments, the functions and requirements described above can be completed using a fast and high-quality micro controller unit (MCU) 1818, for example, STM32F407. In some embodiments, a chip with high-quality and precise AD converter 1820, such as AD7124 may be used.

In some embodiments, the I/O device 1804 may send data to the control unit, and receives commands in return. In some embodiments, this functionality ensures that conditions and events from the periphery of the system do not alter the functions of the software of the I/O system 1804. In some embodiments, programming of the MCU 1818 may be much more complicated than the ledger diagrams on the PLC 1804. As a result, in some embodiments, when the I/O is constructed to represent the interface needed, some or all of the other conditions are solved at the PLC 1804 level.

In some embodiments, the applied AD converter 1820 may comprise, for example, 24 bit resolution, an integrated reference voltage, a programmable instrumentation amplifier, a programmable input pin functionality, a programmable frequency band filter, a programmable offset per channel, and/or an input impedance of, for example, about a giga-ohm. In some embodiments, precise measurements are possible with the AD converter 1820 described herein.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Those skilled in the art will recognize various means for carrying out these intended features of the embodiments disclosed herein. As such, it is to be understood that other systems, methods, applications and devices may be configured to carry out these features and are therefore considered to be within the scope and intent of the present invention, and are anticipated. With respect to the above description, it is to be understood that the embodiments are not limited in their application to the details of construction and to the arrangement of the components in the description or illustrated in the drawings. The embodiments herein described are capable of modification and of being practiced and carried out in various ways which will be obvious to those skilled in the art. Also, it is to be understood that the phraseology and terminology employed herein are for the purpose of description and should not be regarded as limiting.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

The ranges disclosed herein also encompass any and all overlap, sub-ranges, and combinations thereof. Language such as "up to," "at least," "greater than," "less than," "between," and the like includes the number recited and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Numbers preceded by a term such as "about" or "approximately" include the recited numbers. For example, "about 3 mm" includes "3 mm."

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

The headings provided herein, if any, are for convenience only and do not necessarily affect the scope or meaning of the devices and methods disclosed herein.

What is claimed is:

1. An extracorporeal artificial placenta and amniotic bed system for the administration of oxygenated blood through an umbilical cord of an infant, the extracorporeal artificial placenta and amniotic bed system comprising:
    a simulated amniotic fluid bed comprising a thermo-regulated fluid environment configured to accommodate a body of the infant therein while maintaining a head of the infant above the thermo-regulated fluid environment;
    a fluid injection system connected to an amniotic fluid source, the fluid injection system configured to fill lungs of the infant with simulated amniotic fluid while the head of the infant is maintained above the thermo-regulated fluid environment; and
    an extra-uterine membrane oxygenation system configured to oxygenate blood of the infant, the extra-uterine membrane oxygenation system comprising:
        one or more arterial lines adapted to connect to the umbilical cord of the infant and configured to receive low-oxygen blood from the infant;
        a gas exchange unit comprising:
            an inflow capillary tree comprising a first branching structure, wherein the inflow capillary tree is configured to deliver the low-oxygen blood to a hollow fiber unit comprising one or more semi-permeable hollow fibers capable of oxygenating the low-oxygen blood passing through the hollow fiber unit; and
            an outflow capillary tree comprising a second branching structure, wherein the second branching structure mirrors the first branching structure, and wherein the outflow capillary tree is configured to deliver oxygenated blood from the hollow fiber unit; and
        one or more venous lines adapted to connect to the umbilical cord of the infant and configured to receive the oxygenated blood from the outflow capillary tree and deliver the oxygenated blood to the infant;
        wherein the one or more hollow fibers are positioned in a geometric array, wherein each of the one or more hollow fibers is located substantially equidistantly from each adjacent hollow fiber of the hollow fiber unit, and
        wherein each of the one or more hollow fibers is oriented substantially parallel each other hollow fiber.

2. The extracorporeal artificial placenta and amniotic bed system of claim 1, wherein the extra-uterine membrane oxygenation system further comprises a catheter adapted to connect the one or more arterial lines and the one or more venous lines to the umbilical cord of the infant.

3. The extracorporeal artificial placenta and amniotic bed system of claim 2, wherein the extra-uterine membrane oxygenation system further comprises an anchor for maintaining the catheter above the thermo-regulated fluid environment.

4. The extracorporeal artificial placenta and amniotic bed system of claim 1, wherein the first branching structure of the inflow capillary tree and the second branching structure of the outflow capillary tree comprise one or more branching angles or branch diameters that naturally occur in a human body, such that the inflow capillary tree and outflow capillary tree mimic a branching of a natural capillary tree.

5. The extracorporeal artificial placenta and amniotic bed system of claim 1, wherein the simulated amniotic fluid bed further comprises:
 an incubating tank comprising simulated amniotic fluid;
 one or more heating elements;
 one or more temperature sensors; and
 one or more thermostats comprising a temperature regulation mechanism.

6. The extracorporeal artificial placenta and amniotic bed system of claim 5, wherein the simulated amniotic fluid comprises one or more of the following:
 electrolytes, minerals, proteins, peptides, lipids, lactate, pyruvate, enzymes, hormones, or amniotic stem cells.

7. The extracorporeal artificial placenta and amniotic bed system of claim 1, further comprising a gas delivery unit configured to supply a gas mixture to the gas exchange unit at a predetermined pressure and/or temperature, the gas delivery unit comprising:
 a gas supply;
 one or more inlet gas connectors configured to deliver one or more gases from the gas supply to an interior of the gas delivery unit;
 one or more gas control valves configured to control the flow of the one or more gases;
 a blender configured to blend the one or more gases into the gas mixture at a predetermined mixing ratio;
 a gas filter comprising a porous filter membrane configured to prevent impurities from entering the gas mixture; and
 one or more outlet gas connectors configured to deliver the gas mixture from the interior of the gas delivery unit to the gas exchange unit.

8. The extracorporeal artificial placenta and amniotic bed system of claim 7, wherein the gas mixture comprises oxygen and ambient air.

9. The extracorporeal artificial placenta and amniotic bed system of claim 7, wherein the gas supply comprises a central gas delivery system of a hospital.

10. The extracorporeal artificial placenta and amniotic bed system of claim 1, further comprising a graphical user interface configured to allow a user to monitor and control the simulated amniotic fluid bed extra-uterine membrane oxygenation system.

11. The extracorporeal artificial placenta and amniotic bed system of claim 1, further comprising a fluids delivery unit configured to deliver one or more fluids to the blood of the infant, the fluids delivery unit comprising:
 one or more fluid tanks, each fluid tank storing a fluid of the one or more fluids;
 one or more fluid pumps configured to meter the fluids at a predetermined flow rate into the one or more arterial lines and/or the one or more venous lines.

12. The extracorporeal artificial placenta and amniotic bed system of claim 11, wherein at least one of the one or more fluid tanks comprises a disposable fluid cartridge.

13. The extracorporeal artificial placenta and amniotic bed system of claim 11, wherein the one or more fluids comprise simulated amniotic fluid, nutrients, or Heparin.

14. The extracorporeal artificial placenta and amniotic bed system of claim 1, wherein the one or more venous lines comprise a bubble trap configured to remove bubbles from the one or more venous lines.

15. The extracorporeal artificial placenta and amniotic bed system of claim 1, wherein the one or more venous lines comprise a Luer port configured to allow direct pharmaceuticals administration to the oxygenated blood.

16. The extracorporeal artificial placenta and amniotic bed system of claim 1, further comprising a control unit configured to monitor and control the simulated amniotic fluid bed and/or the extra-uterine membrane oxygenation system, the control unit comprising:
 a plurality of system sensors configured to transmit system state data;
 a plurality of system control valves;
 one or more computer readable storage devices configured to store a plurality of computer executable instructions; and
 one or more hardware computer processors in communication with the one or more computer readable storage devices and configured to execute the plurality of computer executable instructions in order to cause the control unit to:
  continuously monitor the artificial placenta and amniotic bed system by receiving and analyzing the system state data from the plurality of system sensors;
  control one or more physical or chemical properties of blood, gas, and/or fluid within the extracorporeal artificial placenta and amniotic bed system by sending a generated command to the one or more of the plurality of system control valves.

17. The extracorporeal artificial placenta and amniotic bed system of claim 1, wherein the gas exchange unit further comprises a jacket, wherein the jacket encases the hollow fiber unit and seals an interior of the gas exchange unit.

18. The extracorporeal artificial placenta and amniotic bed system of claim 1, wherein the fluid injection system comprises one or more tubes, and wherein the one or more tubes are adapted to attach to one or both nostrils and/or a mouth of the infant.

19. A clinical method for maintaining fetal blood circulation, providing a normal partial pressure of oxygen in lungs of an infant patient, and avoiding potentially harmful mechanical ventilation to the lungs, the clinical method comprising:
 placing a body of the infant patient in a simulated amniotic fluid bed comprising a thermo-regulated fluid environment configured to accommodate the infant therein while maintaining a head of the infant patient above the thermo-regulated fluid environment;
 connecting a fluid injection system to the infant patient, the fluid injection system connected to an amniotic fluid source, the fluid injection system configured to fill lungs of the infant patient with simulated amniotic fluid while the head of the infant patient is maintained above the thermo-regulated fluid environment;
 connecting, to the infant patient, an extra-uterine membrane oxygenation system configured to oxygenate the blood of the infant patient, the extra-uterine membrane oxygenation system comprising:

one or more arterial lines connected to the umbilical cord of the infant patient and configured to receive low-oxygen blood from the infant patient;

a gas exchange unit comprising:
- an inflow capillary tree comprising a first branching structure, wherein the inflow capillary tree is configured to deliver the low-oxygen blood to a hollow fiber unit comprising one or more semipermeable hollow fibers capable of oxygenating the low-oxygen blood passing through the hollow fiber unit; and
- an outflow capillary tree comprising a second branching structure, wherein the second branching structure mirrors the first branching structure, and wherein the outflow capillary tree is configured to deliver oxygenated blood from the hollow fiber unit,
- wherein the one or more semipermeable hollow fibers are positioned in a geometric array, wherein each of the one or more semipermeable hollow fibers is located substantially equidistantly from each adjacent semipermeable hollow fiber of the hollow fiber unit, and wherein each of the one or more semipermeable hollow fibers is oriented substantially parallel each other semipermeable hollow fiber; and
- one or more venous lines connected to the umbilical cord of the infant patient and configured-to receive the oxygenated blood from the outflow capillary tree and deliver the oxygenated blood to the infant patient;

receive low-oxygen blood from the infant patient through the one or more arterial lines;

oxygenate the low-oxygen blood within the extra-uterine membrane oxygenation system; and deliver the oxygenated blood to the infant patient.

20. The clinical method of claim 19, wherein the first branching structure of the inflow capillary tree and the second branching structure of the outflow capillary tree comprise one or more branching angles or branch diameters that naturally occur in a human body, such that the inflow capillary tree and outflow capillary tree mimic a branching of a natural capillary tree.

* * * * *